(12) United States Patent
Fairfax et al.

(10) Patent No.: US 9,278,940 B2
(45) Date of Patent: Mar. 8, 2016

(54) CYCLIC AMINES AS BROMODOMAIN INHIBITORS

(71) Applicants: David John Fairfax, Slingerlands, NY (US); Bryan Cordell Duffy, Glenmont, NY (US); Gregory Scott Martin, Colonie, NY (US); John Frederick Quinn, Albany, NY (US); Shuang Liu, Schenectady, NY (US); Gregory Steven Wagner, Foster City, CA (US); Peter Ronald Young, San Francisco, CA (US)

(72) Inventors: David John Fairfax, Slingerlands, NY (US); Bryan Cordell Duffy, Glenmont, NY (US); Gregory Scott Martin, Colonie, NY (US); John Frederick Quinn, Albany, NY (US); Shuang Liu, Schenectady, NY (US); Gregory Steven Wagner, Foster City, CA (US); Peter Ronald Young, San Francisco, CA (US)

(73) Assignee: Zenith Epigenetics Corp., Calgary, Alberta (CA)

( * ) Notice: Subject to any disclaimer, the term of this patent is extended or adjusted under 35 U.S.C. 154(b) by 0 days.

(21) Appl. No.: 14/729,959

(22) Filed: Jun. 3, 2015

(65) Prior Publication Data

US 2015/0344442 A1     Dec. 3, 2015

Related U.S. Application Data

(62) Division of application No. 14/085,545, filed on Nov. 20, 2013, now Pat. No. 9,073,878.

(60) Provisional application No. 61/729,097, filed on Nov. 21, 2012.

(51) Int. Cl.
| | |
|---|---|
| *A61K 31/517* | (2006.01) |
| *C07D 239/91* | (2006.01) |
| *C07D 265/32* | (2006.01) |
| *A61K 45/06* | (2006.01) |
| *C07D 401/04* | (2006.01) |
| *A61K 31/5377* | (2006.01) |
| *C07D 401/14* | (2006.01) |

(52) U.S. Cl.
CPC ............ *C07D 239/91* (2013.01); *A61K 31/517* (2013.01); *A61K 31/5377* (2013.01); *A61K 45/06* (2013.01); *C07D 265/32* (2013.01); *C07D 401/04* (2013.01); *C07D 401/14* (2013.01)

(58) Field of Classification Search
CPC .......................... A61K 31/517; C07D 239/91
See application file for complete search history.

(56) References Cited

U.S. PATENT DOCUMENTS

| | | | |
|---|---|---|---|
| 2,065,593 | A | 12/1936 | Lubs |
| 2,065,900 | A | 12/1936 | Laska et al. |
| 2,071,329 | A | 2/1937 | Brown |
| 3,251,837 | A | 5/1966 | Holland |
| 3,600,394 | A | 8/1971 | Coyne et al. |
| 3,773,946 | A | 11/1973 | Creger |
| 3,930,024 | A | 12/1975 | Creger |
| 3,965,128 | A | 6/1976 | Fürst et al. |
| 4,613,593 | A | 9/1986 | Yamatsu et al. |
| 4,689,344 | A | 8/1987 | Bar-Tana |
| 4,711,896 | A | 12/1987 | Bar-Tana et al. |
| 4,825,005 | A | 4/1989 | Frey et al. |
| 5,098,903 | A | 3/1992 | Magarian et al. |
| 5,124,337 | A | 6/1992 | Dugar et al. |
| 5,126,351 | A | 6/1992 | Luzzio et al. |
| 5,244,904 | A | 9/1993 | Nagase et al. |
| 5,280,024 | A | 1/1994 | Bolland et al. |
| 5,354,749 | A | 10/1994 | Dressel et al. |
| 5,407,942 | A | 4/1995 | Dressel et al. |
| 5,409,930 | A | 4/1995 | Spada et al. |
| 5,446,071 | A | 8/1995 | Grese |
| 5,474,994 | A | 12/1995 | Leonardi et al. |
| 5,480,883 | A | 1/1996 | Spada et al. |
| 5,539,119 | A | 7/1996 | Nagase et al. |
| 5,576,322 | A | 11/1996 | Takase et al. |
| 5,595,974 | A | 1/1997 | Tomaru |
| 5,693,652 | A | 12/1997 | Takase et al. |
| 5,707,987 | A | 1/1998 | Nakagawa et al. |
| 5,733,913 | A | 3/1998 | Blankley et al. |
| 5,756,344 | A | 5/1998 | Onda et al. |
| 5,756,544 | A | 5/1998 | Bisgaier et al. |
| 5,756,736 | A | 5/1998 | Arzeno et al. |
| 5,756,763 | A | 5/1998 | Takeuchi et al. |
| 5,763,414 | A | 6/1998 | Bok et al. |
| 5,783,577 | A | 7/1998 | Houghten et al. |
| 5,792,461 | A | 8/1998 | Bok et al. |
| 5,792,902 | A | 8/1998 | Benoit et al. |
| 5,798,344 | A | 8/1998 | Kuroki et al. |
| 5,801,180 | A | 9/1998 | Takase et al. |
| 5,817,674 | A | 10/1998 | Clemence et al. |
| 5,854,264 | A | 12/1998 | Anthony et al. |
| 5,877,208 | A | 3/1999 | Bok et al. |
| 5,922,866 | A | 7/1999 | Miyata et al. |

(Continued)

FOREIGN PATENT DOCUMENTS

| | | |
|---|---|---|
| AU | 719140 B2 | 7/1998 |
| CA | 2104981 A1 | 3/1994 |

(Continued)

OTHER PUBLICATIONS

Abdel-Jalil et al., "Synthesis and Antitumor Activity of 2-Aryl-7-fluoro-6-(4-methyl-1-piperazinyl)-4(3*H*)-quinazolinones" *Heterocyles* 65(9):2061-2070 (2005).

(Continued)

*Primary Examiner* — Wu-Cheng Winston Shen
*Assistant Examiner* — Christopher R Stone
(74) *Attorney, Agent, or Firm* — Finnegan, Henderson, Farabow, Garrett & Dunner, LLP

(57) ABSTRACT

The present disclosure relates to compounds, which are useful for inhibition of BET protein function by binding to bromodomains, and their use in therapy.

31 Claims, No Drawings

(56) References Cited

U.S. PATENT DOCUMENTS

| | | | |
|---|---|---|---|
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |
| 6,239,114 B1 | 5/2001 | Guthrie et al. |
| 6,291,456 B1 | 9/2001 | Stein et al. |
| 6,303,629 B1 | 10/2001 | Kun |
| 6,340,759 B1 | 1/2002 | Ueno et al. |
| 6,380,235 B1 | 4/2002 | Zhang et al. |
| 6,414,037 B1 | 7/2002 | Pezzuto et al. |
| 6,455,577 B2 | 9/2002 | Bok et al. |
| 6,479,499 B1 | 11/2002 | Kuo et al. |
| 6,482,479 B1 | 11/2002 | Dubal et al. |
| 6,512,161 B1 | 1/2003 | Rouy et al. |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B1 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 8,735,586 B2 | 5/2014 | Alonso et al. |
| 8,952,021 B2 | 2/2015 | Hansen |
| 9,073,878 B2 | 7/2015 | Fairfax et ai. |
| 2002/0019395 A1 | 2/2002 | Zhu et al. |
| 2003/0036545 A1 | 2/2003 | Castelhano et al. |
| 2004/0166137 A1 | 8/2004 | Lackey |
| 2005/0176858 A1 | 8/2005 | Nohara at al. |
| 2007/0275984 A1 | 11/2007 | Imogai et al. |
| 2008/0015196 A1 | 1/2008 | Doller et al. |
| 2010/0234354 A1 | 9/2010 | Dorsch et al. |
| 2010/0267714 A1 | 10/2010 | Jorgensen et al. |
| 2011/0136819 A1 | 6/2011 | Dorsch et al. |
| 2011/0257181 A1 | 10/2011 | Stieber et al. |
| 2012/0028912 A1 | 2/2012 | Zhou et al. |
| 2012/0157428 A1 | 6/2012 | Albrecht et al. |
| 2012/0208798 A1 | 8/2012 | Demont et al. |
| 2012/0220573 A1 | 8/2012 | Gosmini et al. |
| 2013/0085133 A1 | 4/2013 | Severson et al. |
| 2013/0143880 A1 | 6/2013 | Dudkin et al. |
| 2013/0261109 A1 | 10/2013 | Miyoshi et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0031336 A1 | 1/2014 | Amans et al. |
| 2014/0045834 A1 | 2/2014 | Demont et al. |
| 2014/0107369 A1 | 4/2014 | Lozanov et al. |
| 2014/0140956 A1 | 5/2014 | Fairfax et al. |
| 2014/0162971 A1 | 6/2014 | Wang et al. |
| 2014/0171462 A1 | 6/2014 | Demont et al. |
| 2014/0179648 A1 | 6/2014 | Liu et al. |
| 2014/0256700 A1 | 9/2014 | Poss et al. |
| 2014/0256705 A1 | 9/2014 | Hasvold et al. |
| 2014/0256706 A1 | 9/2014 | Wang et al. |
| 2014/0256710 A1 | 9/2014 | Liu et al. |
| 2014/0275030 A1 | 9/2014 | Combs et al. |
| 2014/0275079 A1 | 9/2014 | Hasvold et al. |
| 2014/0296246 A1 | 10/2014 | Aktoudianakis et al. |
| 2014/0303121 A1 | 10/2014 | Zhang et al. |
| 2014/0336190 A1 | 11/2014 | Aktoudianakis et al. |
| 2014/0349990 A1 | 11/2014 | Blank et al. |
| 2015/0011540 A1 | 1/2015 | Combs et al. |
| 2015/0072955 A1 | 3/2015 | Hansen |

FOREIGN PATENT DOCUMENTS

| | | | |
|---|---|---|---|
| CA | 2345406 A1 | 4/2000 |
| CA | 2440211 A1 | 9/2002 |
| CA | 2815127 A1 | 4/2012 |
| CA | 2818187 A1 | 6/2012 |
| CN | 1067070 C | 6/2001 |
| CN | 1430599 A | 7/2003 |
| CN | 102731409 A | 10/2012 |
| DE | 652772 | 11/1937 |
| DE | 35 32 279 A1 | 3/1987 |
| DE | 36 01 417 A1 | 7/1987 |
| DE | 42 15 588 A1 | 11/1993 |
| DE | 196 51 099 A1 | 6/1998 |
| DE | 197 56 388 A1 | 6/1999 |
| DE | 199 34 799 A1 | 2/2001 |
| EP | 0 210 342 A2 | 2/1987 |
| EP | 0 182 213 B1 | 9/1990 |
| EP | 0 407 217 A1 | 1/1991 |
| EP | 0 410 834 A1 | 1/1991 |
| EP | 0 258 190 B1 | 11/1991 |
| EP | 0 488 602 A1 | 6/1992 |
| EP | 0 272 455 B1 | 2/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 569 795 B1 | 4/1995 |
| EP | 0 330 108 B1 | 12/1995 |
| EP | 0 747 051 A2 | 12/1996 |
| EP | 0 564 350 B1 | 5/1997 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |
| EP | 1 477 481 A1 | 11/2004 |
| EP | 1 757 894 A1 | 2/2007 |
| EP | 1 637 523 A1 | 3/2008 |
| EP | 1 944 301 A1 | 7/2008 |
| EP | 2 005 941 A2 | 12/2008 |
| EP | 2 196 465 A1 | 6/2010 |
| EP | 2 390 250 A2 | 11/2011 |
| EP | 2 792 355 A1 | 12/2014 |
| FR | 2 244 492 | 4/1975 |
| FR | 2 244 493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| IE | 902587 A1 | 7/1990 |
| JP | 6-80656 A | 3/1994 |
| JP | 7-41442 A | 2/1995 |
| JP | 7-61942 A | 3/1995 |
| JP | 7-118241 A | 5/1995 |
| JP | 7-179380 A | 7/1995 |
| JP | 7-233109 A | 9/1995 |
| JP | 7-247289 A | 9/1995 |
| JP | 10-287678 A | 10/1998 |
| JP | 2004-511502 A | 4/2001 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| KR | 10-0707532 B1 | 8/2005 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 8/1995 |
| WO | WO 96/31206 A2 | 10/1996 |

(56) References Cited

FOREIGN PATENT DOCUMENTS

| | | |
|---|---|---|
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 00/13671 A1 | 3/2000 |
| WO | WO 00/17184 A1 | 3/2000 |
| WO | WO 00/23075 A1 | 4/2000 |
| WO | WO 00/34248 A1 | 6/2000 |
| WO | WO 00/35865 A2 | 6/2000 |
| WO | WO 00/44362 A2 | 8/2000 |
| WO | WO 00/55168 A1 | 9/2000 |
| WO | WO 00/64888 A1 | 11/2000 |
| WO | WO 00/66564 A1 | 11/2000 |
| WO | WO 01/00554 A2 | 1/2001 |
| WO | WO 01/55132 A1 | 8/2001 |
| WO | WO 01/60775 A1 | 8/2001 |
| WO | WO 01/82916 A2 | 11/2001 |
| WO | WO 01/83456 A1 | 11/2001 |
| WO | WO 01/90051 A1 | 11/2001 |
| WO | WO 02/32377 A2 | 4/2002 |
| WO | WO 02/44189 A1 | 6/2002 |
| WO | WO 02/067675 A2 | 9/2002 |
| WO | WO 02/074307 A1 | 9/2002 |
| WO | WO 02/076976 A2 | 10/2002 |
| WO | WO 02/078708 A1 | 10/2002 |
| WO | WO 02/087556 A2 | 11/2002 |
| WO | WO 02/096426 A1 | 12/2002 |
| WO | WO 03/007959 A1 | 1/2003 |
| WO | WO 03/016292 A1 | 2/2003 |
| WO | WO 03/018008 A1 | 3/2003 |
| WO | WO 03/040256 A2 | 5/2003 |
| WO | WO 03/040257 A1 | 5/2003 |
| WO | WO 03/070236 A2 | 8/2003 |
| WO | WO 03/099274 A1 | 12/2003 |
| WO | WO 03/106435 A1 | 12/2003 |
| WO | WO 2004/017920 A2 | 3/2004 |
| WO | WO 2004/019933 A1 | 3/2004 |
| WO | WO 2004/032846 A2 | 4/2004 |
| WO | WO 2004/037176 A2 | 5/2004 |
| WO | WO 2004/039795 A2 | 5/2004 |
| WO | WO 2004/047755 A2 | 6/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/078733 A1 | 9/2004 |
| WO | WO 2004/092196 A2 | 10/2004 |
| WO | WO 2004/094452 A2 | 11/2004 |
| WO | WO 2004/108139 A2 | 12/2004 |
| WO | WO 2004/112710 A2 | 12/2004 |
| WO | WO 2005/034960 A1 | 4/2005 |
| WO | WO 2005/042712 A2 | 5/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/075432 A1 | 8/2005 |
| WO | WO 2005/090317 A1 | 9/2005 |
| WO | WO 2005/115993 A1 | 12/2005 |
| WO | WO 2005/117876 A1 | 12/2005 |
| WO | WO 2006/012577 A2 | 2/2006 |
| WO | WO 2006/045096 A2 | 4/2006 |
| WO | WO 2006/071095 A1 | 7/2006 |
| WO | WO 2006/105081 A2 | 10/2006 |
| WO | WO 2006/119400 A2 | 11/2006 |
| WO | WO 2007/016525 A2 | 2/2007 |
| WO | WO 2007/071055 A1 | 6/2007 |
| WO | WO 2007/093901 A1 | 8/2007 |
| WO | WO 2008/054599 A2 | 5/2008 |
| WO | WO 2008/072784 A1 | 6/2008 |
| WO | WO 2008/092231 A1 | 8/2008 |
| WO | WO 2008/152471 A1 | 12/2008 |
| WO | WO 2009/006959 A1 | 1/2009 |
| WO | WO 2009/024221 A1 | 2/2009 |
| WO | WO 2009/054790 A1 | 4/2009 |
| WO | WO 2009/099801 A1 | 8/2009 |
| WO | WO 2009/158258 A1 | 12/2009 |
| WO | WO 2010/015520 A1 | 2/2010 |
| WO | WO 2010/068483 A2 | 6/2010 |
| WO | WO 2010/072296 A1 | 7/2010 |
| WO | WO 2010/077275 A1 | 7/2010 |
| WO | WO 2010/100178 A1 | 9/2010 |
| WO | WO 2010/104851 A1 | 9/2010 |
| WO | WO 2010/106436 A2 | 9/2010 |
| WO | WO 2010/123975 A1 | 10/2010 |
| WO | WO 2011/143669 A2 | 1/2011 |
| WO | WO 2011/054843 A1 | 5/2011 |
| WO | WO 2011/054846 A1 | 5/2011 |
| WO | WO 2011/156626 A1 | 12/2011 |
| WO | WO 2011/159926 A1 | 12/2011 |
| WO | WO 2012/009258 A2 | 1/2012 |
| WO | WO 2012/021382 A1 | 2/2012 |
| WO | WO 2012/040499 A2 | 3/2012 |
| WO | WO 2012/075456 A1 | 6/2012 |
| WO | WO 2012/143413 A1 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/031928 A2 | 12/2013 |
| WO | WO 2014/043246 A1 | 3/2014 |
| WO | WO 2014/078257 A1 | 5/2014 |
| WO | WO 2014/095775 A1 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/202578 A1 | 12/2014 |
| WO | WO 2015/002754 A2 | 1/2015 |
| WO | WO 2015/004533 A2 | 1/2015 |
| WO | WO 2015/004534 A2 | 1/2015 |
| WO | WO 2015/011084 A1 | 1/2015 |
| WO | WO 2015/013635 A2 | 1/2015 |
| WO | WO 2015/015318 A2 | 2/2015 |
| WO | WO 2015/025226 A2 | 2/2015 |
| WO | WO 2015/025228 A2 | 2/2015 |

OTHER PUBLICATIONS

Abdul-Rahman et al., "Dinuclear Molybdenum complexes derived from diphenols: electrochemical interactions and reduced species" *Polyhedron* 16(24):4353-4362 (1997).

Acton et al., "Identification of Scavenger Receptor SR-BI as a High Denisty Lipoprotein Receptor" *Science* 271:518-520 (1996).

Aiello, R.J., et al., "Monocyte chemoattractant protein-1 accelerates atherosclerosis in apolipoprotein E-deficeint mice" *Arterioscler Thromb. Vasc. Biol.* 19(6): 1518-25 (1999).

(56) References Cited

OTHER PUBLICATIONS

Alexandraki, K. et al., "Inflammatory process in type 2 diabetes: The role of cytokines" *Ann N Y Acad Sci*, 2006. 1084:89-117.

Ambinter, "2(1H)-Pyridone, 1-[(4-chlorophenyl)methyl]-5-(1,3,4-oxadiazol-2-yl)-" Chemical Abstracts Record No. 120999-95-0 [online], entered int0 STN Registry File Mar. 15, 2010.

Andersson, "Pharmacology of apolipoprotein A-I" *Curr. Opin. Lipidol.* 8:225-228 (1997).

Antonelli, A. et al., "Serum levels of proinflammatory cytokines interleukin-1beta, interleukin-6, and tumor necrosis factor alpha in mixed cryoglobulinemia" *Arthritis Rheum*, 2009. 60(12):3841-7.

Aricha, R. et al., "Blocking of IL-6 suppresses experimental autoimmune myasthenia gravis" *J Autoimmun*, 2011, 36(2):135-41.

Arif, M. et al., "Protein lysine acetylation in cellular function and its role in cancer manifestation" *Biochim Biophys Acta*, 2010, 1799(10-12):702-16.

Ash, Z. and P. Emery, "The role of tocilizumab in the management of rheumatoid arthritis" *Expert Opin Biol Ther.* 2012, 12(9): 1277-89.

Asztalos, "High-Density Lipoprotein Metabolism and Progession of Atherosclerosis: New Insights from the HDL Atherosclerosis Treatment Study" *Curr. Opin. Cardiol.* 19:385-391 (2004).

Avicel PH, product informatom from FMC, downloaded from http://www.fmcbiopolymer.com/Portals/Pharm/Content/Docs.pdf on Aug. 15, 2013 (2 pages).

Baba et al., "Continuous intake of polyphenolic compounds containing cocoa powder reduces LDL oxidative susceptibility and has benefical effects on plasma HDL-cholesterol concentrations in humans" *Am. J. Clin. Nutr.* 85:709-717 (2007).

Badimon et al. "Regression of Atherosclerotic Lesions by High Density Lipoprotein Plasma Fraction in the Cholesterol-fed Rabbit" *J. Clin. Invest.* 85: 1234-1241 (1990).

Badimon et al., "Role of High Density Lipoproteins in the Regression of Atherosclerosis" *Circulation* 86(Suppl. III):86-94 (1992).

Bagul et al., "Current Status of Tablet Disintegrants: A Review" Online: http://www.pharmainfo.net/reviews/current-status-tablet-disintegrantsa-review, 2006, 16 pages.

Bandukwala, H.S. et al., "Selective inhibition of CD4+ T-cell cytokine production and autoimmunity by BET protein and c-Myc inhibitors" *Proc Natl Acad Sci USA*, 2012. 109(36):14532-7.

Bandyopadhyay, K. et al., "Spermidinyl-CoA-based HAT inhibitors block DNA repair and provide cancer-specific chemo- and radiosensitization" *Cell Cycle*, 2009, 8(17):2779-88. (Author's manuscript, 19 pages).

Banerjee, C. et al., "BET bromodomain inhibition as a novel strategy for reactivation of HIV-1" *J Leukoc Biol*, 2012. 92(6):1147-54.

Baron, P. et al., "Production of IL-6 by human myoblasts stimulated with Abeta: relevance in the pathogenesis of IBM" *Neurology*, 2001, 57(9):1561-5.

Barrans et al., "Pre-β HDL: Structure and Metabolism" *Biochem. Biophys. Acta* 1300:73-85 (1996).

Barter et al., "Antiinflammatory Properties of HDL" *Circ. Res.* 95:764-772 (2004).

Barter et al., "High density Lipoproteins and Coronary Heart Disease" *Atherosclerosis* 121:1-12 (1996).

Bartholomeeusen, K. et al., "BET bromodomain inhibition activates transcription via a transient release of P-TEFb from 7SK snRNP" JBC In Press, 2012, M112.410746, 16 pages. Final publication in: *J Biol Chem*, 287,38609-16.

Bassiouny, D.A. and O. Shaker, "Role of interleukin-17 in the pathogenesis of vitiligo" *Clin Exp Dermatol*, 2011.36(3):292-7.

Bayly et al., "Electronic and magnetic metal-metal interactions in dinuclear oxomolybdenum(V) complexes across bis-phenolate bridging ligands with different spacers between the phenolate termini: ligand-centered vs. metal-centered redox activity" *J. Chem. Soc., Dalton Transactions* 9:1401-1414 (2001).

Bayraktaroğlu, T. et al., "Serum levels of tumor necrosis factor-alpha, interleukin-6 and interleukin-8 are not increased in dyspeptic patients with Helicobacter pylori-associated gastritis" *Mediators Inflamm*, 2004. 13(1):25-8.

Belanger, D.B. et al., "Discovery of imidazo[1,2-a]pyrazine-based Aurora kinase inhibitors" *Bioorg. Med. Chem. Lett.*, 20:5170-5174 (2010).

Belkina, A.C. and G.V. Denis, "BET domain co-regulators in obesity, inflammation and cancer" *Nat Rev Cancer*, 2012. 12(7):465.-77.

Bellan, C. et al., "CDK9/CYCLIN T1 expression during normal lymphoid differentiation and malignant transformation" J. Pathol., 2004. 203(4):946-52.

Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.

Berkovits, B.D. et al., "The testis-specific double bromodomain-containing protein BRDT forms a complex with multiple spliceosome components and is required for mRNA splicing and 3'-UTR truncationin round spermatids" *Nucleic Acids Res*, 2012. 40(15):7162-75.

Bertele et al., "Platelet Thromboxane Synthetase Inhibitors with Low Doses of Aspirin: Possible Resolution of the 'Aspirin Dilemma'" *Science* 220:517-519 (1983).

Besnard, A.G. et al., "Inflammasorne-IL-1-Th17 response in allergic lung inflammation" *J Mol Cell Biol*, 2012. 4(1):3-10.

Beugelmans et al., "One-pot Synthesis of 1-Oxo-1,2-Dihydroisoquinolines (Isocarbostyrils) Via $S_{RN}1$ (Ar) Reactions" *Synthesis* 9:729-731 (1981).

Bhilare et al., "Ionic-Liquid-Influenced Expeditious and Stereoselective Synthesis of Olefins" *Synthetic Communications* 37(18):3111-3117 (2007).

Bisagni et al., "A Convenient Way to Dibenzo[c,h]-1,5-Naphthyridines (11-Aza-Benzo[c]phenanathridines)" *Tetrahedron* 52:1427-10440 (1996).

Bisgaier et al., "A Novel Compound that Elevates High Density Lipoprotein and Activates the Peroxisome Proliferator Activated Receptor" *J. Lipid Res.* 39:17-30 (1998).

Boring, L. et al., "Decreased lesion formation in CCR2-/-mice reveals a role for chemokines in the initiation of atherosclerosis" *Nature*, 1998. 394(6696):894-7.

Boyce et al., "The Acylation and Alkylation of o-Tolunitrile. A New Route to 3-Substituted Isocarbostyrils" *J. Org. Chem.* 31:3807-3809 (1966).

Bradley, D.T. and S.E. Kountakis, "Role of interleukins and transforming growth factor-beta in chronic rhinosinusitis and nasal polyposis" *Laryngoscope*, 2005. 115(4):684-6.

Bradsher et al., "A New Isoquinoline Synthesis Via ORTHO-Substituted Benzylamines" *Tetrahedron Lett*, 31:3149-3150 (1972).

Bradsher et al., "α-Acyl-o-Tolunitriles as Intermediates in the Preparation of 3-Substituted Isoquinolines and 1-Amino-2-benzopyrylium Derivatives" *J. Org. Chem.* 43:3817-3820 (1978).

Brodmerkel, C.M. et al., "Discovery and pharmacological characterization of a novel rodent-active CCR2 antagonist, INCB3344" *J Immunol*, 2005. 175(8):5370-8.

Brühl, H. et al., "Dual role of CCR2 during initiation and progression of collagen-induced arthritis: evidence for regulatory activity of CCR2+ T cells" *J Immunol*, 2004. 172(2):890-8.

Buhle et al., "Trivalent Carbon. II. Unsymmetrical Hexaaryldimethylperoxides" *J. Am. Chem. Soc.* 65:584-586 (1943).

CAPLUS Accession No. 1991:4494853, Liu et al. "Synthesis of 2-aryl-9-bromo-4-oxo-4H-pyrano[3,2-c] quinolines" [online]. Retrieved from STN on Jan. 31, 2011. Also published in: *Youji Huaxue* 11(2):191-195 (1991).

CAPLUS Accession No. 2003:554477, Qin et al., "Synthesis and fungicidal activity of novel diazaflavanones" [online]. Retrieved from STN on Jan. 31, 2011, Also published in: *Nongyaoxue Xuebao* 4(4):28-32 (2002).

CAPLUS Accession No. 2004:11346, Hu et al., "Synthesis and fungicidal activity of flavanone derivaties containing isopentenyl group" [online]. Retrieved from STN on Jan. 31, 2011. Also published in: *Yingyong Huaxue* 20(12):1161-1165 (2003).

CAPLUS Accession No. 2005:46491, Qin et al., "Synthesis and fungicidal activity of 5,7-dihydroxyldiazinflavanones" [online]. Retrieved from STN on Jan. 31, 2011. Also published in: *Huazhong Shifan Daxue Xuebao Zirankexueban* 38(3):323-325 (2004).

(56) References Cited

OTHER PUBLICATIONS

Chakrabarty et al., "Induction of apoptosis in human cancer cell lines by diospyrin, a plant-derived bisnaphthoquinonoid, and its synthetic derivated" *Cancer Letters* 188(1-2):85-93 (2002).

Chartier et al., "Synthese de diazaflavones" *Bull. Soc. Chim. Fr.* 11-12(Pt.2):1816-1918 (1976). English astract on p. 1916.

Chen. L. et al., "IL-17RA aptamer-mediated repression of IL-6 inhibits synovium inflammation in a murine model of osteoarthritis" *Osteoarthritis Cartilage*, 2011. 19(6):711-8.

Cherubini et al., "Role of Antioxidants in Atherosclerosis: Epidemiological and Clinical Update" *Curr. Pharm. Des.* 11:2017-2032 (2005).

Chevrel, G. et al., "Interleukin-17 increases the effects of IL-1 beta on muscle cells: arguments for the role of T cells in the pathogenesis of myositis" *J Neuroimmunol*, 2003. 137(1-2):125-33.

Cho et al., "Molecular Modeling of 3-Arylisoquinoline Antitumor Agents Active Against A-549. A Comparative Molecular Field Analysis Study" *Bioorg. Med. Chem.* 10:2953-2961 (2002).

Cho et al., "Synthesis and Antitumor Activity of 3-Arylisoquinoline Derivaives" *Arch. Pharm. Res.* 20:264-268 (1997).

Cho et al., "Synthesis and Biological Evaluation of 3-Arylisoquinolines as Antitumor Agents" *Bioorg. Med. Chem. Lett.* 8:41-46 (1998).

Cho et al., "Synthesis and Comparative Molecular Field Analysis (CoMFA) of Antitumor 3-Arylisoquinoline Derivatives" *Bioorg. Med. Chem.* 6(12):2449-2458 (1998).

Chung, C.W., et al., "Discovery and characterization of small molecule inhibitors of the BET family bromodomains" *J Med Chem*, 2011. 54(11):3827-38.

Chung, C.W., "Small Molecule Bromodomain Inhibitors: Extending the Druggable Genome" *Progr. Med. Chem.*, 51:1-55 (2012).

Chyu et al., "Differential Effects of Green Tea-Derived Catechin on Developing Versus Established Atherosclerosis in Apolipoprotein E-Null Mice" *Circulation* 109:2448-2453 (2004).

Cid, J.M. et al., "Discovery of 1,5-Disubstituted Pyridones: A New Class of Positive Allosteric Modulators of the Metabotropic Glutamate 2 Receptor" *ACS Chem. Neurosci.* 1:788-795 (2010).

Clarkson et al., "Inhibition of Postmenopausal Atherosclerosis Progression: A Comparison of the Effects of Conjugated Equine Estrogens and Soy Phytoestrogens" *J. Clin Endocrinol. Metab.* 86(1):41-47 (2001).

Clauson-Kaas et al., "Reactions of 3,4-dihydor-2H-pyrrido[3,2-b]-1,4-oxazine" *Acta Chemica Scandinavica* 25(8):3135-3143 (1971), Retrieved from STN, file HCAPLUS, Accession No. 1972:34186 (Abstract).

Connolly et al., "Synthesis of quinazolinones and quinazolines" *Tertrahedron* 61(43):10153-10202 (2005).

Cooper et al., "Wine polyphenois and promotion of cardiac health" *Nutr. Res. Rev.* 17:111-129 (2004).

Costello, J.F. et al., "Cyclin-dependent kinase 6 (CDK6) amplification in human gliomas identifies using two-dimensional separation of genomic DNA" *Cancer Res*, 1997, 57(7):1250-4.

Cramer et al., "New Syntheses of Aryl Fluorides and Aryl Fluorosulfonates from Oxyflourides of Sulfur" *J. Org. Chem.* 26:4164-4165 (1961).

Dai et al., "Synthesis of 3,4-Disubstituted Isoquinolines via Palladium-Catalyzed Cross-Coupling of 2-(1-alkynyl)benzaldimines and Organic Halides" *J. Org. Chem.* 68:920-928 (2003).

Dai et al., "Synthesis of 3-Substituted 4-Aroylisoquinolines via Pd-Catalyzed Carbonylative Cyclization of 2-(1-Alkynyl)benzaldimines" *J. Org. Chem*, 67:7042-7047 (2002).

Dansky et al., "High-Density Lipoprotein and Plaque Regression. The Good Cholesterol Gets Even Better" *Circulation* 100:1762-1763 (1999).

D'Auria, L. et al., "Cytokines and bullous pemphigoid" *Eur Cytokine Netw*, 1999. 10(2):123-34.

Dawson, J. et al., "Targeting monocyte chemoattractant protein-1 signalling in disease" *Expert Opin Ther Targets*, 2003. 7(1):35-48.

Dawson, M.A. et al., "Inhibition of BET Recruitment to Chromatin as as Effective Treatment for MLL-fusion Leukaemia", *Nature*, 2011, 478:529-533.

De Falco, G. et al., "Cdk9 regulates neural differentiation and its expression correlates with the differentiation grade of neuroblastoma and PNET tumors" *Cancer Biol Ther*, 2005. 4(3):277-81.

De Lemos, J.A. et al., "Association between plasma levels of monocyte chemoattractant protein-1 and long-term clinical outcomes in patients with acute coronary syndromes" *Circulation*, 2003. 107(5):690-5.

De Paiva, C.S. et al., "1L-17 disrupts corneal barrier following desiccating stress" *Mucosal Immunol*, 2009. 2(3):243-53.

Decossin et al., "Subclasses of LpA-I in Coronary Artery Disease: Distribution and Cholesterol Efflux Ability" *Eur. J. Clin. Invest.* 27:299-307 (1997).

DeGoma, E.M. and D.J. Rader, "Novel HDL-directed pharmacotherapeutic strategies" *Nat Rev Cardiol*, 2011. 8(5):266-77.

Delmore, J.E. et al., "BET bromodomain inhibition as a therapeutic strategy to target c-Myc" *Cell*, 2011. 146(6):904-17.

Deng, J. et al., "Th17 and Th1 T-cell responses in giant cell arteritis" *Circulation*, 2010. 121(7):906-15.

Denis, G.V. et al., "An emerging role for bromodomain-containing proteins in chromatin regulation and transcriptional control of adipogenesis" *FEBS Lett*, 2010. 584(15):3260-8. (Author manuscript, 21 pages).

Denis, G.V., "Bromodomain coactivators in cancer, obesity, type 2 diabetes, and inflammation" *Discov Med*, 2010. 10(55):489-99.

Deo, R. et al., "Association among plasma levels of monocyte chemoattractant protein-1, traditional cardiovascular risk factors, and subclinical atherosclerosis" *J Am Coll Cardiol*, 2004. 44(9): p. 1812-8.

Devitt et al., "Synthesis of Heterocyclic-Substituted Chromones and Chalcones" *J. Org. Chem.* 26: 4941-4944 (1961).

Dias, P.M. and G. Banerjee, "The Role of Th17/IL-17 on Eosinophilic Inflammation" *J. Autoimnun*, 2012. Article in Press: http://dx.doi.org/10.1016/j.jaut.2012.07.004, 12 pages Edwards et al., "Inhibition of myeloperoxidase release from rat polymorphonuclear leukocytes by a series of azachalcone derivatives" *J. Med. Chem.* 37(25):4357-4362 (1994).

Eiden et al., "1,2-Bisbenzopyranyl-ethene" *Archiv. der Pharmazie* 313(2):120-128 (1980) (German). English abstract on p. 120.

Elliott, D.A. et al., "Apolipoproteins in the brain: Implications for neurological and psychiatric disorders" *Clin Lipidol*, 2010. 51(4):555-573. (Author manuscript, 28 pages).

El-Osta, H.E. and R. Kurzrock, "Castleman's disease: from basic mechanisms to molecular therapeutics" *Oncologist*, 2011. 16(4):497-511.

Esterbauer et al., "Continuous Monitoring of In Vitro Oxidation of Human Low Density Lipoprotein" *Free Rad. Res. Comms.* 6:67-75 (1989).

Ferreira et al., "Diversity of Structure and Function in Oligomeric Flavanoids" *Tetrahedron* 48:1743-1803 (1992).

Fielding et al., "Molecular Physiology of Reverse Cholesterol Transport" *J. Lipid Res.* 36:211-228 (1995).

Fieser, L.F., "The potentials of some unstable oxidation-reduction systems" *J. Am. Chem. Soc.* 52:4915-4940 (1930).

Fife, B.T. et al., "CC chemokine receptor 2 is critical for induction of experimental autoimmune encephalomyelitis" *J Exp Med*, 2000. 192(6):899-905.

Figueroa-Vega, N. et al., "Increased circulating pro-inflammatory cytokines and Th17 lymphocytes in Hashimoto's thyroiditis" *J Clin Endocrinol Metab*, 2010. 95(2):953-62.

Filippakopoulos, Panagis et al., "Selective Inhibition of BET Bromodomains", *Nature*, 2010, 468:1067-1073.

Fish, P.V. et al., "Identification of a chemical probe for bromo and extra C-terminal bromodomain inhibition through optimization of a fragment derived hit" *J. Med. Chem.* 55:9831-9837 (2012).

Fisher Center for Alzheimer's Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from

(56) References Cited

OTHER PUBLICATIONS the Internet: http://www.alzinfo.org/newsarticle/templates/archivenewstemplate.asp?articleid=156&zoneid=7 on Jul. 26, 2010 (3 pages).
Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French). English abstract on p. 361.
Fokialakis et al., "A New Class of Phytoestrogens: Evaluation of the Estrogenic Activity of Deoxybenzoins" *Chem. Biol.* 11:397-406 (2004).
French, C.A., "NUT midline carcinoma" *Cancer Genet Cytogenet*, 2010. 203(1):16-20, (Author manuscript, 9 pages).
Fujioka, A. et al., "The analysis of mRNA expression of cytokines from skin lesions in Churg-Strauss syndrome" *J Dermatol*, 1998. 25(3):171-7.
Fujishima, S. et al., "Involvement of IL-17F via the induction of IL-6 in psoriasis" *Arch Dermatol Res*, 2010. 302(7):499-505.
Gagnon, D. et al., "Proteasomal degradation of the papillomavirus E2 protein is inhibited by overexpression of bromodomain-containing protein 4" *J Virol*, 2009. 83(9):4127-39.
Gaucher, J. et al., "Bromodomain-dependent stage-specific male genome programming by Brdt" *EMBO J*, 2012. 31(19):3809-20.
Gaziano et al., "Relation Between Systemic Hypertension and Blood Lipids on the Risk of Myocardial Infarction" *J. Cardiol.* 84(7):768-773 (1999).
Gerritsen et al., "Flavenoids inhibit cytokine-induced endothelial cell adhesion protein gene expression" *Am. J. Pathol.* 147(2):278-292 (1995).
Gidez et al., "Separation and Quantitation of Subclasses of Human Plasma High Density Lipoproteins by a Simple Precipitation Procedure" *J. Lipid Res.* 23:1206-1223 (1982).
Gloddek, B. et al., "Pharmacological influence on inner ear endothelial cells in relation to the pathogenesis of sensorineural hearing loss" *Adv Otorhinolaryngol*, 2002. 59:75-83.
Gong, J-H. et al., "An antagonist of monocyte chemoattractant protein 1 (MCP-1) inhibits arthritis in the MRL-lpr mouse model" *J Exp Med*, 1997, 186(1):131-7.
Gong, J-H. et al., "Post-onset inhibition of murine arthritis using combined chemokine antagonist therapy" *Rheumatology*, 2004. 43(1):39-42.
González-Serrano, M.E. et al., "Increased Pro-inflammatory Cytokine Production After Lipopolysaccharide Stimulation in Patients with X-linked Agammaglobulinemia" *J Clin Immunol*, 2012. 32(5):967-74.
Gordon et al., "High Density Lipoprotein as a Protective Factor Against Coronary Heart Disease" *Am. J. Med.* 62(5):707-714 (1977).
Gosling, J. et al., "MCP-1 deficiency reduces susceptibility to atherosclerosis in mice that overexpress human apolipoprotein B" *J Clin Invest*, 1999. 103(6):773-8.
Graber, J.J. et al., "Interleukin-17 in transverse myelitis and multiple sclerosis" *J Neuroimmunol*, 2008. 196(1-2):124-32.
Greenwald, R.J. et al., "E mμ-BRD2 transgenic mice develop B-cell lymphoma and leukemia" *Blood*, 2004, 103(4):1475-84.
Grundy et al., "Definition of Metabolic Syndrome. Report of the National Heart, Lung and Blood Institute/American Heart Association Conference on Scientific Issues Related to Definition" *Circulation* 109:433-438 (2004).
Grunwald, C. et al., "Expression of multiple epigenetically regulated cancer/germline genes in nonsmall cell lung cancer" *Int J Cancer*, 2006. 118(10):2522-8.
Gu, L. et al., "Absence of monocyte chemoattractant protein-1 reduces atherosclerosis in low density lipoprotein receptor-deficient mice" *Mol Cell*, 1998. 2(2):275-81.
Gu, Y. et al., "Interleukin (IL)-17 promotes macrophages to produce IL-8, IL-6 and tumour necrosis factor-alpha in aplastic anaemia" *Br J Haematol*, 2008. 142(1):109-14.
Gugler et al., "Disposition of Quercetin in Man after Single Oral and Intravenous Doses" *Eur. J. Clin. Pharmacol.* 9:229-234 (1975).

Guillory, J.K., "Generation of Polymorphs, Hydrates, Solvates, and Amorphous Solids" Brittain, Harry G. (ed.) *Polymorphism in Pharmaceutical Solids*, vol. 95, Marcel Dekker, Inc., New York; pp. 202-208 (1999).
Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).
Haneke, "*trans*-Resveratrol, [501-36-0], Review of Toxicological Literature" Nat. Inst. Environ. Health Sciences Contract No. N01-ES-65402 (Mar. 2002).
Harada, K. et al., "Periductal interleukin-17 production in association with biliary innate immunity contributes to the pathogenesis of cholangiopathy in primary billary cirrhosis" *Clin Exp Immunol*, 2009. 157(2):261-70.
Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest Ophthalmol Vis Sci*, 2011. 52(6):3264-71.
Hay, D.A. et al., "Discovery and Optimization of Small-Molecule Ligands for the CBP/p300 Bromodomains" *J. Am. Chem. Soc.* 136:9308-9319 (2014).
Hazra et al., "New diospyrin derivatives with improved tumor inhibitory activity towards Ehrlich ascites carcinoma" *Medical Science Research* 22(5):351-353 (1994).
Hazra et al., "Synthesis of an antitumor derivative of diospyrin" *IRCS Medical Science* 14(1):35-36 (1986).
Heeg et al., "Plasma Levels of Probucol in Man after Single and Repeated Oral Doses" *La Nouvelle Presse Medicale* 9:2990-2994 (1980). English abstract on p. 2990.
Hemingway et al., "A gas-liquid chromatographic examination of stilbene derivatives" *J. Chromatog.* 50(3):391-399 (1970).
Hertog et al., "Dietary Antioxidant Flavonoids and Risk of Coronary Heart Disease: the Zutphen Elderly Study" *Lancet* 342:1007-1011 (1993).
Hewings et al., "Progress in the development and application of small molecule inhibitors of bromodomain-acetyl-lysine interactions" *J. Med. Chem.* 55:9393-9413 (2012).
Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).
Hirano et al., "Genetic Cholestery Ester Transfer Protein Deficiency is Extremely Frequent in the Omagari Area of Japan. Marked Hyperalphalipoproteinemia Caused by CETP Gene Mutation Is Not Associated With Longevity" *Arterioscle Thromb Vasc. Biol.* 17:1053-1059 (1997).
Hisano et al., "Studies on Organosulfur Compounds. XII, Syntheses and Pharmacological Activities of 2-Heterocyclic Substituted 4(3H)-Quinazolinones" *Chem. Pharm. Bull.* 23(9):1910-1916 (1975).
Hohki, S. et al., "Blockade of interleukin-6 signaling suppresses experimental autoimmune uveoretinitis by the inhibition of inflammatory Th17 responses" *Exp Eye Res*, 2010, 91(2):162-70
Hölttä, V. et al., "IL-23/IL-17 immunity as hallmark of Crohn's disease" *Inflamm Bowel Dis*, 2008. 14(9):1175-84.
Hoshino, I. and H. Matsubara, "Recent advances in histone deacetylase targeted cancer therapy" *Surg Today*, 2010. 40(9):809-15.
Huang et al., "Synthesis of Isoquinolines by Palladium-Catalyzed Cyclization, Followed by a Heck Reaction" *Tetrahedron Lett.* 43:3557-3560 (2002).
Huang, D. et al., "Absence of monocyte chemoattractant protein 1 in mice leads to decreased local macrophage recruitment and antigen-specific T helper cell type 1 immune aresponse in experimentalautoimmune encephalomyelitis" *J Exp. Med*, 2001. 193(6):713-26.
Hwang et al., "Syntergistic inhibition of LDL oxidation by phytoestrogens and ascorbic acid" *Free Radical Biology and Medicine* 29(1):79-89 (Jul. 1, 2000).
Içoz, S. et al., "Enhanced IL-6 production in aquaporin-4 antibody positive neuromyelitis optica patients" *Int J Neurosci*, 2010. 120(1):71-5.

(56) References Cited

OTHER PUBLICATIONS

International Search Report and Written Opinion issued in International Application No. PCT/CA2004/001818; Date of Mailing: Feb. 28, 2005.
International Search Report and Written Opinion issued in International Application No. PCT/CA2007/000146; Date of Mailing: Oct. 29, 2007.
International Search Report and Written Opinion issued in International Application No. PCT/IB2010/000159; Date of Mailing: Aug. 5. 2010.
International Search Report and Written Opinion issued in International Application No. PCT/IB2010/000826; Date of Mailing: Oct. 12. 2010.
International Search Report and Written Opinion issued in international Application No. PCT/IB2012/002721; Date of Mailing: Mar. 14, 2013.
International Search Report and Written Opinion issued in International Application No. PCT/IB2013/000968; Date of Mailing: Sep. 13, 2013.
International Search Report and Written Opinion issued in International Application No. PCT/IB2013/001026: Date of Mailing: Sep. 30, 2013.
International Search Report and Written Opinion issued in International Application no. PCT/IB2013/001232; Date of Mailing: Sep. 6, 2013.
International Search Report and Written Opinion issued in International Application No. PCT/IB2013/003031; Date of Mailing: May 28, 2014.
International Search Report and Written Opinion issued in International Application No. PCT/IB2013/003122: Date of Mailing: Jul. 9, 2014.
International Search Report and Written Opinion issued in International Application No. PCT/IB2013/003126; Date of Mailing: Jun. 26, 2014.
International Search Report and Written Opinion issued in International Application No. PCT/IB2013/003202: Date of Mailing: Jul. 17 2014.
International Search Report and Written Opinion issued in International Application No. PCT/IB2014/002238; Date of Mailing: Apr. 23, 2015.
International Search Report and Written Opinion issued in international Application No. PCT/US2005/037719; Date of Mailing: Mar. 9, 2007.
International Search Report and Written Opinion issued in International Application No, PCT/US2009/048457; Date of Mailing: Oct. 16, 2009.
International Search Report and Written Opinion issued in International Application No. PCT/US2010/031870: Date of Mailing: Jul. 1, 2010.
International Search Report and Written Opinion issued in International Application No. PCT/IB2014/002240; Date of Mailing: Mar. 10, 2015.
International Search Report and Written Opinion issued in International Application No. PCT/IB2014/002546; Date of Mailing: Mar. 13, 2015.
International Search Report and Written Opinion issued in International Application No. PCT/IB2015/002560; Date of Mailing: Mar. 19, 2015.
Ishibashi et al., "Hypercholesterolemia in Low Density Lipoprotein Receptor Knockout Mice and Its Reversal by Adenovirus-Mediated Gene Delivery" *J. Clin. Invest.* 92:883-893 (1993).
Ishibashi et al., "Massive Xanthomatosis and Atherosclerosis in Cholesterol-Fed Low Density Lipoprotein Receptor-Negative Mice" *J. Clin Invest.* 93:1885-1893 (1994).
Ishizu, T. et al., "CSF cytokine and chemokine profiles in acute disseminated encephalomyelitis" *J Neuroimmunol*, 2006, 175(1-2):52-8.
Ito, Y. et al., "Pathogenic significance of interleukin-6 in a patient with antiglomerular basement membrane antibody-induced glomerulonephritis with multinucleated giant cells"*Am J Kidney Dis*, 1995. 26(1):72-9.
Jadidi-Niaragh, F. and A. Mirshafley, "Th17 cell, the new player of neuroinflammatory process in multiple sclerosis" *Scand J Immunol*, 2011. 74(1):1-13.
Jahagirdar, R. et al.. "An Orally Bioavailable Small Molecule RVX-297 Significantly Decreases Disease in a Mouse Modelof Multiple Sclerosis" (Poster Presentation). World Congress of Inflammation, Paris, France, 2011. 1 page.
Jayatilake et al., "Kinase Inhibitors From *Polygonum cuspidatum* " *J. Nat. Prod.* 56:1805-1810 (1993).
Jen, H-Y. et al., "Increased serum interleukin-17 and peripheral Th17 cells in children with acute Henoch-Schonlein purpura" *Pediatr Allergy Immunol*, 2011. 22(8):862-8.
Jensen et al., "Serum Lipids and Anthropometric Factors Related to the Prevalence of Intermittent Claudication" *Eur. J. Vasc. Endovasc. Surg.* 30:562-587 (2005).
Jeong et al., "Hypocholesterolemic activity of hesperetin derivatives" *Bioorg. Med. Chem. Lett.* 13:2663-2665 (2003).
Jia, S., et al., "The T helper type 17/regulatory T cell Imbalance in patients with acute Kawasaki disease" *Clin Exp Immunol*, 2010. 162(1):131-7.
Jin et al., "Antiplatelet and antithrombotic activities of CP201, a newly synthesized 1,4-naphthoquinone derivative" *Vasc. Pharmacol.* 41(1):35-41 (2004).
Johnson, R.B. et al., "Interleukin-11 and IL-17 and the pathogenesis of periodontal disease" *J Periodontol*, 2004. 75(1):37-43.
Kahawita, I.P. and D.N. Lockwood. "Towards understanding the pathology of erythema nodosum leprosum" *Trans R Soc Trop Med Hyg*, 2008. 102(4):329-37.
Kallen, K.J. et al., "New developments in IL-6 dependent biology and therapy: where do we stand and what are the options?" *Expert Opin Investig Drugs*, 1999, 8(9):1327-49.
Kalusa et al., "An efficient synthesis of 2,3-diaryl (3H)-quinazolin-4-ones via imidoyl chlorides" *Tetrahedron Letters* 49(41):5840-5842 (2008).
Kaplanski, G. et al., "Jarisch-Herxheimer reaction complicating the treatment of chronic Q fever endocarditis: elevated TNFalpha and 1L-6 serum levels" *J Infect*, 1998. 37(1):83-4.
Kappel, L.W. et al., "IL-17 contributes to CD4-mediated graft-versus-host disease" *Blood*, 2009. 113(4):945-52.
Katsifis, G.E. et al., "Systemic and local interleukin-17 and linked cytokines associated with Sjogren's syndrome immunopathogenesis" *Am J Pethol*, 2009. 175(3)-1167-77.
Kawai, M. et al., "Sustained response to tocilizumab, anti-interleukin-6 receptor antibody, in two patients with refractory relapsing polychondritis" *Rheumatology*, 2009. 48(3):318-9.
Kawakami, T. et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis" *Am J Gastroenterol*, 2009. 104(9):2363-4.
Kawakami, T. et al., "Serum Levels of interleukin-6 in patients with cutaneous polyarteritis nodosa" *Acta Derm Venereol*, 2012. 39(3):322-3.
Kawamatsu et al., "2-Amino-4-Phenylthiazole Derivatives as Anti-Atherogenic Agents" *Eur. J. Med. Chem.—Chimica Therapeutica* 16(4):355-362 (1961).
Kelly, P.N. and A. Strasser, "The role of Bcl-2 and its pro-survival relatives in tumourigenesis and cancer therapy" *Cell Death Differ*, 2011. 18(9)1414-24.
Kilbourne et al., "Involvement of Early Growth Response Factor Egr-1 in Apolipoprotein AI Gene Transcription" *J. Biol. Chem.* 270:7004-7010 (1995).
Kim et al., "Hypothetical Drug Binding Receptor Site Analysis Using CoMFA Method for 3-Arylisoquinolines Active Against SK-OV-3 Tumor Cell Line" *Yakhak Hoechi* 46(4):219-225 (2002). English abstract on p. 219.
Kim, S.E. et al., "Increased serum interleukin-17 in Graves' opthalmopathy" *Graefes Arch Clin Exp Ophthalmol*, 2012. 250(10):1521-6.

(56) References Cited

OTHER PUBLICATIONS

Kimura, A. and T. Kishimoto, "IL-6: regulator of Treg/Th17 balance" *Eur J Immunol*, 2010. 40(7):1830-5.
Koch, A.E. et al., "Enhanced production of monocyte chemoattractant protein-1 in rheumatoid arthritis" *J Clin Invest*, 1992, 90(3):772-9.
Koudinov et al., "Alzheimer's amyloid beta and lipid metabolism link?" *FASEB J.* 12:1097-1099 (1998).
Kublak et al., "The preparation of the aza-spirobicyclic system of discorhabdin C via an intramolecular phenolate alkylation" *Tetrahedron Lett.* 31(27):3845-3848 (1990).
Kulkarni et al., "Quantification of $HDL_2$ and $HDL_3$ Cholesterol by the Vertical Auto Profile-II (VAP-II) Methodology" *J. Lipid Res.* 38:2353-2364 (1997).
Kurata et al., "A Candidate High Density Lipoprotein (HDL) Receptor, $HB_2$, with Possible Multiple Functions Shows Sequence Homology with Adhesion Molecules" *J. Atherosler. Thromb.* 4:112-117 (1996).
Kurowska et al., "Essential Amino Adds in Relation to Hypercholesterolemla Induced in Rabbits by Dietary Casein" *J. Nutr.* 120:831-836 (1990).
Kuzuya et al., "Probucol Prevents Oxidative Injury to Endothelial Cells" *J. Lipid Res.* 32:197-204 (1991).
Kyburz, D. and M. Corr, "Th17 cells generated in the absence of TGF-beta Induce experimental allergic encephalitis upon adoptive transfer" *Expert Rev Clin Immunol*, 2011. 7(3):283-5.
Laarhoven et al., "Syntheses, infrared spectra and molecular refractions of some sterically hindered p,p'-dimethoxystilbenes. Influence of non-planarity in styrene and stilbene derivatives IV" *Recueil des Travaux Chimiques des Pays-Bas* 80:775-791 (1961).
LaGrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).
Lahdenperä, A.I. et al, "Up-regulation of small intestinal interleukin-17 immunity in untreated coeliac disease but not in potential coeliac disease or in type 1 diabetes" *Ciin Exp Immunol*, 2012.167(2):226-34.
Lamale, L.M. et al., "Interleukin-6, histamine, and methylhistamine as diagnostic markers for interstitial cystitis" *Urology*, 2006. 68(4):702-6.
Lamon-Fava, "Genistein activates apolipoprotein A-I gene expression in the human hepatoma cell line Hep G2" *J. Nutrition* 130:2489-2492 (2000).
Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi: 10.1016/j.bmcl.2012.02.041, Final publication as: Seal, J. et al., "Identification of a novel series of BET family bromodomain inhibitors: binding mode and profile of I-BET151 (GSK1210151A)" *Bioorg Med Chem Lett*, 2012, 22(8):2968-72.
Landshulz, et al., "Regulation of Scavenger Receptor, Class B, Type I, a High Density Lipoprotein Receptor, in Liver and Steroidogenic Tissues of the Rat" *J. Clin. Invest.* 98:984-995 (1996).
Latifi, S.Q. et al., "Persistent elevation of serum interleukin-6 in intraabdominal sepsis identifies those with prolonged length of stay" *J Pediatr Surg*, 2004. 39(10):1548-52.
Lee, D.K. et al., "Androgen receptor interacts with the positive elongation factor P-TEFb and enhances the efficiency of transcriptional elongation" *J Biol Chem*, 2001. 276(13):9978-84.
Letan, "The Relation of Structure to Antioxidant Activity of Quercetin and some of Its Derivatives. I. Primary Activity" *J. Food Sci.* 13(4):518-523 (1966).
Li, Z., et al., "The BET bromodomain inhibitor JQ1 activates HIV latency through antagonizing Brd4 inhibition of Tat-transactivation" *Nucleic Acids Res Advances Access*, 2012. DOI:10.1093/nar/gks976, 11 pages.
Lin et al., "Chemoprevention of Cancer and Cardiovascular Disease by Resveratrol" *Proc. Natl. Sci. Counc. ROC (B)* 23:99-106 (1999).

Lin et al., "Potential bioreductive alkylating agents. 7 Antitumor effects of phenyl-substituted 2-chloromethyl-3-phenyl-1,4-naphthoquinones" *J. Med. Chem.* 19(11):1336-1338 (1976).
Lin et al., "Solvent Effects on Az-Anionic Cycloaromatization of 2-(2-Substituted-Ethynyl)Benzonitriles" *J. Chinese Chem. Soc.* 46:211-214 (2001).
Lin et al., "The Role of Absorption, Distribution, Metabolism, Excretion and Toxicity in Drug Recovery" *Curr. Top. Med Chem.* 3:1125-1154 (2003).
Lin, F.J. et al., "Imbalance of regulatory T cells to Th17 cells in IgA nephropathy" *Scand J Clin Lab Invest*, 2012. 72(3):221-9.
Linhares, U.C. et al., "The Ex Vivo Production of IL-6 and IL-21 by CD4(+) T Cells is Directly Associated with Neurological Disability in Neuromyelitis Optica Patients" *J Clin Immunol*, 2012, DOI 10.1007/s10875-012-9780-2, 11 pages.
Linnell et al. "Isomers of stilbestrol. II." *Q. J. Pharm. Pharmacol.* 15:384-388 (1942).
Lopez et al., "The Synthesis of Substituted 2-Aryl-4(3H)-quinazolinones using $NaHSO_3$/DMA. Steric Effect Upon the Cyclisation-Dehydrogenation Step" *J. Chem. Research (S)*, pp. 258-259 (2000).
Lopez-Robles, E. et al., "TNFalpha and IL-6 are mediators in the blistering process of pemphigus" *Int J Dermatol*, 2001. 40(3):185-8.
Lu, M.O. and J. Zhu, "The role of cytokines in Guillain-Barre syndrome" *J Neurol*, 2011. 258(4):533-48.
Ma, D. et al., "Profile of Th17 cytokines (IL-17, TGF-beta, IL-6) and Th1 cytokine (IFN-gamma) in patients with immune thrombocytopenic purpura" *Ann Hematol*, 2008. 87(11):899-904.
Mahad, D.J. and R.M. Ransohoff, "The role of MCP-1 (CCL2) and CCR2 in multiple sclerosis and experimental autoimmune encephalomyelitis (EAE)" *Semin Immunol.* 2003. 15(1):23-32.
Maher et al., "Lipoprotein (a) and coronary heart disease" *Curr. Opin. Lipidol.* 6:229-235 (1995).
Mahto et al., "Synthesis of 3-Aryl-7-Hydroxy Isochromenes" *Asian J. Chem.* 11(2):431-435 (1999).
Manach et al., "Polyphenols and prevention of cardiovascular diseases" *Curr. Opin. Lipidol.* 16:77-84 (2005).
Marks, F., "Epidermal Growth Control Mechanisms, Hyperplasia, and Tumor Promotion in the Skin" *Cancer Res.* 36:2636-2343 (1976).
Martin et al., "Modified Flavinoids as Strong Photoprotecting UV-Absorbers and Antioxidants" Strategies for Safe Food. Eklund, T. et al. (Eds.), vol. 1, pp. 288-291 (2003).
Matzuk, M.M. et al., "Small-Molecule Inhibition of BRDT for Male Contraception" *Cell*, 2012. 150(4): 673-684 , with supplemental pp. S1-S8.
McKee et al., "Some Basically Substituted Quinazolines" *J. Am. Chem. Soc.* 68(10)1902-1903 (1946).
McKinley, L. et al., "TH17 cells mediate steroid-resistant airway inflammation and airway hyperresponsiveness in mice" *J Immunol*, 2008. 181(6):4089-97.
Meckes et al., "The effects of chrysin and pinostrobin, 2 flavonoids isolated from *Teloxys graveolens* leaves, on isolated guinea-pig ileum" *Phytomedicine* 5(6):459-463 (1996).
Melani et al., "Tricyclic heterocyclic systems: pyrazolo[5',4':4,5]- and pyrazolo-[3',4':4,5]pyrano[2,3-B]pyridine derivatives" *J. Heterocyclic Chem.* 25:1367-1371 (1988).
Mendrzyk, F. et al., "Genomic and protein expression profiling identifies CDK6 as novel Independent prognostic marker in medulloblastoma" *J Ckin Oncol*, 2005. 23(34):8853-62.
Mertz, Jennifer A., "Targeting MYC Dependence in Cancer by Inhibiting BET Bromodomains", *PNAS*, 2011, 108(40):16669-16674.
Middleton et al., "Quercetin inhibits lipopolysaccharide-induced expression of endothelial cell intracellular adhesion molecule-1" *Int. Arch. Allergy Immunol.* 107:435-436 (1995).
Mills, "Pharmaceutical excipients—an overview including considerations for paediatric dosing" Presented at the World Health Organization Training Workshop: Pharmaceutical Development with Focus on Paediatric Formulations, Beijing, China, Jun. 21-25, 2010; pp. 1, 3, 10, and 13.
Min, C.K. et al., "Cutaneous leucoclastic vasculitis (LV) following bortezomib therapy in a myeloma patient; association with pro-inflammatory cytokines" *Eur J Haematol*, 2006. 76(3):265-8.

(56) References Cited

OTHER PUBLICATIONS

Mirguet, O. et al., "From ApoA1 upreguiation to BET family bromodomain inhibition: discovery of I-BET151" *Bioorg Med Chem Lett*, Article in Press, 2012. doi: 10.1016/j.bmcl.2012.01.125, 5 pages. Final publication in vol. 22, No. 8, pp. 2963-7.
Mitchell et al., "Bromination of 4,6-dimethoxyindoles" *Tetrahedron* 68(39):8163-8171 (2012)
Mitsuyama, K. et al., "STAT3 activation via interleukin 6 trans-signalling contributes to ileitis in SAMP1/Yit mice" *Gut*, 2006. 55(9):1263-9.
Miyazaki, et al. "Intravenous Injection of Rabbit Apolipoprotein A-I inhibits the Progression of Atherosclerosis in Cholesterol-Fed Rabbits" *Arterioscler. Thromb. Vasc. Biol.* 15: 1882-1888 (1995).
Moffett, "Azacotimarins" *J. Org. Chem.* 35(11):3596-3600 (1970).
Mok, M.Y. et al., "The relation of interleukin 17 (IL-17) and IL-23 to Th1/Th2 cytokines and disease activity in systemic lupus erythematosus" *J Rheumatol*, 2010. 37(10):2046-52.
Mondal et al., "Two-Stage Chemical Oncogenesis in Cultures of C3H/10T1/2 Cells" *Cancer Res.* 36:2254-2260 (1976).
Morin, R.D. et al., "Frequent mutation of histone-modifying genes in non-Hodgkin lymphoma" *Nature*, 2011. 476(7360):298-303. (Author manuscript, 17 pages).
Mudter, J. and M.F. Neurath, "IL-6 signaling in inflammatory bowel disease: pathophysiological role and clinical relevance" *Inflamm Bowel Des*, 2007. 13(8):1016-23.
Muller Kobold, A.C. et al., "In vitro up-regulation of E-selectin and induction of interieukin-6 in endothelial cells by autoantibodies in Wegener's granulomatosis and microscopic polyangiitis" *Clin Exp Rheumetol*, 1999. 17(4):433-40.
Muller, S. et al., "Bromodomains as therapeutic targets" *Expert Rev Mol Med*, 2011. 13: e29, 21 pages.
Nakahama, H. et al., "Distinct responses of interleukin-6 and other laboratory parameters to treatment in a patient with Wegener's granulomatosis" *Intern Med*, 1993. 32(2):189-92.
Narayana, B.L. et al., "Synthesis of New 2-Substituted Pyrido[2,3-d]pyrimidine-4(1H)-ones and Their Antibacterial Activity" *Eur. J. Med. Chem.* 44(3)1369-1376 (2009).
Nelken, N.A. et al., "Monocyte chemoattractant protein-1 in human atheromatous plaques" *J Clin Invest*, 1991. 88(4):1121-7.
Ni, J. et al., "Involvement of Interleukin-17A in Pancreatic Damage in Rat Experimental Acute Necrotizing Pancreatitis" *Inflammation*, 2012. [online] DOI: 10.1007/s10753-012-9519-5, published Sep. 19, 2012 (13 pages).
Nicholls et al., "Efficacy and Safety of a Novel Oral Inducer of Apolipoprotein A-I Synthesis in Statin-Treated Patients with Stable Coronary Artery Disease" *J. Am. Coll. Cardiol.* 57(9):1111-1119 (2011).
Nicodeme et al., "Suppression of inflammation by a synthetic histone mimic" *Nature* 468:1119-1123 (2010).
Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990)
Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).
Niu, J. and P.E. Kolattukudy, "Role of MCP-1 in cardiovascular disease: molecular mechanisms and clinical implications" *Clin Sci*, 2009. 117(3):95-109.
Nourooz-Zadeh, "Ferrous Ion Oxidation in Presence of Xylenol Orange for Detection of Lipid Hydroperoxides in Plasma" *Methods Enzymol.* 300:58-62 (1999).
Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).
Ooi, J.D. et al, "Review: T helper 17 cells: their role in glomerulonephritis" *Nephrology*, 2010. 15(5):513-21.
Ordovas, J.M., "Gene-diet interaction and plasma lipid responses to dietary intervention" *Biochem. Soc. Trans.* 30(2):68-73 (2002).

Ortiz-Lucas, M. et al., "Irritable bowel syndrome immune hypothesis. Part two: the role of cytokines" *Rev Esp Enferm Dig*, 2010. 102(12):711-7.
Ott, C.J. et al., "BET bromodomain inhibition targets both c-Myc and IL7R in highrisk acute lymphoblastic leukemia" *Blood*, 2012. 120(14):2643-52.
Palermo, R.D. et al., RNA polymerase II stalling promotes nucleosome occlusion and pTEFb recruitment to drive immortalization by Epstein-Barr virus. *PLoS Pathog*, 2011, 7(10): e1002334, 15 pages.
Paquet, P. and C.E. Pierard, "Interleukin-6 and the skin" *Int Arch Allergy Immunol*, 1996. 109(4):308-17.
Parra et al., "A Case-Control Study of Lipoprotein Particles in Two Populations at Contrasting Risk for Coronary Heart Disease" *Arterioscler Thromb.* 12:701-707 (1992).
Patani et al., "Bioisosterism: A Rational Approach in Drug Design" *Chem. Rev.* 96(8):3147-3176 (1996).
Pearson et al., "The *ortho* Bromination of Phenols" *J. Org. Chem.* 32:2358-2360 (1967).
Peserico, A. and C. Simone, "Physical and functional HAT/HDAC interplay regulates protein acetylation balance" *J Biomed Biotechnol*, 2011. 371832, 10 pages.
Pettit et al., "Antineoplastic Agents, 465. Structural Modification of Resveratrol: Sodium Resverastatin Phosphate" *J. Med. Chem.* 45:2534-2542 (2002).
Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).
Poreba, E. et al., "Epigenetic mechanisms in virus-induced tumorigenesis" *Clin Epigenetics*, 2011. 2(2):233-47.
Prabakaran, K. et al., "Iridium bromide catalysed, ultrasound-assisted, region-selective synthesis of ethyl-5-(trifluoromethyl)-1-(3-substituted-isoquinolin-l-yl)-1H-pyrazole-4-carboxylates", *Res. Chem. Intermed.*, 38:429-441 (2012).
Prinjha, R.K. et al., "Place your BETs: the therapeutic potential of bromodomains" *Trends Pharmacol Sci*, 2012. 33(3):146-53.
Quinones et al., "The *egr-1* gene is induced by DNA-damaging agents and non-genotoxic drugs in both normal and neoplastic human cells" *Life Sciences* 72(26):2975-2992 (2003).
Radstake, T.R. et al., "The pronounced Th17 profile in systemic sclerosis (SSc) together with intracellular expression of TGFbeta and IFNgamma distinguishes SSc phenotypes" *PLoS One*, 2009. 4(6):e5903. 9 pages.
Ragione et al., "Antioxidants induce different phenotypes by a distinct modulation of signal transduction" *FEBS Letters* 523:289-294 (2002).
Ragione et al., "p21$^{CIP}$1 Gene Expression is Modulated by Egr1: A Novel Regulatory Mechanism Involved in the Resveratrol Antiproliferative Effect" *J. Biol. Chem.* 278:23360-23368 (2003).
Rajakumar et al., "TiCl$_4$, Dioxane—A facile and efficient system for de-O-benzylation, de-O-allylation, and de-O-xylylation of phenolic ethers" *Synthetic Communications* 33(22):3891-3896 (2003).
Ramsay, R.G. and T.J. Gonda, "MYB function in normal and cancer cells" *Nat Rev Cancer*, 2008. 8(7):523-34.
Raun et al., "Apolipoprotein A-I possesses an anti-obesity effect associated with increase of energy expenditure and upregulatior, of UCP1 in brown fat" *J. Cell. Mol. Med.* (2010), "Postprint"; 10.1111 /j.1582.4934.2010.01045.x.
Raychaudhuri, S.P. et al., "IL-17 receptor and its functional significance in psoriatic arthritis" *Mol Cell Biochem*, 2012. 359(1-2):419-29.
Rhodus. N.L. et al., "Proinflammatory cytokine levels in saliva before and after treatment of (erosive) oral lichen planus with dexamethasone" *Oral Dis*, 2006. 12(2)112-6.
Rice-Evans, "Flavonoids and Isoflavones: Absorption, Metabolism, and Bioactivity" *Free Radical Biol. Med.* 36:827-828 (2004).
Rigotti et al., "Regulation by Adrenocorticotropic Hormone of the In Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).
Rimando et al., "Pterostiibene, a New Agonist for the Peroxisome Proliferator-Activated Receptor α-Isoform, Lowers Plasma

(56) References Cited

OTHER PUBLICATIONS

Lipoproteins and Cholesterol in Hypocholesterolemic Hamsters" *Journal of Agricultural and Food Chemistry* 53(9):3403-3407 (2005).
Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).
Rodriguez, R.M. et al., "Aberrant epigenetic regulation of bromodornain BRD4 in human colon cancer" *J Mol Med*, 2012 90(5):587-95.
Roger, V.L. et al., "Heart Disease and stroke statistics—2012 update: a report from the American Heart Association" *Circulation*, 2012. 125(1):3-e220.
Rose et al., "Oxygen Heterocycles. XIII. From 3-Arylisocoumarins to 3-Aryllsoquinolines and 4-Aryl-5$H$-2.3- Benzodiazepines" *J. Chem. Soc. [Section] C: Organic* 17:2205-2208 (1968).
Rubin et al., "Expression of Human Apolipoprotein A-I in Transgenic Mice Results in Reduced Plasma Levels of Murine Apolipoprotein A-I and the Appearance of Two New High Density Lipoprotein Size Subclasses" *Proc. Natl. Acad. Sci. USA* 88:434-438 (1991).
Rubin et al., "Inhibition of Early Atherogenesis in Transgenic Mice by Human Apolipoprotein AI" *Nature* 353:265-267 (1991).
Rubins et al., "Reduction in Stroke with Gemfibrozil in Men with Coronary Heart Disease and Low HDL Cholesterol. The Veterans Affairs HDL Intervention Trial (VA-HIT)" *Circulation* 103:2828-2833 (2001).
Ruden, M. and N. Puri, "Novel anticancer therapeutics targeting telomerase" *Cancer Treat Rev*, 2012. Article in Press: http://dx.doi.org/10.1016j.ctrv.2012.06.007. 13 pages.
Rudloff, U. and Y. Samuels, "TYR03-mediated regulation of MITF: a novel target in melanoma?" *Pigment Cell Melanoma Res*, 2010. 23(1):9-11.
Sanchez, R. and M.M. Zhou, "The role of human bromodomains in chromatin biology and gene transcription" *Curr Opin Drug Discov Devel*, 2009 12(5):659-65. (Author manuscript, 12 pages.).
Sarkhel et al., "3-Arylisocoumarin: Synthesis of 3-(4-methoxyphenyl)-isocoumarin" J. Indian Chem. Soc. 53:915-916 (1976).
Scanlan, M.J. et al., "Expression of cancer-testis antigens in lung cancer: definition of bromodomain testis-specific gene (BRDT) as a new CT gene, CT9" *Cancer Lett*, 2000. 150(2):155-64.
Schiess et al., "Thermolytic Ring Opening of Acyloxybenzocyclobutenes: An Efficient Route to 3-Substituted Isoquinolines" *Tetrahedron Lett*. 26:3959-3962 (1985).
Schmutz et al., "Synthese von basisch substituierten Chromonen" *Helv. Chim. Acta* 36:620-626 (1953) (German). English abstract from *Chemical Abstracts*, vol. 48, col. 11401 (1954).
Schork, N.J., "Genetics of Complex Disease. Approaches, Problems and Solutions" *Am. J. Respir. Crit. Care Med.* 156(4):S103-109 (Oct. 1997).
Schultz et al., "Role of stilbenes in the natural durability of wood: fungicidal structure-activity relationships" *Phytochemistry* 29(5):1501-1507 (1990).
Seal, J. et al., "Identification of a novel series of BET family bromodomain inhibitors: Binding mode and profile of I-BET15I(GSK121051A)" *Bioorg. Med. Chem. Lett.*, 22:2968-2972 (2012).
Segura, M.F. et al., "BRD4 is a novel therapeutic target in melanoma" Poster Presentation, AACR 103rd Annual Meeting, Mar. 31-Apr. 4, 2012 in Chicago, IL. *Cancer Research*, 2012. 72(8), Supplement 1, Abstract 2185.
Shah et al., "Effects of Recombinant Apolipoprotein A-I$_{Milano}$ on Aortic Atherosclerosis in Apolipoprotein E—Deficient Mice" *Circulation* 97(8):780-785 (1998).
Shang, E. et al., "The first bromodomain of Brdt, a testis-specific member of the BET sub-family of double-bromodomain—containing proteins, is essential for male germ cell differentiation" *Development*, 2007. 134(19):3507-15.

Shapiro et al., "Micro Assay for 3-Hydroxy-3-Methylglutaryl-CoA Reductase in Rat Liver and L-Cell Fibroblasts" *Biochem. Biophys. Acta* 370:369-377 (1974).
Sharrett et al., "Associations of Lipoprotein Cholesterols, Apolipoproteins A-I and B, and Triglycerides with Carotid Atherosclerosis and Coronary Heat Disease. The Atherosclerosis Risk in Communities (ARIC) Study" *Arterioscler. Thromb.* 14:1096-1104 (1994).
Shibuya M. et al., "Successful treatment with tocilizumab in a case of Cogan's syndrome complicated with aortitis" *Mod Rheumatol*, 2012. online: DOI 10.1007/s10165-012-0691-0, 5 pages.
Sieber, R.H., "Reactions of chloroacetaldehyde with aromatic hydrocarbons, phenols, and phenold ethers" *Justus Liebigs Annalen der Chemie* 730:31-46 (1969) (German). English abstract on p. 31.
Simmons E.M. et al., "Plasma cytokine levels predict mortaiity in patients with acute renal failure" *Kidney Int*, 2004. 65(4):1357-65,
Simone, C. and A. Giordano, "Abrogation of signal-dependent activation of the cdk9/cyclin T2a complex in human RD rhabdomyosarcoma cells" *Cell Death Differ*, 2007. 14(1):192-5.
Sliwa et al., "Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939-944 (1997) (French), English summary on p. 944.
Slowing et al., "Anti-Inflammatory Activity of Leaf Extracts of *Eugenia jambos* in Rats" *J. Ethnopharmacol*. 43:9-11 (1994).
Smyth et al., "Non-amine based analogues of lavendustin A as protein-tyrosine kinase Inhibitors" *J. Med. Chem.* 36(20):3010-3014 (1993).
Soltesz, P. et al., "Immunological features of primary antiphospholipid syndrome in connection with endothelial dysfunction" *Rheumatology*, 2008. 47(11):1628-34.
Stenman, G. et al., "New tricks from an old oncogene: gene fusion and copy number alterations of MYB in human cancer" *Cell Cycle*, 2010. 9(15):2986-95.
Sun et al., "In Vitro Testing of Drug Absorption for Drug 'Developability' Assessment: Forming an Interface Between in Vitro Preclinical Data and Clinical Outcome" *Curr. Opin. Drug Discov. Devel.* 7:75-85 (2004).
Sun, Y. et al., "MMP-9 and IL-6 are potential biomarkers for disease activity in Takayasu's arteritis" *Int J Cardiol*, 2012, 156(2):236-8.
Suryadevara et al., "Association of Abnormal Serum Lipids in Elderly Persons with Artherosclerotic Vasciuar Disease and Demetia, Artheroslerotic Vascular Disease Without Demetia, Demetia Without Artherosclerotic Vascular Disease, and No Dementia or Artherosclerotic Vascular Disease" *J. Gerontol. Med. Sci.* 58A(9):859-861 (2003).
Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).
Talbert, "Current Recommendatiions for the Treatment of Dyslipidemia" *Pharm. Ther.* 29:104 (2004).
Tall "Plasma High Density Lipoproteins" *J. Clin. Invest.* 86: 379-384 (1990).
Tanne et al., "High-Density Lipoprotein Cholesterol and Risk of Ischemic Stroke Mortality" *Stroke* 28:83-87 (1997).
Tardif et al., "Probucol and Multivitamins in the Prevention of Restenosis After Coronary Angioplasty" *N. Engl. J. Med.* 337:365-367 (1997).
Taylan, A. et al., "Evaluation of the T helper 17 axis in ankylosing spondylitis" *Rheumatol Int*, 2012. 32(8):2511-5.
Theriault et al., "Modulation of hepatic lipoprotein synthesis and secretion by taxifolin, a plant fiavonoid," *J. Lipid Res.* 41:1969-1979 (2000).
Tong, W.G. et al., "Phase I and pharmacologic study of SNS-032, a potent and selective Cdk2, 7, and 9 inhibitor, in patients with advanced chronic lymphocytic leukemia and multiple myeloma" *J Clin Oncol*, 2010. 28(18):3015-22.
Toth et al., "Therapeutic interventions Targeted at the Augmentation of Reserve Cholesterol Transport" *Curr. Opin. Cardiol.* 19:374-379 (2004).
Tovar et al., "Pyrylium Salts via Electrophilic Cyclization: Applications for Novel 3-Arylisoquinoline Syntheses" *J. Org. Chem.* 64:6499-6504 (1999).

(56) References Cited

OTHER PUBLICATIONS

Traves, S.L. and L.E. Donnelly, "Th17 cells in airway diseases" *Curr. Mol. Med.*, 2008. 8(5):416-26.

Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)" *Biochem. Pharmacol*, 58:1869-1880 (1999).

Uchida, T. et al., "Antitumor effect of bcl-2 antisense phosphorothioate aligodeoxynucleotides on human renal-cell carcinoma cells in vitro and in mice" *Mol Urol*, 5(2):71-8.

Urano, W. et al., "The inflammatory process in the mechanism of decreased serum uric acid concentrations during acute gouty arthritis" *J Rheumatol*, 2002. 29(9):1950-3, Utermann, "The Mysteries of Lipoprotein(a)" *Science* 246:904-910 (1989).

Van Der Goot et al., "The Growth-Inhibitory Action of Some 1-Aminoisoquinolines and Related Compounds on Mycoplasma Gallisepticum" *Eur. J. Med. Chem.—Chimica Thereapeutica* 10:603-606 (1975).

Varin et al., "Enzymatic Assay for Flavonoid Sulfotransferase" *Anal. Biochem.* 161:176-180 (1987).

Varthalis et al., "The action of colloidai silicon dioxide as a glidant for lactose, paracetamol, oxytetracycline and their mixtures" *J. Pharm. Pharmac.* 29:37-40 (1997).

Velisek, L. et al., "GABAergic neuron deficit as an idiopathic generalized epilepsy mechanism: the role of BRD2 haploinsufficiency in juvenile rnyoclonic epilepsy" *PLoS One*, 2011. 6(8): e23656, 8 pages.

Vernarecci, S. et al., "Tuning acetylated chromatin with HAT inhibitors: a novel tool for therapy" *Epigenetics*, 2010. 5(2): p. 105-11.

Vidal, B. et al., "Discovery and Characterization of 4'-(2-Furyl)-*N*-pyridin-3-yl-4,5'-bipyrimidin-2'-amine (LAS38096), a Potent, Selective, and Efficacious $A_{2B}$ Adenosine Receptor Antagonist" *J. Med. Chem.* 50:2732-2736 (2007).

Vippagunta et al., "Crystalline solids" *Adv. Drug Delivery Rev.* 48:3-26 (2001).

Vita, M. and M. Henriksson, "The Myc oncoprotein as a therapeutic target for human cancer" *Semin Cancer Biol*, 2006, 16(4):318-30.

Voitenko et al., "Esters of o-(4-oxo-3,4-dihydro-2-quinazolinyl)benzoic acid and 5,11-dihydroisoindolo[2,1-a]quinazolinone-5 derivatives as β-cyclodextrin modifiers" *Dopovidi Natsional'noi Akademii Nauk Uraini*, 8:132-138 (2005).

Walle, "Absorption and Metabolism of Flavonoids" *Free Radical Biol. Med.* 36(7):829-837 (2004).

Wang, F. et al., "Brd2 disruption in mice causes severe obesity without Type 2 diabetes" *Biochem J*, 2010. 425(1): p. 71-83, with supplemental online materiai. 2 pages.

Wang, G. et al., "Increased cyclin-dependent kinase 6 expression in bladder cancer" *Oncol Lett*, 2012. 4(1): p. 43-46.

Wang, S. and P.M. Fischer, "Cyclin-dependent kinase 9: a key transcriptional regulator and potential drug target in oncology, virology and cardiology" *Trends Phermacol Sci*, 2008. 29(6):302-13.

Watson, J.D. "Curing "incurable" cancer" *Cancer Discov*, 2011. 1(6):477-80.

Wei et al., "Total Cholesterol and High Density Lipoprotein Cholesterol as Important Predictors of Erectile Dysfunction" *Am. J. Epidemiol*, 140(10):930-937 (1994).

Welsh et al., "Dyslipidemia in Diabetic Patients" *Prospectives in Cardiology*, Aug. 2002, pp. 40-48.

Wölle et al., "Selective inhibition of tumor necrosis factor-induced vascular cell adhesion molecule-1 gene expression by a novel flavonoid. Lack of effect on transcription factor NF-kappa-B" *Arterioscler. Thromb. Vasc. Biol.* 16(12):1501-1508 (1996).

Wu, S.Y. and C.M. Chiang, "The double bromodomain-containing chromatin adaptor Brd4 and transcriptional regulation" *J Biol Chem*, 2007. 262(18):13141-5.

Wurm et al., "1,4-Naphthoquinones, XXVI: Phenyl-1,4-naphthoquinone derivatives with the hydroxylation patterns of bioflavonoids" *Pharmazie* 52(10):739-743 (1997) (German). English abstract on p. 739.

Wurm, "1,4-Naphthoquinones, XXI: 2-(3,5 Di-*tert*-butyl-4-hydroxyphenyl)-1,4-naphtoquinones as 5-lipozxygenase inhibitors" *Archiv. der Pharmazie* 324(8):491-495 (1991) (German). English summary on p. 491.

Xing, W. et al., "Discovery of novel 2,6-disubstituted pyridazinone derivatives as acetylcholinesterase inhibitors" *Eur. J. Med. Chem.* 63:95-103 (2013).

Xu, L. et al., "Critical role of Th17 cells in development of autoimmune hemolytic anemia" *Exp Hematol*, 2012. Article in Press: http://dx.doi.org/10.1016/j,exphem.2012.08.008, 15 pages.

Yamaguchi, M. et al., "Novel Antiasthmatic Agents with Dual Activities of Thromboxane $A_2$ Synthetase Inhibition and Bronchodilation. 2. 4-(3-Pyridyl)-1(2*H*)-phthalazinones" *J. Med. Chem.*, 36:4061-4068 (1993).

Yamakoshi et al., "Isoflavone aglycone-rich extract without soy protein attenuates atherosclerosis development in cholesterol-fed rabbits" *Journal of Nutrition* 130(8):1887-1893 (2000).

Yamashita, T. et al., "IL-6-mediated Th17 differentiation through RORγt is essential for the initiation of experimental autoimmune mycarditis" *Cardiovasc Res*, 2011, 91(4):640-8.

Yardley et al., "In Vitro activity of diospyrin and derivaties against *Leishmania donovani*, *Trypanosome cruzi* and *Trypanosome brucel brucel*" *Phytotherapy Research* 10(7):559-562 (1996).

Yoshii, T. et al., "Local levels of interleukin-1beta, -4, -6 and tumor necrosis factor alpha in an experimental model of murine osteomyelitis due to *Staphylococcus aureus*" *Cytokine*, 2002 19(2): p. 59-65.

Yoshimura, T. et al., "Involvement of Th17 cells and the effect of anti-IL-6 therapy in autoimmune uveitis" *Rheumatology*, 2009 48(4):347-54.

Yoshioka et al., "Semiempirical Investigation of Stilbene-Linked Diradicals and Magnetic Study of Their Bis(*N-tert*-butylnitroxide) Variants" *J. Org. Chem.* 59(15):4272-4280 (1994).

You, J. et al., "Kaposi's sarcoma-associated hypesvirus latency-associated nuclear antigen interacts with bromodomain protein Brd4 on host mitotic chromosomes" *J. Virol*, 2006. 80(18):8909-19.

Zhang, G. et al., "Down-regulation of NF-kappaB Transcriptional Activity in HIVassociated Kidney Disease by BRD4 Inhibition" *JBC Papers in Press*, 2012, M112.359505 with supplement, 38 pages. Final publication in: *J Biol Chem*, 287(34):28840-51.

Zhang, W.S. et al., "Bromodomain-Containing-Protein 4 (BRD4) Regulates RNA Polymerase II Serine 2 Phosphorylation in Human CD4+ T Cells" JBC Papers in Press, 2012 M112.413047. 30 pages. Final publication in: *J Biol Chem*, 287:43137-55.

Zhao, L. et al., "Interleukin-17 contributes to the pathogenesis of autoimmune hepatitis through inducing hepatic interleukin-6 expression" *PLoS One*, 2011. 6(4):e18909, 8 pages.

Zhou, M. et al., "Bromodomain protein Brd4 regulates human immunodeficiency virus transcription through phosphorylation of CDK9 at theronine 29" *J Virol*, 2009. 83(2):1036-44.

Zhu, J. et al., "Reactivation of Latent HIV-1 by Inhibition of BRD4" Cell Rep, 2012. 2:1-10. with supplemental pp. S1-S7.

Zuber, J. et al., "RNAi screen identifies Brd4 as a therapeutic target in acute myeloid leukaemia" *Nature*, 2011 478(7370):524-8.

"RVX 208" R&D Insight Profile in Drugs 11(2):207-213 (2011).

Brennan, P., "Isoxazole Inhibitors of Bromodomains" presented at the *RCS Advances in Synthesis and Medicinal Chemistry Conference*, BioPark, Welwyn Garden City, UK, May 1, 2012 (46 pages).

Chung, C.W. et al., "Bromodomains: a new target class for small molecule drug discovery" Drug Discover Today: Therapeutic Strategies 9(2-3):e111-e120 (2012).

Hewings et al., "3,5-Dimethylisoxazoles Act as Acetyl-lysine-mimetic Bromodomain Ligands" J. Med. Chem 54:6761-6770 (2011).

(56) References Cited

OTHER PUBLICATIONS

Hewings et al., "3,5-Dimethylisoxazoles inhibit the bromodomain-histone protein-protein interaction" 243rd National Spring Meeting of the American-Chemical-Society (Symposium on Ionic Liquids—Science and Applications), San Diego, CA. General Poster Session, Mar. 28, 2012, Poster 326 Abstract [online]. Retrieved from: http://acselb-529643017.us-west-2.elb.amazonaws.com/chem/243nm/program/view.php?pub_num=326&par=MEDI.

Hewings et al., "Optimization of 3,5-Dimethylisoxazole Derivatives as Potent Bromodomain Ligands" J. Med. Chem. 56:3217-3227 (2013).

International Search Report and Written Opinion issued in International Application No. PCT/IB2014/002510; Date of Mailing: Apr. 15, 2015.

International Search Report and Written Opinion issued in International Application No. PCT/US2005/038048; Date of Mailing: Mar. 7, 2007.

International Search Report and Written Opinion issued in International Application No. PCT/US2006/029827; Date of Mailing: Apr. 16, 2007.

McLure et al., "RVX-208, and Inducer of ApoA-I in Humans, Is a BET Bromodomain Antagonist" PLOS One, 8(12):e83190 (2013) (12 pages).

CYCLIC AMINES AS BROMODOMAIN INHIBITORS

This application is a divisional of U.S. patent application Ser. No. 14/085,545, filed Nov. 20, 2013 (issued as U.S. Pat. No. 9,073,878 on Jul. 7, 2015), which claims the benefit of U.S. Provisional Application No. 61/729,097, filed Nov. 21, 2012, all of which are incorporated herein by reference in their entirety.

The present disclosure relates to novel compounds, pharmaceutical compositions containing such compounds, and their use in prevention and treatment of diseases and conditions.

Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs) [1]. Small molecule inhibitors of HDACs and HATs are being investigated as cancer therapy [2-5]. Histone acetylation controls gene expression by recruiting protein complexes that bind directly to acetylated lysine via bromodomains [6]. One such family, the bromodomain and extra terminal domain (BET) proteins, comprises Brd2, Brd3, Brd4, and BrdT, each of which contains two bromodomains in tandem that can independently bind to acetylated lysines, as reviewed in [7].

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis [8].

BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections [8, 9].

Autoimmune diseases, which are often chronic and debilitating, are a result of a dysregulated immune response, which leads the body to attack its own cells, tissues, and organs. Pro-inflammatory cytokines including, IL-1β, TNF-α, IL-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy [10].

BET inhibitors are expected to have anti-inflammatory and immunomodulatory properties [8, 9]. BET inhibitors have been shown to have a broad spectrum of anti-inflammatory effects in vitro including the ability to decrease expression of pro-inflammatory cytokines such as IL-1β, MCP-1, TNF-α, and IL-6 in activated immune cells [11-13]. The mechanism for these anti-inflammatory effects may involve BET inhibitor disruption of Brd4 co-activation of NF-κB-regulated pro-inflammatory cytokines and/or displacement of BET proteins from cytokine promoters, including IL-6 [12, 14, 15]. In addition, because Brd4 is involved in T-cell lineage differentiation, BET inhibitors may be useful in inflammatory disorders characterized by specific programs of T cell differentiation [16].

The anti-inflammatory and immunomodulatory effects of BET inhibition have also been confirmed in vivo. A BET inhibitor rescued mice from endotoxin- or bacterial sepsis-induced death and cecal ligation puncture-induced death, suggesting utility for BET inhibitors in sepsis and acute inflammatory disorders [12]. A BET inhibitor has been shown to ameliorate inflammation and kidney injury in HIV-1 transgenic mice, an animal model for HIV-associated nephropathy, in part through inhibition of Brd4 interaction with NF-κB [14]. The utility of BET inhibition in autoimmune disease was demonstrated in a mouse model of multiple sclerosis, where BET inhibition resulted in abrogation of clinical signs of disease, in part, through inhibition of IL-6 and IL-17 [17]. These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells [18].

BET inhibitors may be useful in the treatment of a variety of chronic autoimmune inflammatory conditions. Examples of autoimmune and inflammatory diseases, disorders, and syndromes treated using the compounds and methods include, but are not limited to, inflammatory pelvic disease, urethritis, skin sunburn, sinusitis, pneumonitis, encephalitis, meningitis, myocarditis, nephritis [14], osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis [9], Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis [18], scleroderma, vasculitis, autoimmune hemolytic and thrombocytopenic states, Goodpasture's syndrome, atherosclerosis, Addison's disease, Parkinson's disease, Alzheimer's disease, Type I diabetes [8], septic shock [12], systemic lupus erythematosus (SLE) [9], rheumatoid arthritis [19], psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions including, but not limited to, acute gout, giant cell arteritis, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock [12], systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus [8].

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs [20, 21].

The present disclosure provides a method for treating human cancer, including, but not limited to, cancers that result from aberrant translocation or overexpression of BET proteins (e.g., NUT midline carcinoma (NMC) [22]) and B-cell lymphoma [23]). NMC tumor cell growth is driven by a translocation of the Brd4 or Brd3 gene to the nutlin 1 gene [24]. BET inhibition has demonstrated potent antitumor activity in murine xenograft models of NMC, a rare but lethal form of cancer [24].

The present disclosure provides a method for treating human cancers, including, but not limited to, cancers dependent on a member of the myc family of oncoproteins including c-myc, MYCN, and L-myc [25]. These cancers include Burkitt's lymphoma, acute myelogenous leukemia, multiple myeloma, and aggressive human medulloblastoma [25]. Cancers in which c-myc is overexpressed may be particularly susceptible to BET protein inhibition; it has been shown that treatment of tumors that have activation of c-myc with a BET inhibitor resulted in tumor regression through inactivation of c-myc transcription [26-30].

The present disclosure provides a method for treating human cancers including cancers that rely on BET proteins and pTEFb (Cdk9/CyclinT) to regulate oncogenes [31], and cancers that can be treated by inducing apoptosis or senescence by inhibiting Bcl2, cyclin-dependent kinase 6 (CDK6) [26], or human telomerase reverse transcriptase (hTERT) [27, 32].

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia [26, 28, 30], adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia [29], B-cell chronic lymphocytic leukemia, B-cell prolymphocytic leukemia, B-cell lymphoma [23], basal cell carcinoma, biliary tract cancer, bladder cancer, blastoma, bone cancer, Brenner tumor, Brown tumor, Burkitt's lymphoma [28], breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular, thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia [28], chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma [33], meningioma, Merkel cell cancer, mesothelioma, metastatic urothelial carcinoma, mixed Mullerian tumor, mixed lineage leukemia [26], mucinous tumor, multiple myeloma [27], muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma [24], ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis.

Cardiovascular disease (CVD) is the leading cause of mortality and morbidity in the United States [34]. Atherosclerosis, an underlying cause of CVD, is a multifactorial disease characterized by dyslipidemia and inflammation. BET inhibitors are expected to be efficacious in atherosclerosis and associated conditions because of aforementioned anti-inflammatory effects as well as ability to increase transcription of ApoA-I, the major constituent of HDL [11, 35].

Up-regulation of ApoA-I is considered to be a useful strategy in treatment of atherosclerosis and CVD [36], BET inhibitors have been shown to increase ApoA-I transcription and protein expression [11, 35]. Resverlogix has also shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-I and HDL such as hypercholesterolemia, dyslipidemia, atherosclerosis [36], and Alzheimer's disease and other neurological disorders [37].

BET inhibitors may be useful in the prevention and treatment of conditions associated with ischemia-reperfusion injury such as, but not limited to, myocardial infarction, stroke, acute coronary syndromes [9], renal reperfusion injury, organ transplantation, coronary artery bypass grafting, cardio-pulmonary bypass procedures, hypertension, pulmonary, renal, hepatic, gastro-intestinal, or peripheral limb embolism.

Obesity-associated inflammation is a hallmark of type II diabetes, insulin resistance, and other metabolic disorders [8, 19]. Consistent with the ability of BET inhibitors to inhibit inflammation, gene disruption of Brd2 in mice ablates inflammation and protects animals from obesity-induced insulin resistance [38]. It has been shown that Brd2 interacts with PPARγ and opposes its transcriptional function. Knockdown of Brd2 in vitro promotes transcription of PPARγ-regulated networks, including those controlling adipogenesis [39]. In addition Brd2 is highly expressed in pancreatic β-cells and regulates proliferation and insulin transcription [38]. Taken together, the combined effects of BET inhibitors on inflammation and metabolism decrease insulin resistance and may be useful in the treatment of pre-diabetic and type II diabetic individuals as well as patients with other metabolic complications [8].

Host-encoded BET proteins have been shown to be important for transcriptional activation and repression of viral promoters. Brd4 interacts with the E2 protein of human papilloma virus (HPV) to enable E2 mediated transcription of E2-target genes [40]. Similarly, Brd2, Brd3, and Brd4 all bind to latent nuclear antigen 1 (LANA1), encoded by Kaposi's sarcoma-associated herpes virus (KSHV), promoting LANA1-dependent proliferation of KSHV-infected cells [41]. A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies [42]. Also, a BET inhibitor reactivated HIV in models of latent T cell infection and latent monocyte infection, potentially allowing for viral eradication by complementary anti-retroviral therapy [43-46].

BET inhibitors may be useful in the prevention and treatment of episome-based DNA viruses including, but not limited to, human papillomavirus, herpes virus, Epstein-Barr virus, human immunodeficiency virus [8], adenovirus, poxvirus, hepatitis B virus, and hepatitis C virus.

Some central nervous system (CNS) diseases are characterized by disorders in epigenetic processes. Brd2 haploinsufficiency has been linked to neuronal deficits and epilepsy [47]. SNPs in various bromodomain-containing proteins have also been linked to mental disorders including schizophrenia and bipolar disorders [9]. In addition, the ability of BET inhibitors to increase ApoA-I transcription may make BET inhibitors useful in Alzheimer's disease therapy considering the suggested relationship between increased ApoA-I and Alzheimer's disease and other neurological disorders [37].

BRDT is the testis-specific member of the BET protein family which is essential for chromatin remodeling during [48, 49]. Genetic depletion of BRDT or inhibition of BRDT interaction with acetylated histones by a BET inhibitor resulted in a contraceptive effect in mice, which was reversible when small molecule BET inhibitors were used [50, 51]. These data suggest potential utility of BET inhibitors as a novel and efficacious approach to male contraception.

Monocyte chemotactic protein-1 (MCP-1, CCU) plays an important role in cardiovascular disease [52]. MCP-1, by its chemotactic activity, regulates recruitment of monocytes from the arterial lumen to the subendothelial space, where they develop into macrophage foam cells, and initiate the formation of fatty streaks which can develop into atherosclerotic plaque [53]. The critical role of MCP-1 (and its cognate receptor CCR2) in the development of atherosclerosis has been examined in various transgenic and knockout mouse models on a hyperlipidemic background [54-57]. These reports demonstrate that abrogation of MCP-1 signaling results in decreased macrophage infiltration to the arterial wall and decreased atherosclerotic lesion development.

The association between MCP-1 and cardiovascular disease in humans is well-established [52]. MCP-1 and its receptor are overexpressed by endothelial cells, smooth muscle cells, and infiltrating monocytes/macrophages in human atherosclerotic plaque [58]. Moreover, elevated circulating levels of MCP-1 are positively correlated with most cardiovascular risk factors, measures of coronary atherosclerosis burden, and the incidence of coronary heart disease (CHD) [59]. CHD patients with among the highest levels of MCP-1 are those with acute coronary syndrome (ACS) [60]. In addition to playing a role in the underlying inflammation associated with CHD, MCP-1 has been shown to be involved in plaque rupture, ischemic/reperfusion injury, restenosis, and heart transplant rejection [52].

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients [61]. Blockade of MCP-1 and MCP-1 signaling in animal models of RA have also shown the importance of MCP-1 to macrophage accumulation and proinflammatory cytokine expression associated with RA [62-65].

Overexpression of MCP-1, in the brain, cerebrospinal fluid (CSF), and blood, has also been associated with chronic and acute MS in humans [66]. MCP-1 is overexpressed by a variety of cell types in the brain during disease progression and contributes to the infiltration of macrophages and lymphocytes which mediate the tissue damage associated with MS [66]. Genetic depletion of MCP-1 or CCR2 in the experimental autoimmune encephalomyelitis (EAE) mouse model, a model resembling human MS, results in resistance to disease, primarily because of decreased macrophage infiltration to the CNS [67, 68].

Preclinical data have suggested that small- and large-molecule inhibitors of MCP-1 and CCR2 have potential as therapeutic agents in inflammatory and autoimmune indications.

The present disclosure includes compounds that are useful for inhibition of BET protein function by binding to bromodomains, and their use in the treatment and prevention of diseases and conditions, including, but not limited to, cancer, autoimmune, and cardiovascular diseases.

The first aspect of the present disclosure includes compounds of Formula I and methods of administering a therapeutically effective amount of those compounds to a mammal (e.g., a human) in need thereof:

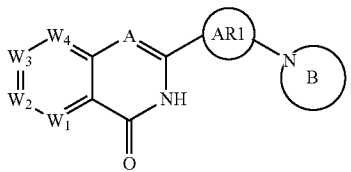

Formula I or a stereoisomer, tautomer, pharmaceutical acceptable salt, or hydrate thereof,
wherein:
  $W_1$ is selected from N and $CR_1$;
  $W_2$ is selected from N and $CR_2$;
  $W_3$ is selected from N and $CR_3$;
  $W_4$ is selected from N and $CR_4$;
  each W may be the same or different from each other;
  A is selected from N and CH;
  $R_1$, $R_2$, $R_3$, and $R_4$ are independently selected from hydrogen, alkyl, alkenyl, alkynyl, alkoxy, thioalkyl, aryloxy, aryl, amino, hydroxyl, and halogen;
  two adjacent substituents selected from $R_1$, $R_2$, $R_3$, and $R_4$ may be connected in a 5- or 6-membered ring to form a bicyclic carbocycle or bicyclic heterocycle;
  AR1 is a group selected from the following:

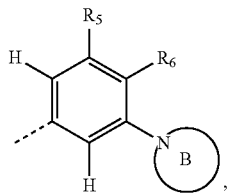

(i)

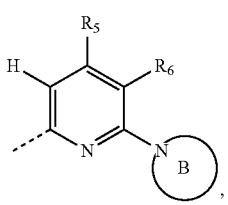

(ii)

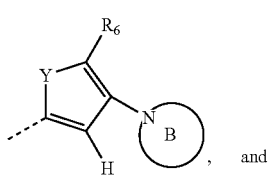

, and (iii)

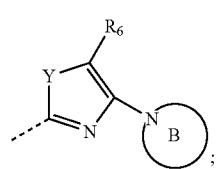

;

(iv)

B is a group selected from the following:

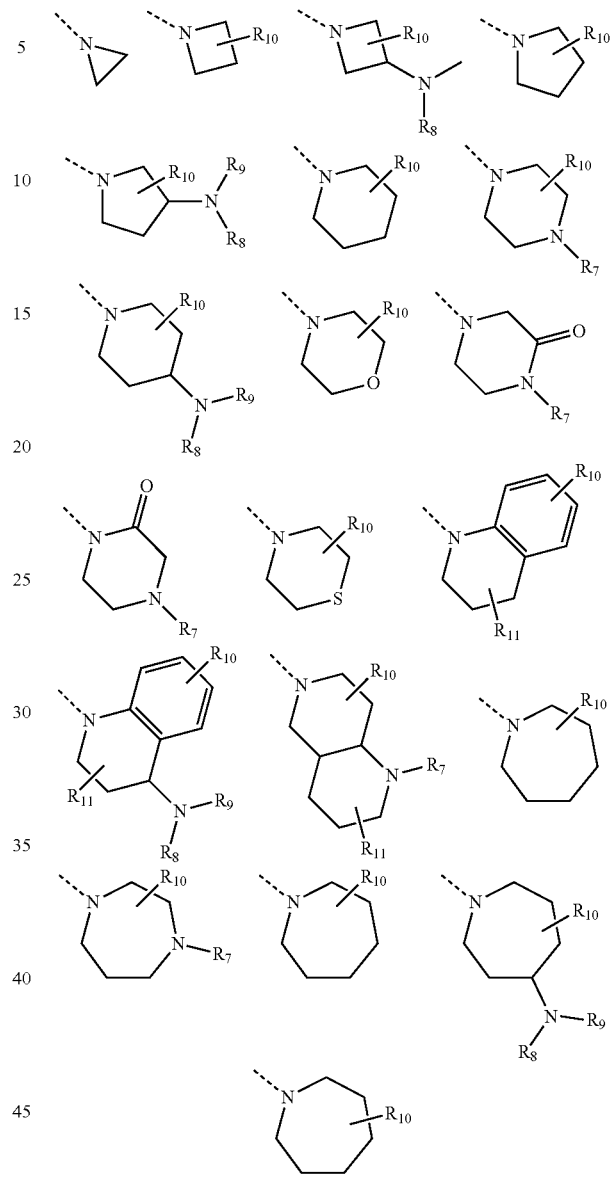

each ring system may be substituted with one or more substituents independently selected from $R_{10}$ and $R_{11}$;
  $R_5$ is selected from hydrogen, alkoxy, alkyl, thioalkyl, aryloxy, aryl, hydroxyl, and halogen;
  $R_6$ is selected from hydrogen, alkoxy, alkyl, thioalkyl, aryloxy, aryl, and halogen;
  $R_7$ is selected from hydrogen, alkyl, —SO2$R_{12}$, —C(O)NR$_{12}$R$_{13}$, —C(O)R$_{12}$;
  $R_8$ and $R_9$ are independently selected from hydrogen, aryl, alkenyl, alkyl, —SO$_2$R$_{12}$, —C(O)NR$_{12}$R$_{13}$, —C(O)R$_{12}$;
  $R_{10}$ and $R_{11}$ are independently selected from hydrogen, halogen, alkyl, alkoxy, aryl, and hydroxyl;
  $R_{12}$ and $R_{13}$ are independently selected from hydrogen, aryl, and alkyl;
  Y is selected from NH, O, and S; and
  two adjacent substituents selected from $R_5$, $R_6$, $R_8$, $R_9$, $R_{10}$, and $R_{11}$ may be connected in a 5- or 6-membered ring to form a carbocycle or heterocycle.

In another aspect of the present disclosure, there is provided a pharmaceutical composition comprising a compound of Formula I, or a pharmaceutically acceptable salt thereof and one or more pharmaceutically acceptable carriers, diluents or excipients.

In yet another aspect of the present disclosure there is provided a compound of Formula I, or a pharmaceutically acceptable salt thereof for use in therapy, in particular in the treatment of diseases or conditions for which a bromodomain inhibitor is indicated.

In yet another aspect of the present disclosure there is provided a compound of Formula I, or a pharmaceutically acceptable salt thereof in the manufacture of a medicament for the treatment of diseases or conditions for which a bromodomain inhibitor is indicated.

DEFINITIONS

As used in the present specification, the following words, phrases and symbols are generally intended to have the meanings as set forth below, except to the extent that the context in which they are used indicates otherwise. The following abbreviations and terms have the indicated meanings throughout:

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as $(C_2-C_8)$alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as $(C_2\text{-}C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —$NR_aC(O)(R_b)$— or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of $R_d$ or $R_e$ is an alkyl group. In some embodiments Rd and Re each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$ aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$ arylalkyl."

The term "carbamate" as used herein refers to the form —$R_gOC(O)N(R_h)$—, —$R_gOC(O)N(R_h)R_i$—, or —$OC(O)NR_hR_i$, wherein $R_g$, $R_h$ and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "$(C_3\text{-}C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_kC(O)O$—$R_j$—, or —$R_kC(O)O$—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of Rj or Rk is alkyl, such as —O—C(O)-alkyl, —C(O)—O-alkyl-, and -alkyl-C(O)—O-alkyl-. Exemplary esters also include aryl or heteroaryl esters, e.g. wherein at least one of Rj or Rk is a heteroaryl group such as pyridine, pyridazine, pyrimidine and pyrazine, such as a nicotinate ester. Exemplary esters also include reverse esters having the structure —$R_kC(O)O$—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$) or —R$_n$—C(O)—R$_o$—. The ketone can be attached to another group through Rn or R$_o$. Rn or R$_o$ can be alkyl, alkenyl, alkynyl, cycloalkyl, heterocyclyl or aryl, or Rn or R$_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "thioalkyl" as used herein refers to an alkyl group attached to a sulfur (—S-alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a "suitable substituent" refers to a group that does not nullify the synthetic or pharmaceutical utility of the compounds of the present disclosure or the intermediates useful for preparing them. Examples of suitable substituents include, but are not limited to: $C_{1-8}$ alkyl, alkenyl or alkynyl; $C_{1-6}$ aryl, $C_{2-5}$ heteroaryl; $C_{3-7}$ cycloalkyl; $C_{1-8}$ alkoxy; $C_6$ aryloxy; —CN; —OH; oxo; halo, carboxy; amino, such as —NH($C_{1-8}$ alkyl), —N($C_{1-8}$ alkyl)$_2$, —NH(($C_6$)aryl), or —N(($C_6$)aryl)$_2$; formyl; ketones, such as —CO($C_{1-8}$ alkyl), —CO(($C_6$aryl) esters, such as —CO$_2$($C_{1-8}$ alkyl) and —CO$_2$($C_6$aryl). One of skill in art can readily choose a suitable substituent based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carri-* ers in *Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted. For example, any claim to compound A below is understood to include tautomeric structure B, and vice versa, as well as mixtures thereof.

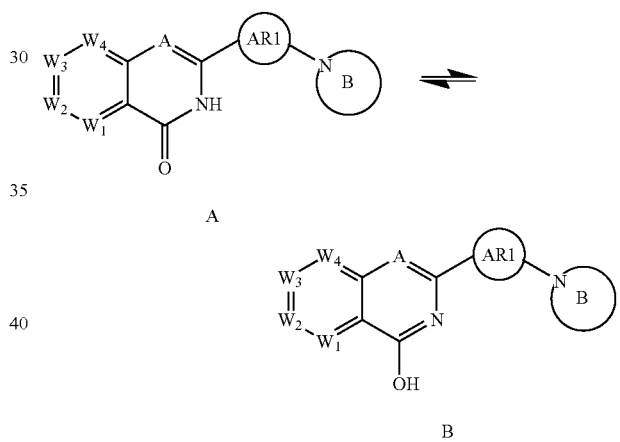

EXEMPLARY EMBODIMENTS

One embodiment of the invention provides a compound of Formula I:

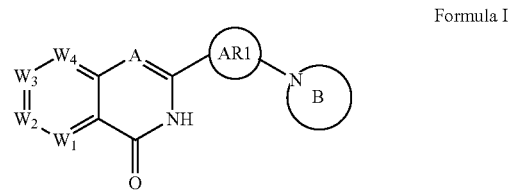

or a stereoisomer, tautomer, pharmaceutical acceptable salt, or hydrate thereof,
wherein:
$W_1$ is selected from N and $CR_1$;
$W_2$ is selected from N and $CR_2$;
$W_3$ is selected from N and $CR_3$;

$W_4$ is selected from N and $CR_4$;

each W may be the same or different from each other;

A is selected from N and CH;

$R_1$, $R_2$, $R_3$, and $R_4$ are each independently selected from hydrogen, alkyl, alkenyl, alkynyl, alkoxy, thioalkyl, aryloxy, amino, aryl, hydroxyl, and halogen, with the proviso that at least one of $R_1$-$R_4$ is not hydrogen;

two adjacent substituents selected from $R_1$, $R_2$, $R_3$, and $R_4$ may be connected in a 5- or 6-membered ring to form a bicyclic carbocycle or bicyclic heterocycle;

AR1 is a group selected from the following:

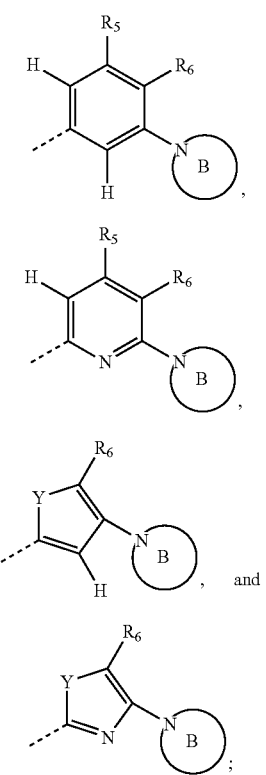

B is a group selected from the following:

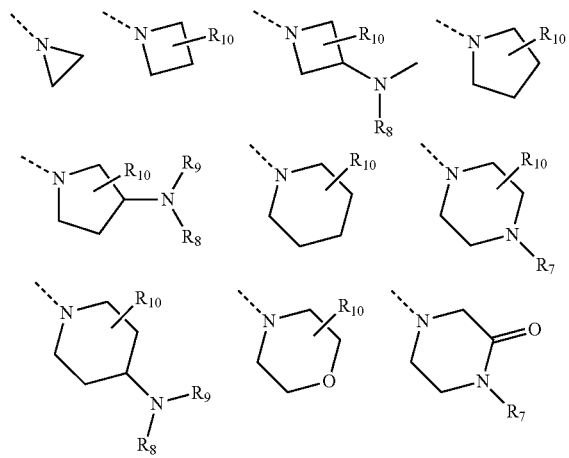

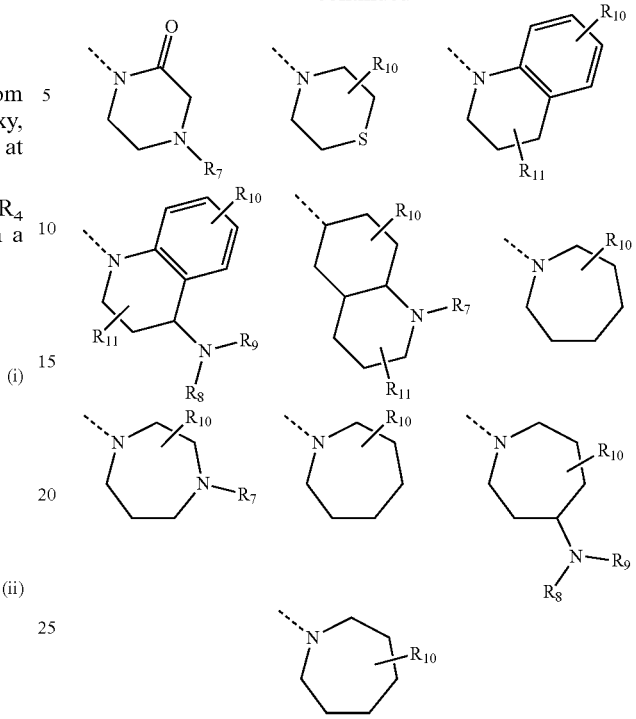

each ring system may be substituted with one or more substituents independently selected from $R_{10}$ and $R_{11}$;

$R_5$ is selected from hydrogen, alkoxy, alkyl, thioalkyl, aryloxy, aryl, hydroxyl, and halogen;

$R_6$ is selected from hydrogen, alkoxy, alkyl, thioalkyl, aryloxy, aryl, and halogen, with the proviso that if $R_6$=hydrogen, then $R_2$ is not —$NMe_2$;

$R_7$ is selected from hydrogen, alkyl, —$SO_2R_{12}$, —$C(O)NR_{12}R_{13}$, —$C(O)R_{12}$;

$R_8$ and $R_9$ are independently selected from hydrogen, aryl, alkenyl, alkyl, —$SO_2R_{12}$, —$C(O)NR_{12}R_{13}$, —$C(O)R_{12}$;

$R_{10}$ and $R_{11}$ are independently selected from hydrogen, halogen, alkyl, alkoxy, aryl, and hydroxyl;

$R_{12}$ and $R_{13}$ are independently selected from hydrogen, aryl, and alkyl;

Y is selected from NH, O, and S; and two adjacent substituents selected from $R_5$, $R_6$, $R_8$, $R_9$, $R_{10}$, and $R_{11}$ may be connected in a 5- or 6-membered ring to form a carbocycle or heterocycle.

In some embodiments, $R_1$, $R_2$, $R_3$, and $R_4$ are independently selected from hydrogen, alkyl (such as methyl and ethyl), alkoxy (such as methoxy and ethoxy), halogen (such as fluoride), and amino.

In some embodiments, $R_1$, $R_2$, $R_3$, and $R_4$ are each independently selected from alkyl, alkoxy, or thioalkyl, each of which may be optionally substituted with hydroxyl, amino, halogen, or ester.

In some embodiments, $R_1$, $R_2$, $R_3$, and $R_4$ are each independently selected from alkenyl or alkynyl, each of which may be optionally substituted with halogen.

In some embodiments, $R_1$, $R_2$, $R_3$, and $R_4$ are each independently selected from aryl or aryloxy, each of which may be optionally substituted with halogen, alkoxy, or amino.

In certain embodiments, $R_1$ and $R_3$ in the compound of Formula I are independently selected from alkoxy (such as methoxy), halogen (such as fluoride), and amino (such as a substituted piperazine).

In other embodiments, $R_1$ and $R_3$ are independently selected from alkoxy.

In an exemplary compound of Formula I, $R_1$ and $R_3$ are methoxy and $R_2$ and $R_4$ are hydrogen.

In some embodiments $R_5$ is selected from hydrogen, alkyl (such as methyl, ethyl, propyl, and isopropyl), alkoxy (such as methoxy, ethoxy, propoxy, and isopropoxy, —$OCF_3$), halogen (such as fluoride and chloride).

In some embodiments $R_5$ is selected from alkoxy, alkyl, or thioalkyl, each of which may be optionally substituted with halogen, alkoxy, or hydroxyl.

some embodiments $R_5$ is selected from aryl or aryloxy, each of which may be optionally substituted with halogen or alkoxy.

In other embodiments $R_5$ in compounds of Formula I is selected from hydrogen, methoxy, ethoxy, —$OCF_3$, fluoride, chloride, methyl, and ethyl.

In exemplary embodiments $R_6$ in the compound of Formula I is selected from hydrogen and alkoxy.

In other embodiments $R_6$ is selected from hydrogen, methoxy, ethoxy, or alkoxy optionally substituted with a hydroxyl or amino.

In some embodiments $R_6$ is selected from alkyl, alkoxy, or thioalkyl, each of which may be optionally substituted with halogen, amino, hydroxyl, or alkoxy.

some embodiments $R_6$ is selected from aryl or aryloxy, each of which may be optionally substituted with halogen, alkoxy, or amino.

In certain embodiments $R_6$ is selected from hydrogen, methoxy,

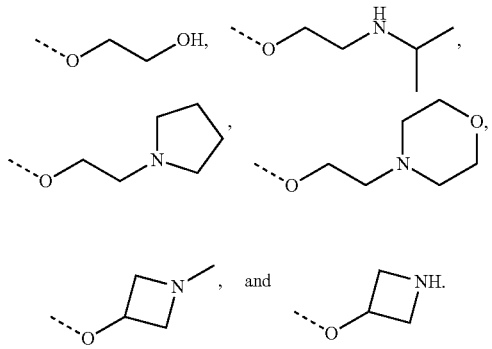

In some embodiments Y is N.

In exemplary embodiments of compounds of Formula I, AR1 is selected from (i)

(ii)

In some embodiments, AR1 in the compound of Formula I is

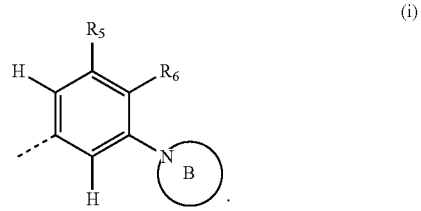

(i)

In alternate embodiments, AR1 is

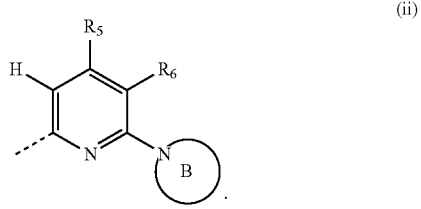

(ii)

In certain exemplary compounds of Formula I, B is selected from

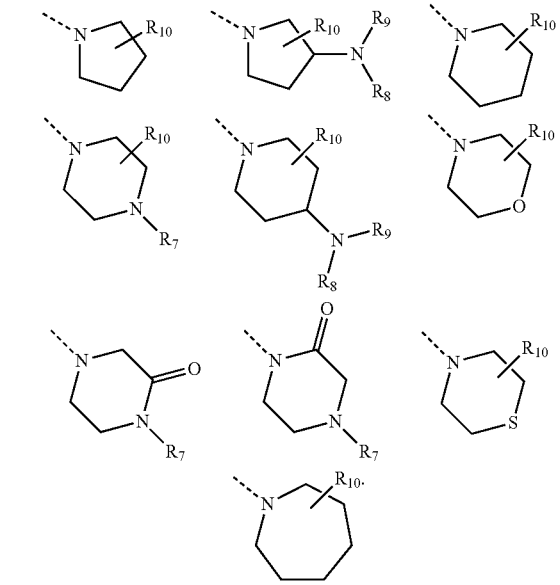

In some exemplary compounds of Formula I, B is selected from

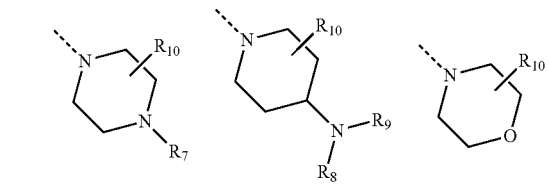

-continued

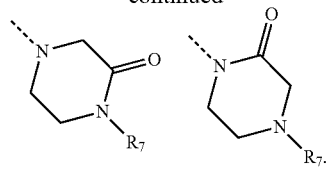

In some embodiments, B is

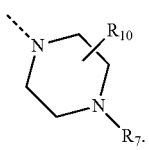

In some embodiments R$_7$ in the compounds of Formula I is selected from hydrogen and alkyl.

In some embodiments R$_7$ is alkyl optionally substituted with halogen, alkoxy, or amino.

In exemplary compounds of Formula I, R$_8$ and R$_9$ are independently selected from hydrogen and alkyl (such as methyl and ethyl).

In some embodiments R$_8$ and R$_9$ are each selected from aryl, alkyl, or alkenyl, each of which may be optionally substituted with halogen, hydroxyl, cyano, amido, sulfone, sulfonamide, heterocycle, or phosphate.

In exemplary embodiments R$_{10}$ and R$_{11}$ are independently selected from hydrogen and halogen.

In some embodiments R$_{10}$ and R$_{11}$ are each selected from alkyl, alkoxy, or aryl, each of which may be optionally substituted with halogen.

In certain compounds of Formula I R$_{10}$ and R$_{11}$ are hydrogen.

In other exemplary embodiments, R$_{12}$ and R$_{13}$ are independently selected from hydrogen and alkyl.

In some embodiments R$_{12}$ and R$_{13}$ are each selected from alkyl or aryl, each of which may be optionally substituted with halogen.

In other compounds of Formula I, R$_{12}$ and R$_{13}$ are independently selected from hydrogen, methyl, ethyl, propyl, and isopropyl.

In certain embodiments of the invention, the compound of Formula I is selected from:
2-(3-(4-Isopropylpiperazin-1-yl)phenyl)-5,7-dimethoxyquinazolin-4(3H)-one [Example 1],
2-(3-(4-Isopropylpiperazin-1-yl)-5-methoxyphenyl)-5,7-dimethoxyquinazolin-4(3H)-one [Example 2],
5,7-Dimethoxy-2-(6-(4-(2-methoxyethyl)piperazin-1-yl)pyridin-2-yl)quinazolin-4(3H)-one [Example 3],
2-(6-(4-(2-Hydroxyethyl)piperazin-1-yl)pyridin-2-yl)-5,7-dimethoxyquinazolin-4(3H)-one [Example 4],
2-(6-(4-Isobutylpiperazin-1-yl)pyridin-2-yl)-5,7-dimethoxyquinazolin-4(3H)-one [Example 5],
5,7-Dimethoxy-2-(6-(4-(2-(methylsulfonyl)ethyl)piperazin-1-yl)pyridin-2-yl)quinazolin-4(3H)-one [Example 6],
Methyl 2-(4-(6-(5,7-dimethoxy-4-oxo-3,4-dihydroquinazolin-2-yl)pyridin-2-yl)piperazin-1-yl)acetate [Example 7],
2-(6-(4-(1-Hydroxypropan-2-yl)piperazin-1-yl)pyridin-2-yl)-5,7-dimethoxyquinazolin-4(3H)-one [Example 8],
2-(4-(6-(5,7-Dimethoxy-4-oxo-3,4-dihydroquinazolin-2-yl)pyridin-2-yl)piperazin-1-yl)propanamide [Example 9],
2-(4-(6-(5,7-Dimethoxy-4-oxo-3,4-dihydroquinazolin-2-yl)pyridin-2-yl)piperazin-1-yl)acetic acid [Example 10],
3-(4-(6-(5,7-Dimethoxy-4-oxo-3,4-dihydroquinazolin-2-yl)pyridin-2-yl)piperazin-1-yl)propanoic acid [Example 11],
2-(5-(2-(Isopropylamino)ethoxy)-6-(4-isopropylpiperazin-1-yl)pyridin-2-yl)-5,7-dimethoxyquinazolin-4(3H)-one bis(trifluoroacetate) [Example 12],
2-(5-(2-Hydroxyethoxy)-6-(4-isopropylpiperazin-1-yl)pyridin-2-yl)-5,7-dimethoxyquinazolin-4(3H)-one acetate [Example 13],
2-(6-(4-Isopropylpiperazin-1-yl)-5-methoxypyridin-2-yl)-5,7-dimethoxyquinazolin-4(3H)-one [Example 14],
5,7-Dimethoxy-2-(6-(4-methylpiperazin-1-yl)pyridin-2-yl)quinazolin-4(3H)-one Hydrochloride (Example 15),
5,7-Dimethoxy-2-(6-morpholinopyridin-2-yl)quinazolin-4(3H)-one Hydrochloride (Example 16),
2-(6-(4-Isopropylpiperazin-1-yl)pyridin-2-yl)-5,7-dimethoxyquinazolin-4(3H)-one Hydrochloride (Example 17),
5,7-Dimethoxy-2-(6-(4-(methylsulfonyl)piperazin-1-yl)pyridin-2-yl)quinazolin-4(3H)-one Hydrochloride (Example 18),
5,7-Dimethoxy-2-(6-(4-propionylpiperazin-1-yl)pyridin-2-yl)quinazolin-4(3H)-one dihydrochloride (Example 19),
2-(3-(4-Isopropylpiperazin-1-yl)-5-(trifluoromethoxy)phenyl)-5,7-dimethoxyquinazolin-4(3H)-one (Example 20),
7-Fluoro-2-(6-(4-isopropylpiperazin-1-yl)pyridin-2-yl)-5-methoxyquinazolin-4(3H)-one Hydrochloride (Example 21),
7-(Benzyloxy)-2-(6-(4-isopropylpiperazin-1-yl)pyridin-2-yl)-5-methoxyquinazolin-4(3H)-one Hydrochloride (Example 22),
7-(4-Isopropylpiperazin-1-yl)-2-(6-(4-isopropylpiperazin-1-yl)pyridin-2-yl)-5-methoxyquinazolin-4(3H)-one Hydrochloride (Example 23),
2-(6-(4-Isopropylpiperazin-1-yl)pyridin-2-yl)-5-methoxy-7-phenylquinazolin-4(3H)-one (Example 25),
8-(Benzyloxy)-2-(3-(4-isopropylpiperazin-1-yl)phenyl)-5-methoxyquinazolin-4(3H)-one (Example 26),
4-(6-(5,7-Dimethoxy-4-oxo-3,4-dihydroquinazolin-2-yl)pyridin-2-yl)-N-isopropylpiperazine-1-carboxamide Hydrochloride (Example 27),
2-(6-(4-Isopropyl-2-oxopiperazin-1-yl)pyridin-2-yl)-5,7-dimethoxyquinazolin-4(3H)-one Hydrochloride (Example 28),
2-(6-(4-(Dimethylamino)piperidin-1-yl)pyridin-2-yl)-5,7-dimethoxyquinazolin-4(3H)-one (Example 29),
5,7-Dimethoxy-2-(6-(4-methyl-3-oxopiperazin-1-yl)pyridin-2-yl)quinazolin-4(3H)-one (Example 30),
2-(3-Chloro-5-(piperazin-1-yl)phenyl)-5,7-dimethoxyquinazolin-4(3H)-one (Example 31),
2-(3-Chloro-5-(4-isopropylpiperazin-1-yl)phenyl)-5,7-dimethoxyquinazolin-4(3H)-one (Example 32).

In certain embodiments, the compound of Formula I is 2-(6-(4-Isopropylpiperazin-1-yl)pyridin-2-yl)-5,7-dimethoxyquinazolin-4(3H)-one Hydrochloride (Example 17).

In selected embodiments of the compounds of Formula I, R$_6$ is selected from the group represented by Formula II:

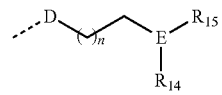

wherein:
D is selected from O and S;
E is selected from O, N, and S;

$R_{14}$ and $R_{15}$ are independently selected from hydrogen, alkyl, and cycloalkyl, and only one of $R_{14}$ and $R_{15}$ are present if E is O or S; and n is selected from 1, 2, and 3. In some embodiments, D is oxygen. In some embodiments, n=1. In some embodiments, $R_{14}$ and $R_{15}$ are independently selected from hydrogen, and alkyl (such as C1-C5).

In some embodiments $R_{14}$ and $R_{15}$ are each selected from alkyl or cycloalkyl, each of which may be optionally substituted with halogen, amino, or hydroxyl.

In certain compounds of Formula I, $R_6$ is selected from hydrogen, methoxy,

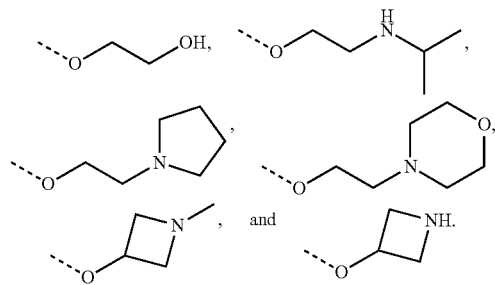

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formula I.

In one embodiment, because of potent effects of BET inhibitors in vitro on IL-6 and IL-17 transcription, BET inhibitor compounds of Formula I are used as therapeutics for inflammatory disorders in which IL-6 and/or IL-17 have been implicated as drivers of disease. The following autoimmune diseases are amenable to therapeutic use of BET inhibition by administration of a compound of Formula I because of a prominent role of IL-6 and/or IL-17: Acute Disseminated Encephalomyelitis [69], Agammaglobulinemia [70], Allergic Disease [71], Ankylosing spondylitis [72], Anti-GBM/Anti-TBM nephritis [73], Anti-phospholipid syndrome [74], Autoimmune aplastic anemia [75], Autoimmune hepatitis [76], Autoimmune inner ear disease [77], Autoimmune myocarditis [78], Autoimmune pancreatitis [79], Autoimmune retinopathy [80], Autoimmune thrombocytopenic purpura [81], Behcet's Disease [82], Bullous pemphigoid [83], Castleman's Disease [84], Celiac Disease [85], Churg-Strauss syndrome [86], Crohn's Disease [87], Cogan's syndrome [88], Dry eye syndrome [89], Essential mixed cryoglobulinemia [90], Dermatomyositis [91], Devic's Disease [92], Encephalitis [93], Eosinophlic esophagitis [94], Eosinophilic fasciitis [94], Erythema nodosum [95], Giant cell arteritis [96], Glomerulonephritis [97], Goodpasture's syndrome [73], Granulomatosis with Polyangiitis (Wegener's) [98], Graves' Disease[99], Guillain-Barre syndrome [100], Hashimoto's thyroiditis [101], Hemolytic anemia [102], Henoch-Schonlein purpura [103], IgA nephropathy [104], Inclusion body myositis [105], Type I diabetes [8], Interstitial cystitis [106], Kawasaki's Disease[107], Leukocytoclastic vasculitis [108], Lichen planus [109], Lupus (SLE) [110], Microscopic polyangitis [111], Multiple sclerosis [112], Myasthenia gravis [113], myositis [91], Optic neuritis [114], Pemphigus [115], POEMS syndrome [116], Polyarteritis nodosa [117], Primary biliary cirrhosis [118], Psoriasis [119], Psoriatic arthritis [120], Pyoderma gangrenosum [121], Relapsing polychondritis [122], Rheumatoid arthritis [123], Sarcoidosis [124], Scleroderma [125], Sjogren's syndrome [126], Takayasu's arteritis [127], Transverse myelitis [128], Ulcerative colitis [129], Uveitis [130], Vitiligo [131].

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis [132], pneumonitis [133], osteomyelitis [134], gastritis [135], enteritis [136], gingivitis [137], appendicitis [138], irritable bowel syndrome [139], tissue graft rejection [140], chronic obstructive pulmonary disease (COPD) [141], septic shock (toxic shock syndrome, SIRS, bacterial sepsis, etc) [12], osteoarthritis [142], acute gout [143], acute lung injury [141], acute renal failure [144], burns [145], Herxheimer reaction [146], and SIRS associated with viral infections [8].

In one embodiment, BET inhibitor compounds of Formula I are used for treating rheumatoid arthritis (RA) and multiple sclerosis (MS). Strong proprietary data exist for the utility of BET inhibitors in preclinical models of RA and MS [17]. Both RA and MS are characterized by a dysregulation of the IL-6 and IL-17 inflammatory pathways [10] and thus would be especially sensitive to BET inhibition. In another embodiment, BET inhibitor compounds of Formula I are used for treating sepsis and associated afflictions. BET inhibition has been shown to inhibit development of sepsis, in part, by inhibiting IL-6 expression, in preclinical models in both published [12] and proprietary data.

In one embodiment, BET inhibitor compounds of Formula I are used to treat cancer. Cancers that have an overexpression, translocation, amplification, or rearrangement c-myc or other myc family oncoproteins (MYCN, L-myc) are particularly sensitive to BET inhibition [27, 28]. These cancers include, but are not limited to, B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, Small cell lung carcinoma [25].

In one embodiment, BET inhibitor compounds of Formula I are used to treat cancers that result from an aberrant regulation (overexpression, translocation, etc) of BET proteins. These include, but are not limited to, NUT midline carcinoma (Brd3 or Brd4 translocation to nutlin 1 gene) [22], B-cell lymphoma (Brd2 overexpression) [23], non-small cell lung cancer (BrdT overexpression) [147, 148], esophageal cancer and head and neck squamous cell carcinoma (BrdT overexpression) [147], colon cancer (Brd4) [149].

In one embodiment, because BET inhibitors decrease Brd-dependent recruitment of pTEFb to genes involved in cell proliferation, BET inhibitor compounds of Formula I are used to treat cancers that rely on pTEFb (Cdk9/cyclin T) and BET proteins to regulate oncogenes. These include, but are not limited to, chronic lymphocytic leukemia and multiple myeloma [150], follicular lymphoma, diffuse large B cell lymphoma with germinal center phenotype, Burkitt's lymphoma, Hodgkin's lymphoma, follicular lymphomas and activated, anaplastic large cell lymphoma [151], neuroblastoma and primary neuroectodermal tumor [152], rhabdomyosarcoma [153], prostate cancer [154], and breast cancer [45].

In one embodiment, BET inhibitor compounds of Formula I are used to treat cancers in which BET-responsive genes, such as CDK6, Bcl2, TYRO3, MYB, and hTERT are up-regulated [26, 27]. These cancers include, but are not limited to, pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, renal carcinoma [32, 155-162].

Published and proprietary data have shown direct effects of BET inhibition on cell proliferation in various cancers. In one embodiment, BET inhibitor compounds of Formula I are used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), non-Hodgkin's lymphoma [24, 26-30, 33]. Examples provided within this application have also shown a direct effect of BET inhibition on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formula I are combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimrus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), WP1130 (Degrasyn).

In one embodiment, because of their ability to up-regulate ApoA-1 transcription and protein expression [11, 35], BET inhibitor compounds of Formula I are used to treat cardiovascular diseases that are generally associated with including dyslipidemia, atherosclerosis, hypercholesterolemia, and metabolic syndrome [8, 19]. In another embodiment, BET inhibitor compounds of Formula I are used to treat non-cardiovascular disease characterized by deficits in ApoA-1, including Alzheimer's disease [37].

In one embodiment, BET inhibitor compounds of Formula I are used in patients with insulin resistance and type II diabetes [8, 19, 38, 39]. The anti-inflammatory effects of BET inhibition would have additional value in decreasing inflammation associated with diabetes and metabolic disease [163].

In one embodiment, because of their ability to down-regulate viral promoters, BET inhibitor compounds of Formula I are used as therapeutics for cancers that are associated with viruses including Epstein-Barr Virus (EBV), hepatitis virus (HBV, HCV), Kaposi's sarcoma associated virus (KSHV), human papilloma virus (HPV), Merkel cell polyomavirus, and human cytomegalovirus (CMV) [40-42, 164]. In another embodiment, because of their ability to reactivate HIV-1 in models of latent T cell infection and latent monocyte infection, BET inhibitors could be used in combination with antiretroviral therapeutics for treating HIV [43-46].

In one embodiment, because of the role of epigenetic processes and bromodomain-containing proteins in neurological disorders, BET inhibitor compounds of Formula I are used to treat diseases including, but not limited to, Alzheimer's disease, Parkinson's disease, Huntington disease, bipolar disorder, schizophrenia, Rubinstein-Taybi syndrome, and epilepsy [9, 165].

In one embodiment, because of the effect of BRDT depletion or inhibition on spermatid development, BET inhibitor compounds of Formula I are used as reversible, male contraceptive agents [50, 51].

Pharmaceutical Compositions

Pharmaceutical compositions of the present disclosure comprise at least one compound of Formula I, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula I or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4): 219-244 (1966) and the following Table for Equivalent Surface Area Dosage Factors).

Equivalent Surface Area Dosage Factors:

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

Specific embodiments of the invention include:

1. A compound of Formula I:

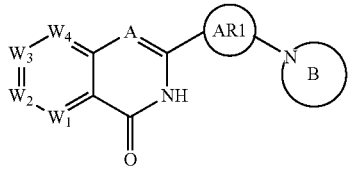

Formula I or a stereoisomer, tautomer, pharmaceutical acceptable salt, or hydrate thereof,
wherein:
  $W_1$ is selected from N and $CR_1$;
  $W_2$ is selected from N and $CR_2$;
  $W_3$ is selected from N and $CR_3$;
  $W_4$ is selected from N and $CR_4$;
  each W may be the same or different from each other;
  A is selected from N and CH;
  $R_1$, $R_2$, $R_3$, and $R_4$ are each independently selected from hydrogen, alkyl, alkenyl, alkynyl, alkoxy, thioalkyl, aryloxy, aryl, amino, hydroxyl, and halogen;
  two adjacent substituents selected from $R_1$, $R_2$, $R_3$, and $R_4$ may be connected in a 5- or 6-membered ring to form a bicyclic carbocycle or bicyclic heterocycle;
  AR1 is a group selected from the following:

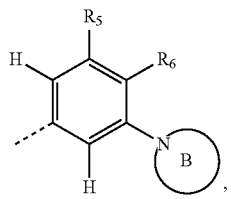

(i)

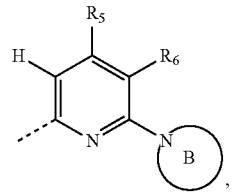

(ii)

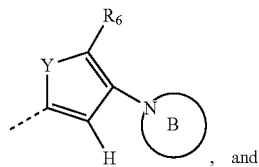

(iii)

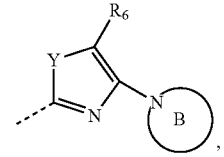

(iv)

B is a group selected from the following:

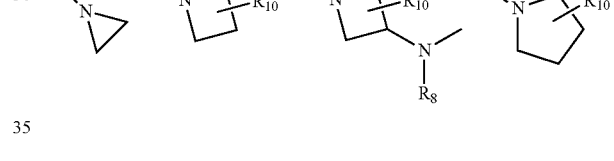

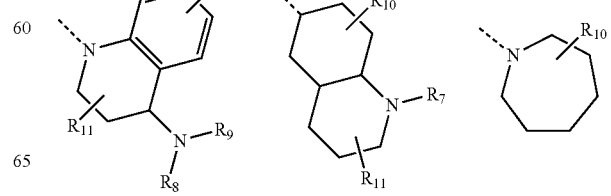

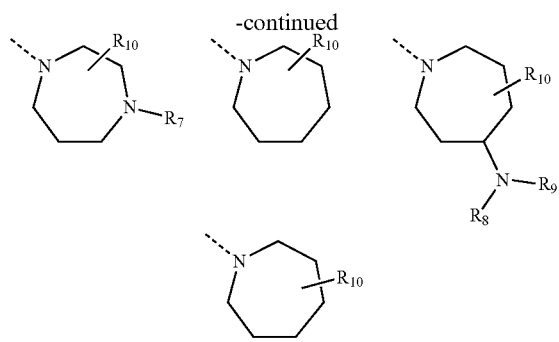

each ring system may be substituted with one or more substituents independently selected from $R_{10}$ and $R_{11}$;

$R_5$ is selected from hydrogen, alkoxy, alkyl, thioalkyl, aryloxy, aryl, hydroxyl, and halogen;

$R_6$ is selected from hydrogen, alkoxy, alkyl, thioalkyl, aryloxy, aryl, and halogen;

$R_7$ is selected from hydrogen, alkyl, —$SO_2R_{12}$, —$C(O)NR_{12}R_{13}$, —$C(O)R_{12}$;

$R_8$ and $R_9$ are independently selected from hydrogen, aryl, alkenyl, alkyl, —$SO_2R_{12}$, —$C(O)NR_{12}R_{13}$, —$C(O)R_{12}$;

$R_{10}$ and $R_{11}$ are independently selected from hydrogen, halogen, alkyl, alkoxy, aryl, and hydroxyl;

$R_{12}$ and $R_{13}$ are independently selected from hydrogen, aryl, and alkyl;

Y is selected from NH, O, and S; and two adjacent substituents selected from $R_5$, $R_6$, $R_8$, $R_9$, $R_{10}$, and $R_{11}$ may be connected in a 5- or 6-membered ring to form a carbocycle or heterocycle.

2. The compound according to embodiment 1 wherein if $R_6$ is hydrogen, then $R_2$ is not —$NMe_2$.

3. The compound according to embodiment 1 wherein $R_1$, $R_2$, $R_3$, and $R_4$ are independently selected from hydrogen, alkyl, alkoxy, halogen, and amino.

4. The compound according to embodiment 1, wherein at least one of $R_1$-$R_4$ is not hydrogen.

5. The compound according to embodiment 1 wherein $R_1$ and $R_3$ are independently selected from alkoxy, halogen, and amino.

6. The compound according to embodiment 1 wherein $R_1$ and $R_3$ are independently selected methoxy, fluoride, and a substituted piperazine.

7. The compound according to embodiment 1 wherein $R_1$ and $R_3$ are independently selected from alkoxy.

8. The compound according to embodiment 1 wherein $R_1$ and $R_3$ are methoxy and $R_2$ and $R_4$ are hydrogen.

9. The compound according to any one of embodiments 1-8 wherein $R_5$ is selected from hydrogen, alkyl, alkoxy, and halogen.

10. The compound according to embodiment 9 wherein $R_5$ is selected from hydrogen, methyl, ethyl propyl, and isopropyl, methoxy, ethoxy, propoxy, isopropoxy, —$OCF_3$, fluoride, and chloride.

11. The compound according to any one of embodiments 1-8 wherein $R_5$ is selected from hydrogen, methoxy, ethoxy, —$OCF_3$, fluoride, chloride, methyl, and ethyl.

12. The compound according to any one of embodiments 1-11 wherein $R_6$ is selected from hydrogen and alkoxy optionally substituted with a hydroxyl or amino.

13. The compound according to any one of embodiments 1-11 wherein $R_6$ is selected from hydrogen, methoxy, and ethoxy.

14. The compound according to any one of embodiments 1-11 wherein $R_6$ is selected from hydrogen, methoxy,

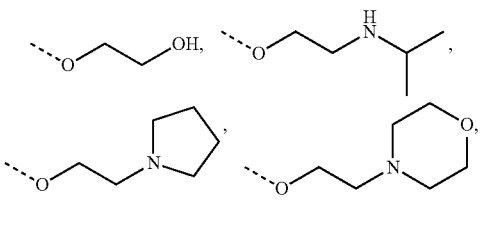

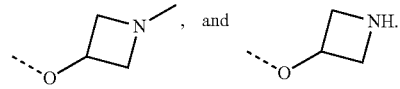

15. The compound according to any one of embodiments 1-14 wherein Y is N.

16. The compound according to any one of embodiments 1-15 wherein AR1 is selected from

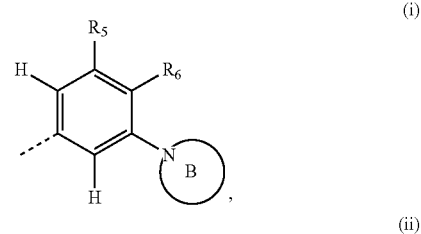

17. The compound according to any one of embodiments 1-16 wherein AR1 is

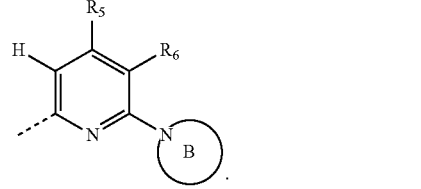

18. The compound according to any one of embodiments 1-16 wherein AR1 is

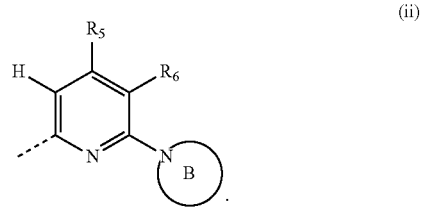

19. The compound according to any one of embodiments 1-18 wherein B is selected from

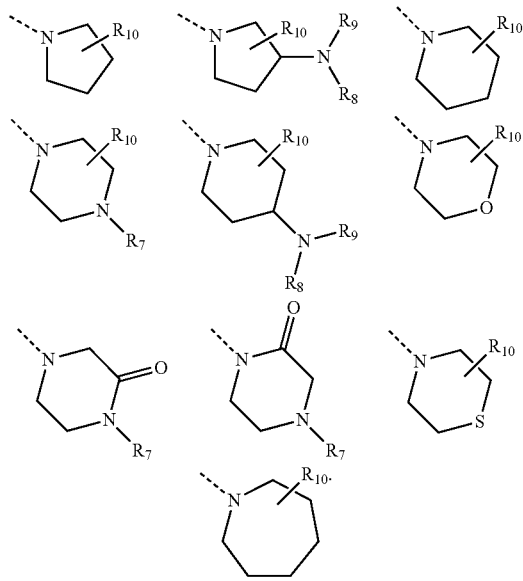

20. The compound according to any one of embodiments 1-18 wherein B is selected from

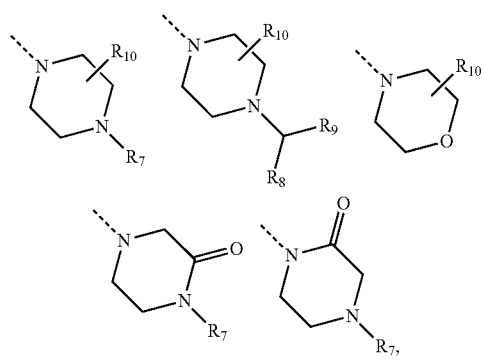

21. The compound according to embodiment 20 wherein B is

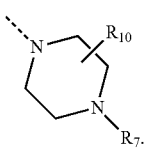

22. The compound according to any one of embodiments 1-21, wherein $R_7$ is selected from hydrogen and alkyl.

23. The compound according to any one of embodiments 1-22, wherein $R_8$ and $R_9$ are independently selected from hydrogen and alkyl.

24. The compound according to any one of embodiments 1-22, wherein $R_8$ and $R_9$ are independently selected from hydrogen, methyl, and ethyl.

25. The compound according to any one of embodiments 1-24, wherein $R_{10}$ and $R_{11}$ are independently selected from hydrogen and halogen.

26. The compound according to embodiment 25 wherein $R_{10}$ and $R_{11}$ are hydrogen.

27. The compound according to any one of embodiments 1-26 wherein $R_{12}$ and $R_{13}$ are independently selected from hydrogen and alkyl.

28. The compound according to any one of embodiments 1-26 wherein $R_{12}$ and $R_{13}$ are independently selected from hydrogen, methyl, ethyl, propyl, and isopropyl.

29. A compound according to embodiment 1 selected from:
2-(3-(4-Isopropylpiperazin-1-yl)phenyl)-5,7-dimethoxyquinazolin-4(3H)-one;
2-(3-(4-Isopropylpiperazin-1-yl)-5-methoxyphenyl)-5,7-dimethoxyquinazolin-4(3H)-one;
5,7-Dimethoxy-2-(6-(4-(2-methoxyethyl)piperazin-1-yl)pyridin-2-yl)quinazolin-4(3H)-one;
2-(6-(4-(2-Hydroxyethyl)piperazin-1-yl)pyridin-2-yl)-5,7-dimethoxyquinazolin-4(3H)-one;
2-(6-(4-Isobutylpiperazin-1-yl)pyridin-2-yl)-5,7-dimethoxyquinazolin-4(3H)-one;
5,7-Dimethoxy-2-(6-(4-(2-(methylsulfonyl)ethyl)piperazin-1-yl)pyridin-2-yl)quinazolin-4(3H)-one;
Methyl 2-(4-(6-(5,7-dimethoxy-4-oxo-3,4-dihydroquinazolin-2-yl)pyridin-2-yl)piperazin-1-yl)acetate;
2-(6-(4-(1-Hydroxypropan-2-yl)piperazin-1-yl)pyridin-2-yl)-5,7-dimethoxyquinazolin-4(3H)-one;
2-(4-(6-(5,7-Dimethoxy-4-oxo-3,4-dihydroquinazolin-2-yl)pyridin-2-yl)piperazin-1-yl)propanamide;
2-(4-(6-(5,7-Dimethoxy-4-oxo-3,4-dihydroquinazolin-2-yl)pyridin-2-yl)piperazin-1-yl)acetic acid;
3-(4-(6-(5,7-Dimethoxy-4-oxo-3,4-dihydroquinazolin-2-yl)pyridin-2-yl)piperazin-1-yl)propanoic acid;
2-(5-(2-(Isopropylamino)ethoxy)-6-(4-isopropylpiperazin-1-yl)pyridin-2-yl)-5,7-dimethoxyquinazolin-4(3H)-one bis(trifluoroacetate);
2-(5-(2-Hydroxyethoxy)-6-(4-isopropylpiperazin-1-yl)pyridin-2-yl)-5,7-dimethoxyquinazolin-4(3H)-one acetate;
2-(6-(4-Isopropylpiperazin-1-yl)-5-methoxypyridin-2-yl)-5,7-dimethoxyquinazolin-4(3H)-one;
5,7-Dimethoxy-2-(6-(4-methylpiperazin-1-yl)pyridin-2-yl)quinazolin-4(3H)-one Hydrochloride;
5,7-Dimethoxy-2-(6-morpholinopyridin-2-yl)quinazolin-4(3H)-one Hydrochloride;
2-(6-(4-Isopropylpiperazin-1-yl)pyridin-2-yl)-5,7-dimethoxyquinazolin-4(3H)-one Hydrochloride;
5,7-Dimethoxy-2-(6-(4-(methylsulfonyl)piperazin-1-yl)pyridin-2-yl)quinazolin-4(3H)-one Hydrochloride;
5,7-Dimethoxy-2-(6-(4-propionylpiperazin-1-yl)pyridin-2-yl)quinazolin-4(3H)-one dihydrochloride;
2-(3-(4-Isopropylpiperazin-1-yl)-5-(trifluoromethoxy)phenyl)-5,7-dimethoxyquinazolin-4(3H)-one;
7-Fluoro-2-(6-(4-isopropylpiperazin-1-yl)pyridin-2-yl)-5-methoxyquinazolin-4(3H)-one Hydrochloride;
7-(Benzyloxy)-2-(6-(4-isopropylpiperazin-1-yl)pyridin-2-yl)-5-methoxyquinazolin-4(3H)-one Hydrochloride;
7-(4-Isopropylpiperazin-1-yl)-2-(6-(4-isopropylpiperazin-1-yl)pyridin-2-yl)-5-methoxyquinazolin-4(3H)-one Hydrochloride;
2-(6-(4-Isopropylpiperazin-1-yl)pyridin-2-yl)-5-methoxy-7-phenylquinazolin-4(3H)-one;
8-(Benzyloxy)-2-(3-(4-isopropylpiperazin-1-yl)phenyl)-5-methoxyquinazolin-4(3H)-one;
4-(6-(5,7-Dimethoxy-4-oxo-3,4-dihydroquinazolin-2-yl)pyridin-2-yl)-N-isopropylpiperazine-1-carboxamide Hydrochloride;
2-(6-(4-Isopropyl-2-oxopiperazin-1-yl)pyridin-2-yl)-5,7-dimethoxyquinazolin-4(3H)-one Hydrochloride;

2-(6-(4-(Dimethylamino)piperidin-1-yl)pyridin-2-yl)-5,7-dimethoxyquinazolin-4(3H)-one;
5,7-Dimethoxy-2-(6-(4-methyl-3-oxopiperazin-1-yl)pyridin-2-yl)quinazolin-4(3H)-one;
2-(3-Chloro-5-(piperazin-1-yl)phenyl)-5,7-dimethoxyquinazolin-4(3H)-one;
2-(3-Chloro-5-(4-isopropylpiperazin-1-yl)phenyl)-5,7-dimethoxyquinazolin-4(3H)-one.

30. A compound of embodiment 1, wherein the compound is 2-(6-(4-Isopropylpiperazin-1-yl)pyridin-2-yl)-5,7-dimethoxyquinazolin-4(3H)-one Hydrochloride.

31. A compound according to any one of embodiments 1-11 and 15-28 wherein $R_6$ is selected from the group represented by Formula II:

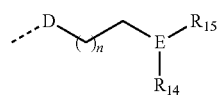

wherein:
D is selected from O and S;
E is selected from O, N, and S;
$R_{14}$ and $R_{15}$ are independently selected from hydrogen, alkyl, and cycloalkyl, wherein if E is O or S, only one of $R_{14}$ and $R_{15}$ is present; and
n is selected from 1, 2, and 3.

32. The compound according to embodiment 31 wherein D is oxygen.

33. The compound according to embodiment 31 or embodiment 32 wherein n=1.

34. The compound according to any one of embodiments 31-33 wherein $R_{14}$ and $R_{15}$ are independently selected from hydrogen, and alkyl.

35. The compound according to embodiment 34, wherein $R_{14}$ and $R_{15}$ are independently selected from hydrogen, and C1-C5 alkyl.

36. The compound according to any one of embodiments 31-35 wherein $R_6$ is selected from hydrogen, methoxy,

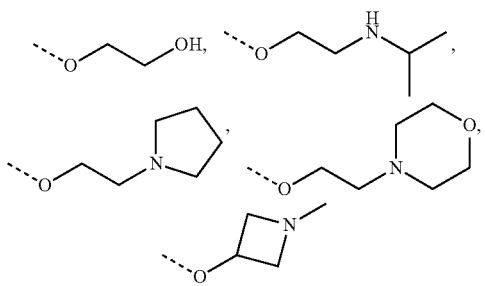

, and

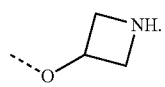

37. A pharmaceutical composition comprising a compound according to any one of embodiments 1-36.

38. A compound according to any one of embodiments 1-36 for use as a medicament.

39. A method for inhibiting BET proteins in a mammal comprising administering a therapeutically effective amount of a compound according to any one of embodiments 1-36.

40. A method for treating a disease that is sensitive to a BET inhibitor comprising administering a therapeutically effective amount of a compound according to any one of embodiments 1-36.

41. A method for treating an autoimmune disease in a mammal comprising administering a therapeutically effective amount of a compound according to any one of embodiments 1-36.

42. The method of embodiment 41, wherein the autoimmune disease is selected from Acute Disseminated Encephalomyelitis, Agammaglobulinemia, Allergic Disease, Ankylosing spondylitis, Anti-GBM/Anti-TBM nephritis, Antiphospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Lupus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

43. A method for treating inflammatory diseases or disorders in a mammal comprising administering a therapeutically effective amount of a compound according to any one of embodiments 1-36.

44. The method of embodiment 43 wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

45. A method for treating or preventing a cancer in a mammal comprising administering a therapeutically effective amount of a compound according to any one of embodiments 1-36.

46. The method of embodiment 45 wherein the cancer is a midline carcinoma.

47. The method of embodiment 45 wherein the cancer exhibits overexpression, translocation, amplification, or rearrangement of a myc family oncoproteins.

48. The method of embodiment 45 wherein the cancer is characterized by overexpression of c-myc.

49. The method of embodiment 45 wherein the cancer is characterized by is characterized by overexpression n-myc.

50. The method of embodiment 45 wherein the cancer results from aberrant regulation of BET proteins.

51. The method of embodiment 45 wherein the cancer is characterized by recruitment of pTEFb to regulate oncogenes.

52. The method of embodiment 45 wherein the cancer is characterized by upregulation of CDK6, Bcl2, TYRO3, MYB and/or hTERT.

53. The method of embodiment 45 wherein the cancer is selected from: B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, nodular melanoma, neuroblastoma, oesophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, B-cell lymphoma, non-small cell lung cancer, esophageal cancer and head and neck squamous cell carcinoma, chronic lymphocytic leukemia, follicular lymphoma, diffuse large B cell lymphoma with germinal center phenotype, Burkitt's lymphoma, Hodgkin's lymphoma, follicular lymphomas, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, hepatoma, pro-myelocytic leukemia, chronic lymphocytic leukemia, and mantle cell lymphoma.

54. The method of any one of embodiments 45-53 wherein the compound of Formula I is administered in combination with another anticancer agent.

55. The method of embodiment 54, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

56. A method of treating a cardiovascular disease comprising administering a therapeutically effective amount of a compound according to any one of embodiments 1-36.

57. The method of embodiment 56, wherein the cardiovascular disease is dyslipidemia, atherosclerosis, hypercholesterolemia, or metabolic syndrome.

58. A method of treating insulin resistance diabetes comprising administering a therapeutically effective amount of a compound according to any one of embodiments 1-36.

59. A method of treating a neurological disorder comprising administering a therapeutically effective amount of a compound according to any one of embodiments 1-36.

59. The method of embodiment 58 wherein the neurological disorder is Alzheimer's disease, Parkinson's disease, Huntington disease, bipolar disorder, schizophrenia, Rubinstein-Taybi syndrome, or epilepsy.

60. A method of male contraception comprising administering a therapeutically effective amount of a compound according to any one of embodiments 1-35.

61. A method of treating HIV comprising administering a therapeutically effective amount of a compound according to any one of embodiments 1-35.

62. A method of treating a cancer associated with a viral infection comprising administering a therapeutically effective amount of a compound according to any one of embodiments 1-35.

63. The method of embodiment 62 wherein the virus is selected from Epstein-Barr Virus, hepatitis B virus, hepatitis C virus, Kaposi's sarcoma associated virus, human papilloma virus, Merkel cell polyomavirus, and human cytomegalovirus.

REFERENCES

1. Peserico, A. and C. Simone, *Physical and functional HAT/HDAC interplay regulates protein acetylation balance*. J Biomed Biotechnol, 2011. 2011: p. 371832.
2. Hoshino, I. and H. Matsubara, *Recent advances in histone deacetylase targeted cancer therapy*. Surg Today, 2010. 40(9): p. 809-15.
3. Vernarecci, S., F. Tosi, and P. Filetici, *Tuning acetylated chromatin with HAT inhibitors: a novel tool for therapy*. Epigenetics, 2010. 5(2): p. 105-11.
4. Bandyopadhyay, K., et al., *Spermidinyl-CoA-based HAT inhibitors block DNA repair and provide cancer-specific chemo-and radiosensitization*. Cell Cycle, 2009. 8(17): p. 2779-88.
5. Arif, M., et al., *Protein lysine acetylation in cellular function and its role in cancer manifestation*. Biochim Biophys Acta, 2010. 1799(10-12): p. 702-16.
6. Sanchez, R. and M. M. Zhou, *The role of human bromodomains in chromatin biology and gene transcription*. Curr Opin Drug Discov Devel, 2009. 12(5): p. 659-65.
7. Wu, S. Y. and C. M. Chiang, *The double bromodomain-containing chromatin adaptor Brd4 and transcriptional regulation*. J Biol Chem, 2007. 282(18): p. 13141-5.
8. Belkina, A. C. and G. V. Denis, *BET domain co-regulators in obesity, inflammation and cancer*. Nat Rev Cancer, 2012. 12(7): p. 465-77.
9. Prinjha, R. K., J. Witherington, and K. Lee, *Place your BETs: the therapeutic potential of bromodomains*. Trends Pharmacol Sci, 2012. 33(3): p. 146-53.
10. Kimura, A. and T. Kishimoto, *IL-6: regulator of Treg/Th17 balance*. Eur J Immunol, 2010. 40(7): p. 1830-5.
11. Mirguet, O., et al., *From ApoA1 upregulation to BET family bromodomain inhibition: discovery of I-BET151*. Bioorg Med Chem Lett, 2012. 22(8): p. 2963-7.
12. Nicodeme, E., et al., *Suppression of inflammation by a synthetic histone mimic*. Nature, 2010. 468(7327): p. 1119-23.
13. Seal, J., et al., *Identification of a novel series of BET family bromodomain inhibitors: binding mode and profile of I-BET151 (GSK1210151A)*. Bioorg Med Chem Lett, 2012. 22(8): p. 2968-72.
14. Zhang, G., et al., *Down-regulation of NF-kappaB Transcriptional Activity in HIVassociated Kidney Disease by BRD4 Inhibition*. J Biol Chem, 2012. 287(34): p. 28840-51.
15. Zhou, M., et al., *Bromodomain protein Brd4 regulates human immunodeficiency virus transcription through phosphorylation of CDK9 at threonine 29*. J Virol, 2009. 83(2): p. 1036-44.
16. Zhang, W. S., et al., *Bromodomain-Containing-Protein 4 (BRD4) Regulates RNA Polymerase 1I Serine 2 Phosphorylation in Human CD4+ T Cells*. J Biol Chem, 2012.

17. R. Jahagirdar, S. M., S. Attwell, K. G. McLure, P. R. Young, H. C. Hansen, R. Yu, K. Norek, G. S. Wagner, *An Orally Bioavailable Small Molecule RVX-297 Significantly Decreases Disease in a Mouse Model of Multiple Sclerosis (Poster Presentation)*. World Congress of Inflammation, Paris, France, 2011.
18. Bandukwala, H. S., et al., *Selective inhibition of CD4+ T-cell cytokine production and autoimmunity by BET protein and c-Myc inhibitors*. Proc Natl Acad Sci USA, 2012. 109(36): p. 14532-7.
19. Denis, G. V., *Bromodomain coactivators in cancer, obesity, type 2 diabetes, and inflammation*. Discov Med, 2010. 10(55): p. 489-99.
20. Watson, J. D., *Curing "incurable" cancer*. Cancer Discov, 2011. 1(6): p. 477-80.
21. Morin, R. D., et al., *Frequent mutation of histone-modifying genes in non-Hodgkin lymphoma*. Nature, 2011. 476 (7360): p. 298-303.
22. French, C. A., *NUT midline carcinoma*. Cancer Genet Cytogenet, 2010. 203(1): p. 16-20.
23. Greenwald, R. J., et al., *E mu-BRD2 transgenic mice develop B-cell lymphoma and leukemia*. Blood, 2004. 103 (4): p. 1475-84.
24. Filippakopoulos, P., et al., *Selective inhibition of BET bromodomains*. Nature, 2010. 468(7327): p. 1067-73.
25. Vita, M. and M. Henriksson, *The Myc oncoprotein as a therapeutic target for human cancer*. Semin Cancer Biol, 2006. 16(4): p. 318-30.
26. Dawson, M. A., et al., *Inhibition of BET recruitment to chromatin as an effective treatment for MLL-fusion leukaemia*. Nature, 2011. 478(7370): p. 529-33.
27. Delmore, J. E., et al., *BET bromodomain inhibition as a therapeutic strategy to target c-Myc*. Cell, 2011. 146(6): p. 904-17.
28. Mertz, J. A., et al., *Targeting MYC dependence in cancer by inhibiting BET bromodomains*. Proc Natl Acad Sci USA, 2011. 108(40): p. 16669-74.
29. Ott, C. J., et al., *BET bromodomain inhibition targets both c-Myc and IL7R in highrisk acute lymphoblastic leukemia*. Blood, 2012. 120(14): p. 2843-52.
30. Zuber, J., et al., *RNAi screen identifies Brd4 as a therapeutic target in acute myeloid leukaemia*. Nature, 2011. 478(7370): p. 524-8.
31. Wang, S. and P. M. Fischer, *Cyclin-dependent kinase 9: a key transcriptional regulator and potential drug target in oncology, virology and cardiology*. Trends Pharmacol Sci, 2008. 29(6): p. 302-13.
32. Ruden, M. and N. Purl, *Novel anticancer therapeutics targeting telomerase*. Cancer Treat Rev, 2012.
33. Miguel F. Segura, R. D. M., Guangtao Zhang, Weijia Zhang, Iman Osman, Ming-Ming Zhou, Eva Hernando, *BRD4 is a novel therapeutic target in melanoma (Poster Presentation)*. Cancer Research, 2012. 72(8): p. Supplement 1.
34. Roger, V. L., et al., *Heart disease and stroke statistics— 2012 update: a report from the American Heart Association*. Circulation, 2012. 125(1): p. e2-e220.
35. Chung, C. W., et al., *Discovery and characterization of small molecule inhibitors of the BET family bromodomains*. J Med Chem, 2011. 54(11): p. 3827-38.
36. Degoma, E. M. and D. J. Rader, *Novel HDL-directed pharmacotherapeutic strategies*. Nat Rev Cardiol, 2011. 8(5): p. 266-77.
37. Elliott, D. A., C. S. Weickert, and B. Garner, *Apolipoproteins in the brain: implications for neurological and psychiatric disorders*. Clin Lipidol, 2010. 51(4): p. 555-573.
38. Wang, F., et al., *Brd2 disruption in mice causes severe obesity without Type 2 diabetes*. Biochem J, 2010. 425(1): p. 71-83.
39. Denis, G. V., B. S. Nikolajczyk, and G. R. Schnitzler, *An emerging role for bromodomain-containing proteins in chromatin regulation and transcriptional control of adipogenesis*. FEBS Lett, 2010. 584(15): p. 3260-8.
40. Gagnon, D., et al., *Proteasomal degradation of the papillomavirus E2 protein is inhibited by overexpression of bromodomain-containing protein 4*. J Viral, 2009. 83(9): p. 4127-39.
41. You, J., et al., *Kaposi's sarcoma-associated herpesvirus latency-associated nuclear antigen interacts with bromodomain protein Brd4 on host mitotic chromosomes*. J Virol, 2006. 80(18): p. 8909-19.
42. Palermo, R. D., H. M. Webb, and M. J. West, *RNA polymerase II stalling promotes nucleosome occlusion and pTEFb recruitment to drive immortalization by Epstein-Barr virus*. PLoS Pathog, 2011. 7(10): p. e1002334.
43. Zhu, J., et al., *Reactivation of Latent HIV-1 by Inhibition of BRD4*. Cell Rep, 2012.
44. Banerjee, C., et al., *BET bromodomain inhibition as a novel strategy for reactivation of HIV-1*. J Leukoc Biol, 2012.
45. Bartholomeeusen, K., et al., *BET bromodomain inhibition activates transcription via a transient release of P-TEFb from 7SK snRNP*. J Biol Chem, 2012.
46. Li, Z., et al., *The BET bromodomain inhibitor JQ1 activates HIV latency through antagonizing Brd4 inhibition of Tat-transactivation*. Nucleic Acids Res, 2012.
47. Velisek, L., et al., *GABAergic neuron deficit as an idiopathic generalized epilepsy mechanism: the role of BRD2 haploinsufficiency in juvenile myoclonic epilepsy*. PLoS One, 2011. 6(8): p. e23656.
48. Gaucher, J., et al., *Bromodomain-dependent stage-specific male genome programming by Brdt*. EMBO J, 2012. 31(19): p. 3809-20.
49. Shang, E., et al., *The first bromodomain of Brdt, a testis-specific member of the BET sub-family of double-bromodomain-containing proteins, is essential for male germ cell differentiation*. Development, 2007. 134(19): p. 3507-15.
50. Matzuk, M. M., et al., *Small-Molecule Inhibition of BRDT for Male Contraception*. Cell, 2012. 150(4): p. 673-684.
51. Berkovits, B. D., et al., *The testis-specific double bromodomain-containing protein BRDT forms a complex with multiple spliceosome components and is required for mRNA splicing and 3'-UTR truncation in round spermatids*. Nucleic Acids Res, 2012. 40(15): p. 7162-75.
52. Niu, J. and P. E. Kolattukudy, *Role of MCP-1 in cardiovascular disease: molecular mechanisms and clinical implications*. Clin Sci (Lond), 2009. 117(3): p. 95-109.
53. Dawson, J., et al., *Targeting monocyte chemoattractant protein-1 signalling in disease*. Expert Opin Ther Targets, 2003. 7(1): p. 35-48.
54. Boring, L., et al., *Decreased lesion formation in CCR2−/− mice reveals a role for chemokines in the initiation of atherosclerosis*. Nature, 1998. 394(6696): p. 894-7.
55. Gosling, J., et al., *MCP-1 deficiency reduces susceptibility to atherosclerosis in mice that overexpress human apolipoprotein B*. J Clin Invest, 1999. 103(6): p. 773-8.
56. Gu, L., et al., *Absence of monocyte chemoattractant protein-1 reduces atherosclerosis in low density lipoprotein receptor-deficient mice*. Mol Cell, 1998. 2(2): p. 275-81.
57. Aiello, R. J., et al., *Monocyte chemoattractant protein-1 accelerates atherosclerosis in apolipoprotein E-deficient mice*. Arterioscler Thromb Vasc Biol, 1999. 19(6): p. 1518-25.

58. Nelken, N. A., et al., *Monocyte chemoattractant protein-1 in human atheromatous plaques*. J Clin Invest, 1991. 88(4): p. 1121-7.
59. Deo, R., et al., *Association among plasma levels of monocyte chemoattractant protein-1, traditional cardiovascular risk factors, and subclinical atherosclerosis*. J Am Coll Cardiol, 2004. 44(9): p. 1812-8.
60. de Lemos, J. A., et al., *Association between plasma levels of monocyte chemoattractant protein-1 and long-term clinical outcomes in patients with acute coronary syndromes*. Circulation, 2003. 107(5): p. 690-5.
61. Koch, A. E., et al., *Enhanced production of monocyte chemoattractant protein-1 in rheumatoid arthritis*. J Clin Invest, 1992. 90(3): p. 772-9.
62. Brodmerkel, C. M., et al., *Discovery and pharmacological characterization of a novel rodent-active CCR2 antagonist, INCB3344*. J Immunol, 2005. 175(8): p. 5370-8.
63. Bruhl, H., et al., *Dual role of CCR2 during initiation and progression of collagen-induced arthritis: evidence for regulatory activity of CCR2+ T cells*. J Immunol, 2004. 172(2): p. 890-8.
64. Gong, J. H., et al., *An antagonist of monocyte chemoattractant protein 1 (MCP-1) inhibits arthritis in the MRL-lpr mouse model*. J Exp Med, 1997. 186(1): p. 131-7.
65. Gong, J. H., et al., *Post-onset inhibition of murine arthritis using combined chemokine antagonist therapy*. Rheumatology (Oxford), 2004. 43(1): p. 39-42.
66. Mahad, D. J. and R. M. Ransohoff, *The role of MCP-1 (CCL2) and CCR2 in multiple sclerosis and experimental autoimmune encephalomyelitis (EAE)*. Semin Immunol, 2003. 15(1): p. 23-32.
67. Fife, B. T., et al., *CC chemokine receptor 2 is critical for induction of experimental autoimmune encephalomyelitis*. J Exp Med, 2000. 192(6): p. 899-905.
68. Huang, D. R., et al., *Absence of monocyte chemoattractant protein 1 in mice leads to decreased local macrophage recruitment and antigen-specific T helper cell type 1 immune response in experimental autoimmune encephalomyelitis*. J Exp Med, 2001. 193(6): p. 713-26.
69. Ishizu, T., et al., *CSF cytokine and chemokine profiles in acute disseminated encephalomyelitis*. J Neuroimmunol, 2006. 175(1-2): p. 52-8.
70. Gonzalez-Serrano, M. E., et al., *Increased Pro-inflammatory Cytokine Production After Lipopolysaccharide Stimulation in Patients with X-linked Agammaglobulinemia*. J Clin Immunol, 2012. 32(5): p. 967-74.
71. McKinley, L., et al., *TH17 cells mediate steroid-resistant airway inflammation and airway hyperresponsiveness in mice*. J Immunol, 2008. 181(6): p. 4089-97.
72. Taylan, A., et al., *Evaluation of the T helper 17 axis in ankylosing spondylitis*. Rheumatol Int, 2012. 32(8): p. 2511-5.
73. Ito, Y., et al., *Pathogenic significance of interleukin-6 in a patient with antiglomerular basement membrane antibody-induced glomerulonephritis with multinucleated giant cells*. Am J Kidney Dis, 1995. 26(1): p. 72-9.
74. Soltesz, P., et al., *Immunological features of primary anti-phospholipid syndrome in connection with endothelial dysfunction*. Rheumatology (Oxford), 2008. 47(11): p. 1628-34.
75. Gu, Y., et al., *Interleukin (IL)-17 promotes macrophages to produce IL-8, IL-6 and tumour necrosis factor-alpha in aplastic anaemia*. Br J Haematol, 2008. 142(1): p. 109-14.
76. Zhao, L., et al., *Interleukin-17 contributes to the pathogenesis of autoimmune hepatitis through inducing hepatic interleukin-6 expression*. PLoS One, 2011. 6(4): p. e18909.
77. Gloddek, B., K. Lamm, and W. Arnold, *Pharmacological influence on inner ear endothelial cells in relation to the pathogenesis of sensorineural hearing loss*. Adv Otorhinolaryngol, 2002. 59: p. 75-83.
78. Yamashita, T., et al., *IL-6-mediated Th17 differentiation through RORgammat is essential for the initiation of experimental autoimmune myocarditis*. Cardiovasc Res, 2011. 91(4): p. 640-8.
79. Ni, J., et al., *Involvement of Interleukin-17A in Pancreatic Damage in Rat Experimental Acute Necrotizing Pancreatitis*. Inflammation, 2012.
80. Hohki, S., et al., *Blockade of interleukin-6 signaling suppresses experimental autoimmune uveoretinitis by the inhibition of inflammatory Th17 responses*. Exp Eye Res, 2010. 91(2): p. 162-70.
81. Ma, D., et al., *Profile of Th17 cytokines (IL-17, TGF-beta, IL-6) and Th1 cytokine (IFN-gamma) in patients with immune thrombocytopenic purpura*. Ann Hematol, 2008. 87(11): p. 899-904.
82. Yoshimura, T., et al., *Involvement of Th17 cells and the effect of anti-IL-6 therapy in autoimmune uveitis*. Rheumatology (Oxford), 2009. 48(4): p. 347-54.
83. D'Auria, L., P. Cordiali Fei, and F. Ameglio, *Cytokines and bullous pemphigoid*. Eur Cytokine Netw, 1999. 10(2): p. 123-34.
84. El-Osta, H. E. and R. Kurzrock, *Castleman's disease: from basic mechanisms to molecular therapeutics*. Oncologist, 2011. 16(4): p. 497-511.
85. Lahdenpera, A. I., et al., *Up-regulation of small intestinal interleukin-17 immunity in untreated coeliac disease but not in potential coeliac disease or in type 1 diabetes*. Clin Exp Immunol, 2012. 167(2): p. 226-34.
86. Fujioka, A., et al., *The analysis of mRNA expression of cytokines from skin lesions in Churg-Strauss syndrome*. J Dermatol, 1998. 25(3): p. 171-7.
87. Holtta, V., et al., *IL-23/IL-17 immunity as a hallmark of Crohn's disease*. Inflamm Bowel Dis, 2008. 14(9): p. 1175-84.
88. Shibuya, M., et al., *Successful treatment with tocilizumab in a case of Cogan's syndrome complicated with aortitis*. Mod Rheumatol, 2012.
89. De Paiva, C. S., et al., *IL-17 disrupts corneal barrier following desiccating stress*. Mucosal Immunol, 2009. 2(3): p. 243-53.
90. Antonelli, A., et al., *Serum levels of proinflammatory cytokines interleukin-1 beta, interleukin-6, and tumor necrosis factor alpha in mixed cryoglobulinemia*. Arthritis Rheum, 2009. 60(12): p. 3841-7.
91. Chevrel, G., et al., *Interleukin-17 increases the effects of IL-1 beta on muscle cells: arguments for the role of T cells in the pathogenesis of myositis*. J Neuroimmunol, 2003. 137(1-2): p. 125-33.
92. Linhares, U. C., et al., *The Ex Vivo Production of IL-6 and IL-21 by CD4(+) T Cells is Directly Associated with Neurological Disability in Neuromyelitis Optica Patients*. J Clin Immunol, 2012.
93. Kyburz, D. and M. Corr, *Th17 cells generated in the absence of TGF-beta induce experimental allergic encephalitis upon adoptive transfer*. Expert Rev Clin Immunol, 2011. 7(3): p. 283-5.
94. Dias, P. M. and G. Banerjee, *The Role of Th17/IL-17 on Eosinophilic inflammation*. J Autoimmun, 2012.
95. Kahawita, I. P. and D. N. Lockwood, *Towards understanding the pathology of erythema nodosum leprosum*. Trans R Soc Trop Med Hyg, 2008. 102(4): p. 329-37.
96. Deng, J., et al., *Th17 and Th1 T-cell responses in giant cell arteritis*. Circulation, 2010. 121(7): p. 906-15.

97. Ooi, J. D., A. R. Kitching, and S. R. Holdsworth, *Review: T helper 17 cells: their role in glomerulonephritis*. Nephrology (Carlton), 2010. 15(5): p. 513-21.
98. Nakahama, H., et al., *Distinct responses of interleukin-6 and other laboratory parameters to treatment in a patient with Wegener's granulomatosis*. Intern Med, 1993. 32(2): p. 189-92.
99. Kim, S. E., et al., *Increased serum interleukin-17 in Graves' ophthalmopathy*. Graefes Arch Clin Exp Ophthalmol, 2012. 250(10): p. 1521-6.
100. Lu, M. O. and J. Zhu, *The role of cytokines in Guillain-Barre syndrome*. J Neurol, 2011. 258(4): p. 533-48.
101. Figueroa-Vega, N., et al., *Increased circulating pro-inflammatory cytokines and Th17 lymphocytes in Hashimoto's thyroiditis*. J Clin Endocrinol Metab, 2010. 95(2): p. 953-62.
102. Xu, L., et al., *Critical role of Th17 cells in development of autoimmune hemolytic anemia*. Exp Hematol, 2012.
103. Jen, H. Y., et al., *Increased serum interleukin-17 and peripheral Th17 cells in children with acute Henoch-Schonlein purpura*. Pediatr Allergy Immunol, 2011. 22(8): p. 862-8.
104. Lin, F. J., et al., *Imbalance of regulatory T cells to Th17 cells in IgA nephropathy*. Scand J Clin Lab Invest, 2012. 72(3): p. 221-9.
105. Baron, P., et al., *Production of IL-6 by human myoblasts stimulated with Abeta: relevance in the pathogenesis of IBM*. Neurology, 2001. 57(9): p. 1561-5.
106. Lamale, L. M., et al., *Interleukin-6, histamine, and methylhistamine as diagnostic markers for interstitial cystitis*. Urology, 2006. 68(4): p. 702-6.
107. Jia, S., et al., *The T helper type 17/regulatory T cell imbalance in patients with acute Kawasaki disease*. Clin Exp Immunol, 2010. 162(1): p. 131-7.
108. Min, C. K., et al., *Cutaneous leucoclastic vasculitis (LV) following bortezomib therapy in a myeloma patient; association with pro-inflammatory cytokines*. Eur J Haematol, 2006. 76(3): p. 265-8.
109. Rhodus, N. L., et al., *Proinflammatory cytokine levels in saliva before and after treatment of (erosive) oral lichen planus with dexamethasone*. Oral Dis, 2006. 12(2): p. 112-6.
110. Mok, M. Y., et al., *The relation of interleukin 17 (IL-17) and IL-23 to Th1/Th2 cytokines and disease activity in systemic lupus erythematosus*. J Rheumatol, 2010. 37(10): p. 2046-52.
111. Muller Kobold, A. C., et al., *In vitro up-regulation of E-selectin and induction of interleukin-6 in endothelial cells by autoantibodies in Wegener's granulomatosis and microscopic polyangiitis*. Clin Exp Rheumatol, 1999. 17(4): p. 433-40.
112. Jadidi-Niaragh, F. and A. Mirshafiey, *Th17 cell, the new player of neuroinflammatory process in multiple sclerosis*. Scand J Immunol, 2011. 74(1): p. 1-13.
113. Aricha, R., et al., *Blocking of IL-6 suppresses experimental autoimmune myasthenia gravis*. J Autoimmun, 2011. 36(2): p. 135-41.
114. Icoz, S., et al., *Enhanced IL-6 production in aquaporin-4 antibody positive neuromyelitis optica patients*. Int J Neurosci, 2010. 120(1): p. 71-5.
115. Lopez-Robles, E., et al., *TNFalpha and IL-6 are mediators in the blistering process of pemphigus*. Int J Dermatol, 2001. 40(3): p. 185-8.
116. Kallen, K. J., P. R. Galle, and S. Rose-John, *New developments in IL-6 dependent biology and therapy: where do we stand and what are the options?* Expert Opin Investig Drugs, 1999. 8(9): p. 1327-49.
117. Kawakami, T., S. Takeuchi, and Y. Soma, *Serum levels of interleukin-6 in patients with cutaneous polyarteritis nodosa*. Acta Derm Venereol, 2012. 92(3): p. 322-3.
118. Harada, K., et al., *Periductal interleukin-17 production in association with biliary innate immunity contributes to the pathogenesis of cholangiopathy in primary biliary cirrhosis*. Clin Exp Immunol, 2009. 157(2): p. 261-70.
119. Fujishima, S., et al., *Involvement of IL-17F via the induction of IL-6 in psoriasis*. Arch Dermatol Res, 2010. 302(7): p. 499-505.
120. Raychaudhuri, S. P., S. K. Raychaudhuri, and M. C. Genovese, *IL-17 receptor and its functional significance in psoriatic arthritis*. Mol Cell Biochem, 2012. 359(1-2): p. 419-29.
121. Kawakami, T., M. Yamazaki, and Y. Soma, *Reduction of interleukin-6, interleukin-8, and anti-phosphatidylserine-prothrombin complex antibody by granulocyte and monocyte adsorption apheresis in a patient with pyoderma gangrenosum and ulcerative colitis*. Am J Gastroenterol, 2009. 104(9): p. 2363-4.
122. Kawai, M., et al., *Sustained response to tocilizumab, anti-interleukin-6 receptor antibody, in two patients with refractory relapsing polychondritis*. Rheumatology (Oxford), 2009. 48(3): p. 318-9.
123. Ash, Z. and P. Emery, *The role of tocilizumab in the management of rheumatoid arthritis*. Expert Opin Biol Ther, 2012. 12(9): p. 1277-89.
124. Belli, F., et al., *Cytokines assay in peripheral blood and bronchoalveolar lavage in the diagnosis and staging of pulmonary granulomatous diseases*. Int J Immunopathol Pharmacol, 2000. 13(2): p. 61-67.
125. Radstake, T. R., et al., *The pronounced Th17 profile in systemic sclerosis (SSc) together with intracellular expression of TGFbeta and IFNgamma distinguishes SSc phenotypes*. PLoS One, 2009. 4(6): p. e5903.
126. Katsifis, G. E., et al., *Systemic and local interleukin-17 and linked cytokines associated with Sjogren's syndrome immunopathogenesis*. Am J Pathol, 2009. 175(3): p. 1167-77.
127. Sun, Y., et al., *MMP-9 and IL-6 are potential biomarkers for disease activity in Takayasu's arteritis*. Int J Cardiol, 2012. 156(2): p. 236-8.
128. Graber, J. J., et al., *Interleukin-17 in transverse myelitis and multiple sclerosis*. J Neuroimmunol, 2008. 196(1-2): p. 124-32.
129. Mudter, J. and M. F. Neurath, *Il-6 signaling in inflammatory bowel disease: pathophysiological role and clinical relevance*. Inflamm Bowel Dis, 2007. 13(8): p. 1016-23.
130. Haruta, H., et al., *Blockade of interleukin-6 signaling suppresses not only th17 but also interphotoreceptor retinoid binding protein-specific Th1 by promoting regulatory T cells in experimental autoimmune uveoretinitis*. Invest Ophthalmol Vis Sci, 2011. 52(6): p. 3264-71.
131. Bassiouny, D. A. and O. Shaker, *Role of interleukin-17 in the pathogenesis of vitiligo*. Clin Exp Dermatol, 2011. 36(3): p. 292-7. 115. Bradley, D. T. and S. E. Kountakis, *Role of interleukins and transforming growth factor-beta in chronic rhinosinusitis and nasal polyposis*. Laryngoscope, 2005. 115(4): p. 684-6.
132. Bradley, D. T. and S. E. Kountakis, *Role of interleukins and transforming growth factor-beta in chronic rhinosinusitis and nasal polyposis*. Laryngoscope, 2005. 115(4): p. 684-6.
133. Besnard, A. G., et al., *Inflammasome-IL-1-Th17 response in allergic lung inflammation*. J Mol Cell Biol, 2012. 4(1): p. 3-10.

134. Yoshii, T., et al., *Local levels of interleukin-1 beta, -4, -6 and tumor necrosis factor alpha in an experimental model of murine osteomyelitis due to staphylococcus aureus.* Cytokine, 2002. 19(2): p. 59-65.

135. Bayraktaroglu, T., et al., *Serum levels of tumor necrosis factor-alpha, interleukin-6 and interleukin-8 are not increased in dyspeptic patients with Helicobacter pylori-associated gastritis.* Mediators Inflamm, 2004. 13(1): p. 25-8.

136. Mitsuyama, K., et al., *STAT3 activation via interleukin 6 trans-signalling contributes to ileitis in SAMP1/Yit mice.* Gut, 2006. 55(9): p. 1263-9.

137. Johnson, R. B., N. Wood, and F. G. Serio, *Interleukin-11 and IL-17 and the pathogenesis of periodontal disease.* J Periodontol, 2004. 75(1): p. 37-43.

138. Latifi, S. Q., et al., *Persistent elevation of serum interleukin-6 in intraabdominal sepsis identifies those with prolonged length of stay.* J Pediatr Surg, 2004. 39(10): p. 1548-52.

139. Ortiz-Lucas, M., P. Saz-Peiro, and J. J. Sebastian-Domingo, *Irritable bowel syndrome immune hypothesis. Part two: the role of cytokines.* Rev Esp Enferm Dig, 2010. 102(12): p. 711-7.

140. Kappel, L. W., et al., *IL-17 contributes to CD4-mediated graft-versus-host disease.* Blood, 2009. 113(4): p. 945-52.

141. Traves, S. L. and L. E. Donnelly, *Th17 cells in airway diseases.* Curr Mol Med, 2008. 8(5): p. 416-26.

142. Chen, L., et al., *IL-17RA aptamer-mediated repression of IL-6 inhibits synovium inflammation in a murine model of osteoarthritis.* Osteoarthritis Cartilage, 2011. 19(6): p. 711-8.

143. Urano, W., et al., *The inflammatory process in the mechanism of decreased serum uric acid concentrations during acute gouty arthritis.* J Rheumatol, 2002. 29(9): p. 1950-3.

144. Simmons, E. M., et al., *Plasma cytokine levels predict mortality in patients with acute renal failure.* Kidney Int, 2004. 65(4): p. 1357-65.

145. Paquet, P. and G. E. Pierard, *Interleukin-6 and the skin.* Int Arch Allergy Immunol, 1996. 109(4): p. 308-17.

146. Kaplanski, G., et al., *Jarisch-Herxheimer reaction complicating the treatment of chronic Q fever endocarditis: elevated TNFalpha and IL-6 serum levels.* J Infect, 1998. 37(1): p. 83-4.

147. Scanlan, M. J., et al., *Expression of cancer-testis antigens in lung cancer: definition of bromodomain testis-specific gene (BRDT) as a new CT gene, CT9.* Cancer Lett, 2000. 150(2): p. 155-64.

148. Grunwald, C., et al., *Expression of multiple epigenetically regulated cancer/germline genes in nonsmall cell lung cancer.* Int J Cancer, 2006. 118(10): p. 2522-8.

149. Rodriguez, R. M., et al., *Aberrant epigenetic regulation of bromodomain BRD4 in human colon cancer.* J Mol Med (Berl), 2012. 90(5): p. 587-95.

150. Tong, W. G., et al., *Phase I and pharmacologic study of SNS-032, a potent and selective Cdk2, 7, and 9 inhibitor, in patients with advanced chronic lymphocytic leukemia and multiple myeloma.* J Clin Oncol, 2010. 28(18): p. 3015-22.

151. Bellan, C., et al., *CDK9/CYCLIN T1 expression during normal lymphoid differentiation and malignant transformation.* J Pathol, 2004. 203(4): p. 946-52.

152. De Falco, G., et al., *Cdk9 regulates neural differentiation and its expression correlates with the differentiation grade of neuroblastoma and PNET tumors.* Cancer Biol Ther, 2005. 4(3): p. 277-81.

153. Simone, C. and A. Giordano, *Abrogation of signal-dependent activation of the cdk9/cyclin T2a complex in human RD rhabdomyosarcoma cells.* Cell Death Differ, 2007. 14(1): p. 192-5.

154. Lee, D. K., H. O. Duan, and C. Chang, *Androgen receptor interacts with the positive elongation factor P-TEFb and enhances the efficiency of transcriptional elongation.* J Biol Chem, 2001. 276(13): p. 9978-84.

155. Kelly, P. N. and A. Strasser, *The role of Bcl-2 and its pro-survival relatives in tumourigenesis and cancer therapy.* Cell Death Differ, 2011. 18(9): p. 1414-24.

156. Costello, J. F., et al., *Cyclin-dependent kinase 6 (CDK6) amplification in human gliomas identified using two-dimensional separation of genomic DNA.* Cancer Res, 1997. 57(7): p. 1250-4.

157. Mendrzyk, F., et al., *Genomic and protein expression profiling identifies CDK6 as novel independent prognostic marker in medulloblastoma.* J Clin Oncol, 2005. 23(34): p. 8853-62.

158. Ramsay, R. G. and T. J. Gonda, *MYB function in normal and cancer cells.* Nat Rev Cancer, 2008. 8(7): p. 523-34.

159. Rudloff, U. and Y. Samuels, *TYRO3-mediated regulation of MITF: a novel target in melanoma?* Pigment Cell Melanoma Res, 2010. 23(1): p. 9-11.

160. Stenman, G., M. K. Andersson, and Y. Andren, *New tricks from an old oncogene: gene fusion and copy number alterations of MYB in human cancer.* Cell Cycle, 2010. 9(15): p. 2986-95.

161. Wang, G., et al., *Increased cyclin-dependent kinase 6 expression in bladder cancer.* Oncol Lett, 2012. 4(1): p. 43-46.

162. Uchida, T., et al., *Antitumor effect of bcl-2 antisense phosphorothioate oligodeoxynucleotides on human renal-cell carcinoma cells in vitro and in mice.* Mol Urol, 2001. 5(2): p. 71-8.

163. Alexandraki, K., et al., *Inflammatory process in type 2 diabetes: The role of cytokines.* Ann N Y Acad Sci, 2006. 1084: p. 89-117.

164. Poreba, E., J. K. Broniarczyk, and A. Gozdzicka-Jozefiak, *Epigenetic mechanisms in virus-induced tumorigenesis.* Clin Epigenetics, 2011. 2(2): p. 233-47.

165. Muller, S., P. Filippakopoulos, and S. Knapp, *Bromodomains as therapeutic targets.* Expert Rev Mol Med, 2011. 13: p. e29.

EXAMPLES

Example 1

2-(3-(4-Isopropylpiperazin-1-yl)phenyl)-5,7-dimethoxyquinazolin-4(3H)-one

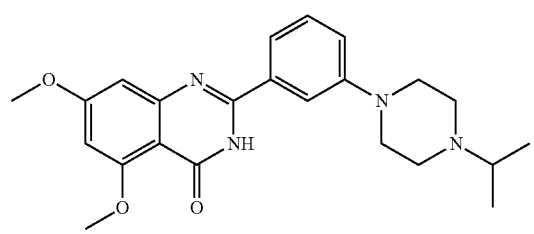 [SMILES: COc1cc(OC)c2c(=O)[nH]c(-c3cccc(N4CCN(C(C)C)CC4)c3)nc2c1]

To a solution of 2-amino-4,6-dimethoxy-benzamide (0.5 g, 2.55 mmol) in N,N-dimethylacetamide (30 mL) was added 3-bromo-benzaldehyde (0.32 mL, 2.80 mmol) followed by NaHSO₃ (0.39 g, 3.82 mmol) and p-toluenesulfonic acid monohydrate (0.24 g, 1.27 mmol). The reaction was heated at 120° C. for 20 h. After that time it was cooled to room temperature (rt), concentrated under reduced pressure and diluted with water. The precipitated solids were collected by filtration, washed with water and dried under vacuum. The product was triturated with diethyl ether to give 2-(3-bromo-phenyl)-5,7-dimethoxy-3H-quinazolin-4-one (0.81 g, 88%) as a yellow solid: ¹H NMR (400 MHz, CDCl₃) δ 8.23 (s, 1H), 7.84 (d, J=7.0 Hz, 1H), 7.66 (d, J=7.0 Hz, 1H), 7.38 (t, J=7.0 Hz, 1H), 6.8 (s, 1H), 6.46 (s, 1H), 3.94 (s, 3H), 3.90 (s, 3H).

A mixture of 2-(3-bromo-phenyl)-5,7-dimethoxy-3H-quinazolin-4-one (0.5 g, 1.38 mmol), 1-isopropyl-piperazine (0.24 mL, 1.66 mmol), potassium t-butoxide (0.32 g, 3.31 mmol), 2,2'-bis(diphenylphosphino)-1,1'-binaphthyl (60.1 mg, 0.096 mmol) and tris(dibenzylideneacetone)dipalladium (0) (31.6 mg, 0.034 mmol) in nitrogen saturated toluene (10 mL) was heated at 100° C. for 48 h. After that time the reaction was cooled to rt and concentrated under reduced pressure. The product was purified by flash column chromatography (silica gel, dichloromethane to 97:3 dichloromethane/methanol) to give 2-(3-(4-isopropylpiperazin-1-yl)phenyl)-5,7-dimethoxyquinazolin-4(3H)-one (0.080 g, 14%) as a yellow solid: mp 251-253° C.; ¹H NMR (400 MHz, CDCl₃): δ 7.56 (s, 1H), 7.42-7.38 (m, 2H), 7.13-7.09 (m, 1H), 6.84 (d, J=2.4 Hz, 1H), 6.46 (d, J=2.4 Hz, 1H), 3.98 (s, 3H), 3.94 (s, 3H), 3.38-3.28 (m, 4H), 2.78-2.68 (m, 4H), 1.11 (d, 6H); ESI MS m/z 407 (M−1)⁻

Example 2

2-(3-(4-Isopropylpiperazin-1-yl)-5-methoxyphenyl)-5,7-dimethoxyquinazolin-4(3H)-one

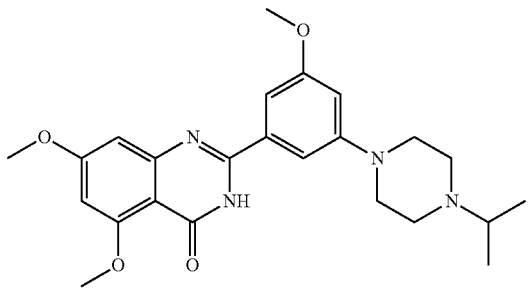 [SMILES: COc1cc(-c2nc3cc(OC)cc(OC)c3c(=O)[nH]2)cc(N2CCN(C(C)C)CC2)c1]

A solution of 1,3-dibromo-5-methoxybenzene (5.00 g, 18.8 mmol) in anhydrous diethyl ether (100 mL) was cooled to −78° C. Then a solution of n-butyllithium in hexanes (2.5 M, 8.3 mL, 20.68 mmol) was added drop-wise at −78° C. under nitrogen. After the addition was complete, the reaction was stirred at −78° C. for 45 min. After that time, anhydrous DMF (7.3 mL), 94.0 mmol) was added, the cooling bath was removed and the reaction mixture was allowed to warm to rt. The reaction was diluted with saturated aqueous NH₄Cl solution (100 mL) and diethyl ether (100 mL). The organic phase was separated, washed with water, dried over anhydrous Na₂SO₄ and concentrated under reduced pressure to give 3-bromo-5-methoxybenzaldehyde (3.95 g, 98%) as yellow oil: ¹H NMR (400 MHz, CDCl₃) δ 9.90 (s, 1H), 7.57-7.60 (m, 1H), 7.31-7.33 (m, 2H), 3.86 (s, 3H).

A solution of 3-bromo-5-methoxybenzaldehyde (3.93 g, 18.2 mmol), propane-1,3-diol (1.6 mL, 21.8 mmol) and p-toluenesulfonic acid monohydrate (0.104 g, 0.54 mmol) in anhydrous toluene (100 mL) was brought to reflux for 18 h under nitrogen. During this time water was removed using a Dean-Stark apparatus. After this time the reaction was cooled to rt, washed with 5% aqueous Na₂CO₃ solution (50 mL) and dried over anhydrous Na₂SO₄. The reaction was concentrated under reduced pressure to give 2-(3-bromo-5-methoxyphenyl)-1,3-dioxane (4.80 g, 96%) as a brown oil.

A mixture of 2-(3-bromo-5-methoxyphenyl)-1,3-dioxane (4.75 g, 17.4 mmol), 1-isopropyl-piperazine (3.14 mL, 21.96 mmol), sodium-tert-butoxide (3.00 g, 31.3 mmol), 2,2'-bis(diphenylphosphino)-1,1'-binaphthyl (0.342 g, 0.55 mmol) and tris(dibenzylideneacetone)dipalladium (0) (0.167 g, 0.18 mmol) in toluene (40 mL) was stirred at 100° C. for 18 h. After this time the reaction was cooled to rt and the dark brown mixture was poured into an ice-cold solution of 1N HCl (100 mL) and stirred vigorously for 2 h at rt. After this time the reaction mixture was re-cooled to 0° C. and the pH was adjusted to 13 with 6N NaOH solution. The reaction mixture was then extracted with diethyl ether. The organic phase was concentrated, taken up in 2N HCl (50 mL) and stirred for 1 h. The resulting mixture was extracted with dichloromethane (2×150 mL). The pH of the aqueous phase was adjusted to approximately 13 with 6N NaOH solution and extracted with diethyl ether (2×150 mL). The combined organic phase was washed with water, dried over anhydrous Na₂SO₄, and concentrated under reduced pressure to give 3-(4-isopropylpiperazin-1-yl)-5-methoxybenzaldehyde (1.24 g, 27%) as a viscous red oil: ¹H NMR (400 MHz, CDCl₃): δ 9.90 (s, 1H), 7.05 (dd, J=2.15, 1.37 Hz, 1H), 6.88 (dd, J=1.95, 1.17 Hz, 1H), 6.69 (t, J=2.34 Hz, 1H), 3.85 (s, 3H), 3.25-3.28 (m, 4H), 2.64-2.78 (m, 5H), 1.10 (d, J=6.64 Hz, 6H).

To a solution of 3-(4-isopropylpiperazin-1-yl)-5-methoxybenzaldehyde (1.23 g, 4.68 mmol) in N,N-dimethylacetamide (20 mL) was added 2-amino-4,6-dimethoxybenzamide (0.59 g, 3.00 mmol), NaHSO₃ (58.5 wt %, 0.87 g, 4.80 mmol) and p-toluenesulfonic acid monohydrate (1.82 g, 9.60 mmol). The reaction mixture was stirred at 120° C. for 20 h under nitrogen. After that time the reaction was cooled to rt and concentrated under reduced pressure. The residue was diluted with saturated Na₂CO₃ solution to adjust the pH to 12. The precipitated solids were collected by filtration, washed with water and dried under vacuum. The product was purified by flash column chromatography (silica gel, 86:10:4 dichloromethane/ethyl acetate/methanol followed by 86:10:4 dichloromethane/ethyl acetate/7 N NH₃ in methanol) and prep. HPLC to give 2-(3-(4-isopropylpiperazin-1-yl)-5-methoxyphenyl)-5,7-dimethoxyquinazolin-4(3H)-one (1.04 g, 50%) as a white solid: mp 212-213° C.; ¹H NMR (400 MHz, DMSO-d₆): δ 11.99 (s, 1H), 7.36 (s, 1H), 7.20 (s, 1H), 6.76 (d, J=2.34 Hz, 1H), 6.60 (t, J=1.95 Hz, 1H), 6.53 (d, J=1.95 Hz, 1H), 3.90 (s, 3H), 3.85 (s, 3H), 3.81 (s, 3H), 3.22 (t, J=4.29 Hz, 4H), 2.68 (quin, J=6.54 Hz, 1H), 2.58 (t, J=4.68 Hz, 4H), 1.01 (d, J=6.63 Hz, 6H); ESI MS m/z 437 [M−H]⁻.

Example 3

5,7-Dimethoxy-2-(6-(4-(2-methoxyethyl)piperazin-1yl)pyridin-2-yl)quinazolin-4(3H)-one

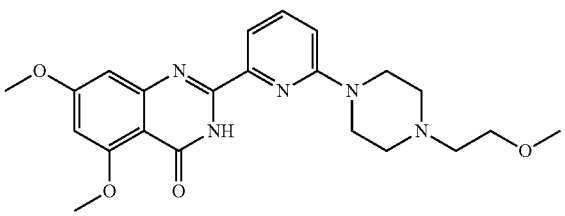

To a solution of 2-amino-4,6-dimethoxybenzamide (0.737 g, 3.76 mmol) and 6-fluoropicolinaldehyde (0.470 g, 3.76 mmol) in N,N-dimethylacetamide (20 mL), NaHSO$_3$ (58.5% SO$_2$ content, 1.0 g, 5.63 mmol) and p-toluenesulfonic acid monohydrate (0.143 g, 0.75 mmol) were added. The reaction was heated at 120° C. for 20 h. After that time the reaction was cooled to rt, concentrated under reduced pressure, diluted with water (50 mL) and saturated NaHCO$_3$ solution was added to adjust the pH to 8. The precipitated solids were collected by filtration, washed with water and dried. The product was purified by flash column chromatography (silica gel, 99:1 dichloromethane/methanol to 97:3 dichloromethane/methanol) to give 2-(6-fluoropyridin-2-yl)-5,7-dimethoxyquinazolin-4(3H)-one (0.550 g, 49%) as a yellow solid: $^1$H NMR (400 MHz, DMSO-d$_6$) δ 11.34 (s, 1H), 8.28-8.33 (m, 1H), 8.19-8.27 (m, 1H), 7.47 (dd, J=8.01, 1.76 Hz, 1H), 6.82 (d, J=2.34 Hz, 1H), 6.62 (d, J=2.34 Hz, 1H), 3.91 (s, 3H), 3.86 (s, 3H); $^{19}$F NMR (376 MHz, DMSO-d$_6$) δ −68.08 (d, J=8.03 Hz); ESI MS m/z 302 [M+H]$^+$.

A mixture of 2-(6-fluoropyridin-2-yl)-5,7-dimethoxyquinazolin-4(3H)-one (0.100 g, 0.33 mmol), 1-(2-methoxyethyl)piperazine (0.072 g, 0.49 mmol) and 1,1,3,3-tetramethylguanidine (0.096 g, 0.83 mmol) in dry DMSO (2 mL) was heated at 80° C. for 17 h. After that time the reaction mixture was cooled to rt and diluted with ethyl acetate (30 mL). The organic phase was washed with water and brine, dried over Na$_2$SO$_4$, filtered and concentrated under reduced pressure. The product was purified by flash column chromatography (silica gel, 97:3 dichloromethane/methanol to 95:5 dichloromethane/methanol) to give 5,7-dimethoxy-2-(6-(4-(2-methoxyethyl)piperazin-1-yl)pyridin-2-yl)quinazolin-4(3H)-one (0.070 g, 49%) as a yellow solid: mp 99-101° C.; $^1$H NMR (400 MHz, CDCl$_3$) δ 10.32 (s, 1H), 7.85 (d, J=7.42 Hz, 1H), 7.61-7.71 (m, 1H), 6.77-6.87 (m, 2H), 6.48 (d, J=1.95 Hz, 1H), 3.99 (s, 3H), 3.94 (s, 3H), 3.64-3.71 (m, 4H), 3.59 (t, J=5.47 Hz, 2H), 3.40 (s, 3H), 2.61-2.71 (m, 6H); ESI MS m/z 426 [M+H]$^+$.

Example 4

2-(6-(4-(2-Hydroxyethyl)piperazin-1-yl)pyridin-2-yl)-5,7-dimethoxyquinazolin-4(3H)-one

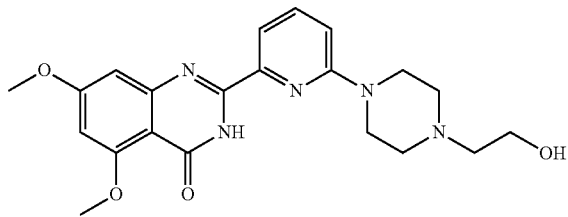 [SMILES: COc1cc(OC)c2c(=O)[nH]c(-c3cccc(N4CCN(CCO)CC4)n3)nc2c1]

To a solution of 2-amino-4,6-dimethoxybenzamide (0.40 g, 2.04 mmol) and 6-bromopyridine-2-carbaldehyde (0.379 g, 2.04 mmol) in N,N-dimethylacetamide (24 mL) was added NaHSO$_3$ (0.544 g, 3.06 mmol) and p-toluenesulfonic acid monohydrate (0.078 g, 0.408 mmol) at rt. The reaction mixture was heated at 120° C. for 6 h. After that time the reaction was cooled to rt, concentrated under reduced pressure and diluted with water (10 mL). The precipitated solids were collected by filtration, washed with water and dried. The product was purified by flash column chromatography (silica gel, 95:5 dichloromethane/methanol) to give 2-(6-bromopyridin-2-yl)-5,7-dimethoxyquinazolin-4(3H)-one (0.354 g, 48%) as a light yellow solid: $^1$H NMR (400 MHz, DMSO-d) δ 11.25 (br s, 1H), 8.36 (d, J=7.81 Hz, 1H), 7.87-8.04 (m, 2H), 6.81 (s, 1H), 6.62 (s, 1H), 3.91 (s, 3H), 3.87 (s, 3H); ESI MS m/z 362 [M+H]$^+$.

To a suspension of 2-(6-bromopyridin-2-yl)-5,7-dimethoxyquinazolin-4(3H)-one (0.193 g, 0.533 mmol) in dioxane (3 mL) was added palladium(II)acetate (0.012 g, 0.053 mmol), rac-2,2'-bis(diphenylphosphino)-1,1'-binaphthyl (0.0332 g, 0.053 mmol) and cesium carbonate (0.261 g, 0.800 mmol) under nitrogen. The reaction mixture was refluxed under nitrogen for 6.5 h. After that time the reaction was cooled to rt, filtered and concentrated under reduced pressure. The residue was purified by flash column chromatography (silica gel, 95:5 dichloromethane/methanol and trace amount of ammonium hydroxide) followed by trituration with diethyl ether to give 2-(6-(4-(2-hydroxyethyl)piperazin-1-yl)pyridin-2-yl)-5,7-dimethoxyquinazolin-4(3H)-one (0.043 g, 20%) as a light yellow solid: mp 175-177° C.; $^1$H NMR (400 MHz, DMSO-d) δ 11.05 (br s, 1H), 7.65-7.79 (m, 2H), 7.06 (d, J=8.20 Hz, 1H), 6.78 (s, 1H), 6.58 (s, 1H), 4.48 (br s, 1H), 3.91 (s, 3H), 3.86 (s, 3H), 3.64 (br s, 4H), 3.55 (br s, 2H), 2.54 (br s, 4H), 2.45 (t, 2H); ESI MS m/z 412 [M+H]$^+$.

Example 5

2-(6-(4-Isobutylpiperazin-1-yl)pyridin-2-yl)-5,7-dimethoxyquinazolin-4(3H)-one

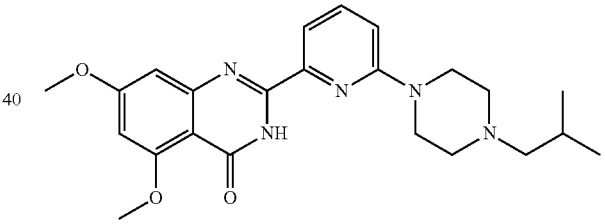

To a suspension of 2-(6-fluoropyridin-2-yl)-5,7-dimethoxyquinazolin-4(3H)-one (0.108 g, 0.36 mmol) in N,N-dimethylformamide (1.5 mL) was added K$_2$CO$_3$ (0.15 g, 1.07 mmol) and 1-isobutyl-piperazine (88.9 μL, 0.54 mmol). The resulting mixture was heated at 110° C. for 6 h. After that time N,N-dimethylacetamide (1.5 mL) was added and heating was continued for 20 h. After that time the reaction mixture was cooled to rt, diluted with ethyl acetate and filtered. The filtrate was concentrated under reduced pressure and the residue was washed with water, and dried under high vacuum. The product was purified by flash column chromatography (silica gel, 99:1 dichloromethane/methanol) to give 2-(6-(4-isobutylpiperazin-1-yl)pyridin-2-yl)-5,7-dimethoxyquinazolin-4(3H)-one (0.052 g, 34%) as a yellow solid: mp 188-189° C.; $^1$H NMR (400 MHz, CDCl$_3$) δ 10.33 (br s, 1H), 7.83 (d, J=7.42 Hz, 1H), 7.65 (dd, J=8.59, 7.42, 1H), 6.76-6.88 (m, 2H), 6.48 (d, J=2.34 Hz, 1H), 3.99 (s, 3H), 3.94 (s, 3H), 3.64 (t, J=4.88 Hz, 4H), 2.55 (t, J=4.88 Hz, 4H), 2.17 (d, J=7.42 Hz, 2H), 1.75-1.95 (m, 1H), 0.95 (d, J=6.64 Hz, 6H); ESI MS m/z 424 [M+H]$^+$.

Example 6

5,7-Dimethoxy-2-(6-(4-(2-(methylsulfonyl)ethyl) piperazin-1-yl)pyridin-2-yl)quinazazolin-4(3H)-one

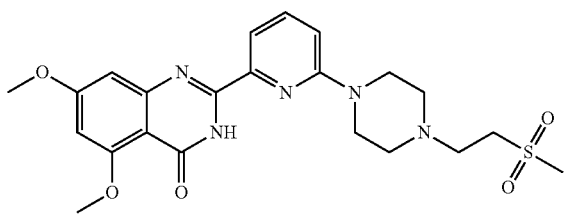

To a solution of 2-(6-fluoropyridin-2-yl)-5,7-dimethoxyquinazolin-4(3H)-one (0.200 g, 0.664 mmol) in DMSO (1.5 mL) under nitrogen was added 1-[2-(methylsulfonyl)ethyl] piperazine hydrochloride (0.265 g, 0.996 mmol) and 1,1,3,3-tetramethylguanidine. The reaction was stirred at 80° C. for 18 h. After that time the reaction was cooled to rt, diluted with ethyl acetate (50 mL), washed with water (2×20 mL), brine, dried over $Na_2SO_4$ and concentrated under reduced pressure. The product was purified by flash column chromatography (silica gel, 95:5 dichloromethane/methanol) to give 5,7-dimethoxy-2-(6-(4-(2-(methylsulfonyl)ethyl)piperazin-1-yl) pyridin-2-yl)quinazolin-4(3H)-one (0.120 g, 38%) as a yellow solid: mp 243-244° C.; $^1$H NMR (400 MHz, $CDCl_3$): δ 10.28 (br s, 1H), 7.88 (d, J=7.3 Hz, 1H), 7.73-7.66 (m, 1H), 6.87-6.81 (m, 2H), 6.49 (d, J=2.2 Hz, 1H), 3.99 (s, 3H), 3.94 (s, 3H), 3.69-3.61 (m, 4H), 3.23 (t, J=6.4 Hz, 2H), 3.09 (s, 3H), 2.98 (t, J=6.4 Hz, 2H), 2.72-2.64 (m, 4H).

Example 7

Methyl 2-(4-(6-(5,7-dimethoxy-4-oxo-3,4-dihydroquinazolin-2-yl)pyridin-2-yl)piperazin-1-yl)acetate

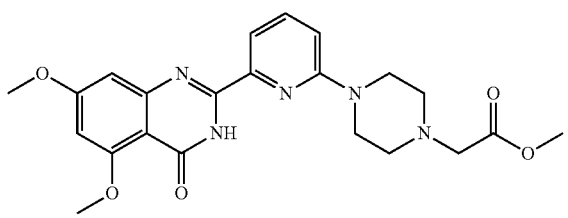

To a stirred suspension of methyl 2-(piperazin-1-yl)acetate dihydrochloride (0.67 g, 2.92 mmol) in dry DMSO (1.5 mL) was added 1,1,3,3-tetramethylguanidine (0.15 g, 1.07 mmol). The resulting mixture was stirred at rt for 10 min. Then 2-(6-fluoropyridin-2-yl)-5,7-dimethoxyquinazolin-4(3H)-one (0.40 g, 1.33 mmol) was added as a solid. The reaction was heated at 90° C. for 4.5 h. After that time the reaction was cooled to rt and diluted with ethyl acetate (30 mL). The organic phase was washed with water and brine, dried over sodium sulfate, filtered and concentrated under reduced pressure. The product was purified by flash column chromatography (silica gel, 98:2 dichloromethane/methanol) followed by trituration with diethyl ether to give methyl 2-(4-(6-(5,7-dimethoxy-4-oxo-3,4-dihydroquinazolin-2-yl)pyridin-2-yl) piperazin-1-yl)acetate (0.357 g, 61%) as a light yellow solid: mp 176-177° C.; $^1$H NMR (400 MHz, $CDCl_3$) δ 10.30 (br s, 1H), 7.86 (d, J=7.03 Hz, 1H), 7.63-7.71 (m, 1H), 6.80-6.86 (m, 2H), 6.48 (d, J=2.34 Hz, 1H), 3.99 (s, 3H), 3.94 (s, 3H), 3.77 (s, 3H), 3.67-3.73 (m, 4H), 3.34 (s, 2H), 2.73-2.79 (m, 4H); ESI MS m/z 440 [M+H]$^+$.

Example 8

2-(6-(4-(1-Hydroxypropan-2-yl)piperazin-1-yl)pyridin-2-yl)-5,7-dimethoxyquinazolin-4(3H)-one

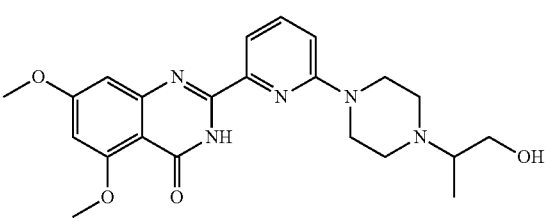 [SMILES: COc1cc(OC)c2c(=O)[nH]c(-c3cccc(N4CCN(C(C)CO)CC4)n3)nc2c1]

A mixture of 2-(6-fluoropyridin-2-yl)-5,7-dimethoxyquinazolin-4(3H)-one (0.202 g, 0.67 mmol), 2-(piperazin-1-yl)propan-1-ol dihydrochloride (0.292 g, 1.34 mmol) and 1,1,3,3-tetramethylguanidine (0.310 g, 2.69 mmol) in dry DMSO (1.5 mL) was heated at 85° C. for 6 h. After that time the reaction was cooled to rt, diluted with water (15 mL) and extracted with ethyl acetate (2×30 mL). The combined organic phase was washed with brine, dried over sodium sulfate, filtered and concentrated under reduced pressure. The product was purified by flash column chromatography (silica gel, 97:3 dichloromethane/methanol to 95:5 dichloromethane/methanol) to give 2-(6-(4-(1-hydroxypropan-2-yl)piperazin-1-yl)pyridin-2-yl)-5,7-dimethoxyquinazolin-4 (3H)-one (0.155 g, 54%) as a yellow solid: mp 202-204° C.; $^1$H NMR (400 MHz, $CDCl_3$) δ 10.30 (s, 1H), 7.87 (d, J=7.42 Hz, 1H), 7.64-7.72 (m, 1H), 6.79-6.88 (m, 2H) 6.49 (d, J=2.34 Hz, 1H) 3.99 (s, 3H), 3.94 (s, 3H), 3.61-3.72 (m, 4H), 3.38-3.52 (m, 2H), 2.89-2.99 (m, 1H), 2.78-2.88 (m, 2H), 2.54-2.64 (m, 2H), 0.97 (d, J=6.64 Hz, 3H); ESI MS m/z 426 [M+H]$^+$.

Example 9

2-(4-(6-(5,7-Dimethoxy-4-oxo-3,4-dihydroquinazolin-2-yl)pyridin-2-yl)piperazin-1-yl)propanamide

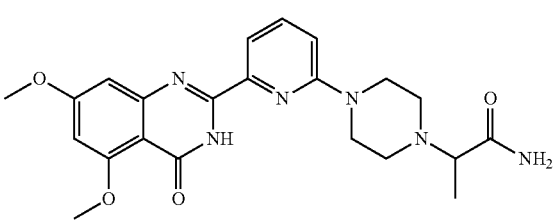 [SMILES: COc1cc(OC)c2c(=O)[nH]c(-c3cccc(N4CCN(C(C)C(N)=O)CC4)n3)nc2c1]

To a suspension of 2-(piperazin-1-yl)propanamide dihydrochloride (0.305 g, 1.33 mmol) in DMSO (1.5 mL), was added 1,1,3,3,-tetramethylguanidine (0.398 g, 3.45 mmol) at rt. The reaction mixture was stirred for 15 min. After that time 2-(6-fluoropyridin-2-yl)-5,7-dimethoxyquinazolin-4(3H)-one (0.20 g, 0.664 mmol) was added as a solid in a single portion. The resulting mixture was stirred at 90° C. for 3.5 h. After that time the reaction was cooled to rt and diluted with dichloromethane (50 mL). The organic phase was washed with brine, dried over $Na_2SO_4$ and concentrated under reduced pressure. The residue was purified by flash column chromatography (silica gel, 93:7 dichloromethane/methanol) to give 2-(4-(6-(5,7-dimethoxy-4-oxo-3,4-dihydroquinazolin-2-yl)pyridin-2-yl)piperazin-1-yl)propanamide (0.080 g, 28%) as a light yellow solid: mp 149-150° C.; $^1$H NMR (400 MHz, DMSO-$d_6$) δ 11.05 (br s, 1H), 7.65-7.79 (m, 2H), 7.30 (s, 1H), 7.06 (d, J=8.20 Hz, 1H), 6.78 (s, 1H), 6.58 (s, 1H), 4.48 (br s, 1H), 3.91 (s, 3H), 3.86 (s, 3H), 3.64 (br s, 4H), 3.55 (br s, 2H), 2.54 (br s, 4H), 2.45 (t, 2H); ESI MS m/z 439 [M+H]$^+$.

Example 10

2-(4-(6-(5,7-Dimethoxy-4-oxo-3,4-dihydroquinazolin-2-yl)pyridin-2-yl)piperazin-1-yl)acetic acid

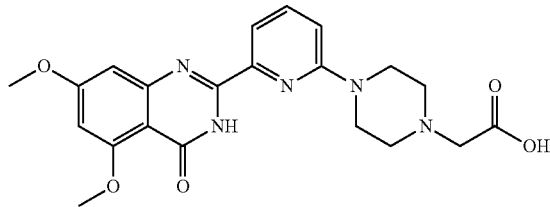 [SMILES: COc1cc(OC)c2c(=O)[nH]c(-c3cccc(N4CCN(CC(=O)O)CC4)n3)nc2c1]

To a solution of methyl 2-(4-(6-(5,7-dimethoxy-4-oxo-3,4-dihydroquinazolin-2-yl)pyridin-2-yl)piperazin-1-yl)acetate (0.156 g, 0.35 mmol) in THF (10 mL), water (5 mL) and methanol (3 mL) was added lithium hydroxide (0.043 g, 1.77 mmol). The reaction was stirred for 2 h at rt. After that time the reaction was cooled to rt, concentrated under reduced pressure, diluted with water (5 mL) and acidified with 1N HCl to pH 4.5-5.0. The precipitated solids were collected by filtration, washed with water and dried under high vacuum to give 2-(4-(6-(5,7-dimethoxy-4-oxo-3,4-dihydroquinazolin-2-yl)pyridin-2-yl)piperazin-1-yl)acetic acid (0.135 g, 91%) as a yellow solid: mp 225° C. dec.; $^1$H NMR (400 MHz, DMSO-$d_6$) δ 11.08 (s, 1H), 7.72-7.79 (m, 1H), 7.67-7.72 (m, 1H), 7.07 (d, J=8.59 Hz, 1H), 6.78 (d, J=1.56 Hz 1H), 6.58 (d, J=1.56 Hz, 1H) 3.91 (s, 3H), 3.86 (s, 3H), 3.63-3.74 (m, 4H), 3.23 (s, 2H), 2.65-2.74 (m, 4H); ESI MS m/z 426 [M+H]$^+$.

Example 11

3-(4-(6-(5,7-Dimethoxy-4-oxo-3,4-dihydroquinazolin-2-yl)pyridin-2-yl)piperazin-1-yl)propanoic acid

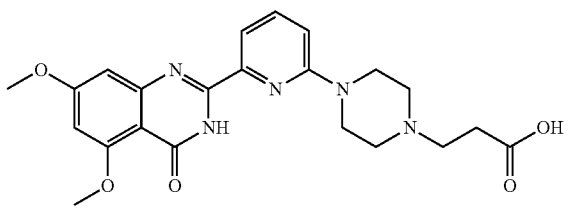 [SMILES: COc1cc(OC)c2c(=O)[nH]c(-c3cccc(N4CCN(CCC(=O)O)CC4)n3)nc2c1]

To a stirred suspension of methyl 3-(piperazin-1-yl)propanoate dihydrochloride (0.358 g, 1.46 mmol) and 2-(6-fluoropyridin-2-yl)-5,7-dimethoxyquinazolin-4(3H)-one (0.220 g, 0.73 mmol) in dry DMSO (1.5 mL) was added 1,1,3,3-tetramethylguanidine (0.336 g, 2.92 mmol). The resulting mixture was heated at 85° C. for 5 h. After that time the reaction was cooled to rt, diluted with water (20 mL) and extracted with ethyl acetate (3×25 mL). The organic phase was washed with water and brine, dried over sodium sulfate, filtered and concentrated under reduced pressure. The product was purified by flash column chromatography (silica gel, 99:1 dichloromethane/methanol to 97:3 dichloromethane/methanol) to give methyl 3-(4-(6-(5,7-dimethoxy-4-oxo-3,4-dihydroquinazolin-2-yl)pyridin-2-yl)piperazin-1-yl)propanoate (0.220 g, 66%) as an off-white solid: $^1$H NMR (400 MHz, CDCl$_3$) δ 10.31 (s, 1H), 7.85 (d, J=7.42 Hz, 1H), 7.62-7.70 (m, 1H), 6.79-6.85 (m, 2H), 6.48 (d, J=2.34 Hz, 1H), 3.99 (s, 3H), 3.94 (s, 3H), 3.72 (s, 3H), 3.59-3.67 (m, 4H), 2.75-2.83 (m, 2H), 2.54-2.66 (m, 6H); ESI MS m/z 454 [M+H]$^+$.

To a solution of methyl 3-(4-(6-(5,7-dimethoxy-4-oxo-3,4-dihydroquinazolin-2-yl)pyridin-2-yl)piperazin-1-yl)propanoate (0.200 g, 0.44 mmol) in THF (10 mL), water (5 mL) and methanol (3 mL) was added lithium hydroxide (0.053 g, 2.21 mmol). The reaction was stirred for 2 h at rt. After that time the reaction was concentrated under reduced pressure, diluted with water (5 mL) and acidified using 1N HCl to pH 4.5-5.0. The precipitated solids were collected by filtration, washed with water and dried under high vacuum to give 3-(4-(6-(5,7-dimethoxy-4-oxo-3,4-dihydroquinazolin-2-yl)pyridin-2-yl)piperazin-1-yl)propanoic acid (0.160 g, 83%) as a yellow solid: mp 241° C. dec.; $^1$H NMR (400 MHz, DMSO-$d_6$) δ 11.15 (s, 1H), 7.68-7.80 (m, 2H), 7.09 (d, J=8.20 Hz, 1H), 6.78 (d, J=1.95 Hz, 1H), 6.58 (d, J=1.95 Hz, 1H), 3.91 (s, 3H), 3.86 (s, 3H), 3.73 (br s, 4H), 2.77-2.85 (m, 2H), 2.73 (br s, 4H), 2.55 (t, J=7.22 Hz, 2H); ESI MS m/z 440 [M+H]$^+$.

Example 12

2-(5-(2-(Isopropylamino)ethoxy)-6-(4-isopropylpiperazin-1-yl)pyridin-2-yl)-5,7-dimethoxyquinazolin-4(3H)-one bis(trifluoroacetate)

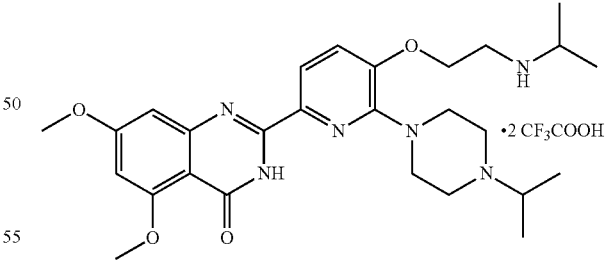

PBr$_3$ (0.160 mL, 1.70 mmol) was added dropwise to a solution of 2-(5-(2-hydroxyethoxy)-6-(4-isopropylpiperazin-1-yl)pyridin-2-yl)-5,7-dimethoxyquinazolin-4(3H)-one (0.40 g, 0.85 mmol) in N,N-dimethylformamide (10 mL) under nitrogen. The resulting mixture was heated at 60° C. for 2 h. After that time the reaction was cooled to rt and concentrated under reduced pressure and re-dissolved in chloroform (12 mL). Isopropylamine (4 mL) was added and the resulting mixture was heated at 50° C. in a sealed tube for 24 h. After that time the reaction was cooled to rt and concentrated under reduced pressure. The product was purified by flash column chromatography (silica gel, 90:10:0.8 dichloromethane/methanol/ammonium hydroxide) followed by preparative HPLC (0.1% trifluoroacetic acid in acetonitrile/water) to give 2-(5-(2-(isopropylamino)ethoxy)-6-(4-isopropylpiperazin-1-yl)pyridin-2-yl)-5,7-dimethoxyquinazolin-4(3H)-one bis (trifluoroacetate) (0.056 g, 9%) as a yellow solid: mp 186-188° C.; $^1$H NMR (400 MHz, DMSO-$d_6$) δ 11.07 (br s, 1H), 9.56 (br s, 1H), 8.74 (br s, 2H), 8.01 (d, J=8.8 Hz, 1H), 7.59 (d, J=8.4 Hz, 1H), 6.75 (d, J=2.4 Hz, 1H), 6.57 (d, J=2.4 Hz, 2H), 4.48 (d, J=11.6 Hz, 2H), 4.37 (dd, J=4.4, 5.2 Hz, 2H), 3.91 (s, 3H), 3.86 (s, 3H), 360-3.40 (m, 5H), 3.23-3.10 (m, 4H), 1.31 (d, J=6.8 Hz, 6H), 1.28 (d, J=6.4 Hz, 6H); $^{19}$F NMR (376 MHz, DMSO-$d_6$) δ ppm −73.80; ESI MS m/z 511 [M+H]$^+$.

Example 13

2-(5-(2-Hydroxyethoxy)-6-(4-isopropylpiperazin-1-yl)pyridin-2-yl)-5,7-dimethoxyquinazolin-4(3H)-one acetate

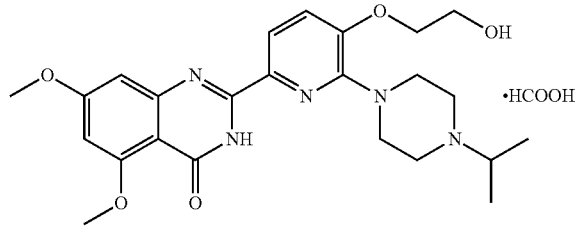 [SMILES: COc1cc(OC)c2c(=O)[nH]c(-c3ccc(OCCO)c(N4CCN(C(C)C)CC4)n3)nc2c1 ; "·HCOOH"]

To a mixture of (6-bromo-5-(2-((tert-butyldimethylsilyl)oxy)ethoxy)pyridin-2-yl)methanol (2.18 g, 6.0 mmol), 1-isopropylpiperazine (0.92 g, 7.2 mmol), BINAP (0.37 g, 0.6 mmol), and Cs$_2$CO$_3$ (3.18 g, 9.0 mmol) in nitrogen saturated toluene (40 mL) was added palladium(II) acetate (0.13 g, 0.6 mmol). The resulting mixture was heated at 100° C. for 18 h. After that time the reaction was cooled to rt, diluted with brine and extracted with ethyl acetate. The organic phase was dried over Na$_2$SO$_4$ and concentrated under reduced pressure. The product was purified by flash column chromatography (silica gel, 95:5 dichloromethane/methanol to 90:10 dichloromethane/methanol) to give (5-(2-((tert-butyldimethylsilyl)oxy)ethoxy)-6-(4-isopropylpiperazin-1-yl)pyridin-2-yl) methanol (1.07 g, 44%) as a sticky yellow solid: $^1$H NMR (400 MHz, CDCl$_3$): δ 7.05 (d, J=7.6 Hz, 1H), 6.66 (d, J=8.0 Hz, 1H), 4.59 (s, 2H), 4.06-3.97 (m, 4H), 3.53 (br s, 4H), 2.68 (m, 5H), 1.10 (d, J=6.4 Hz, 6H), 0.90 (s, 9H), 0.09 (s, 6H).

To a solution of (5-(2-((tert-butyldimethylsilyl)oxy)ethoxy)-6-(4-isopropylpiperazin-1-yl)pyridin-2-yl)methanol (1.07 g, 2.61 mmol) in 1,2-dichloroethane (20 mL) under nitrogen was added 2-iodoxybenzoic acid (0.88 g, 3.14 mmol) at rt. The reaction mixture was stirred at 80° C. for 1.5 h. After that time the reaction was cooled to rt and concentrated under reduced pressure. The product was purified by flash column chromatography (silica gel, 95:5 dichloromethane/methanol) to give 5-(2-((tert-butyldimethylsilyl)oxy)ethoxy)-6-(4-isopropylpiperazin-1-yl)picolinaldehyde (0.63 g, 59%) as a brown solid: $^1$H NMR (400 MHz, CDCl$_3$): δ 9.85 (s, 1H), 7.59 (d, J=8.4 Hz, 1H), 7.17 (d, J=8.0 Hz, 1H), 4.19-4.15 (m, 2H), 4.02-3.88 (m, 6H), 3.56-3.48 (m, 1H), 3.20 (br s, 4H), 1.37 (d, J=6.4 Hz, 6H), 0.90 (s, 9H), 0.09 (s, 6H); ESI MS m/z 408 [M+H]$^+$.

To a solution of 2-amino-4,6-dimethoxy-benzamide (0.302 g, 1.54 mmol) in N,N-dimethylacetamide (10 mL) was added 5-[2-(tert-butyl-dimethyl-silanyloxy)-ethoxy]-6-(4-methanesulfonyl-2-trifluoromethyl-phenyl)-pyridine-2-carbaldehyde (0.630 g, 1.54 mmol) followed by NaHSO$_3$ (0.321 g, 3.08 mmol) and p-toluenesulfonic acid monohydrate (0.293 g, 1.54 mmol). The resulting mixture was heated at 120° C. for 20 h. After that time the reaction was cooled to rt, concentrated under reduced pressure and diluted with water. Saturated Na$_2$CO$_3$ was added to adjust the pH to 9-10. The precipitated solids were collected by filtration, washed with water and dried under vacuum. The product was purified by flash column chromatography (silica gel, 90:10:1 dichloromethane/methanol/ammonium hydroxide) to give 2-(5-(2-hydroxyethoxy)-6-(4-isopropylpiperazin-1-yl)pyridin-2-yl)-5,7-dimethoxyquinazolin-4(3H)-one (0.47 g, 65%) as a sticky yellow solid: $^1$H NMR (400 MHz, CDCl$_3$): δ 10.22 (br s, 1H), 8.07 (d, J=8.0 Hz, 1H), 7.23 (d, J=8.4 Hz, 1H), 6.78 (d, J=2.4 Hz, 1H), 6.45 (d, J=2.4 Hz, 1H), 4.21 (dd, J=4.0, 4.4 Hz, 2H), 3.98 (s, 3H), 3.93 (s, 3H), 3.55-3.53 (m, 5H), 2.76-2.72 (m, 6H), 1.11 (d, J=6.8 Hz, 6H); ESI MS m/z 470 [M+H]$^+$.

A sample of 2-(5-(2-hydroxyethoxy)-6-(4-isopropylpiperazin-1-yl)pyridin-2-yl)-5,7-dimethoxyquinazolin-4(3H)-one (0.050 g,) was further purified by preparative HPLC (0.1% formic acid in acetonitrile/water) to give 2-(5-(2-hydroxyethoxy)-6-(4-isopropylpiperazin-1-yl)pyridin-2-yl)-5,7-dimethoxyquinazolin-4(3H)-one formate (0.026 g, 52%) as a yellow solid: mp 138-139° C.; $^1$H NMR (400 MHz, DMSO-$d_6$): δ 10.62 (br s, 1H), 8.29 (s, 1H), 7.89 (d, J=8.4 Hz, 1H), 7.43 (d, J=8.8 Hz, 1H), 6.75 (d, J=2.4 Hz, 1H), 6.54 (d, J=2.4 Hz, 1H), 4.12 (t, J=4.8 Hz, 2H), 3.90 (s, 3H), 3.85 (s, 3H), 3.78 (t, J=4.8 Hz, 2H), 3.56-3.30 (m, 8H), 2.72-2.66 (m, 1H), 2.62-2.58 (m, 2H), 1.02 (d, J=6.8 Hz, 6H); ESI MS m/z 470 [M+H]$^+$.

Example 14

2-(6-(4-Isopropylpiperazin-1-yl)-5-methoxypyridin-2-yl)-5,7-dimethoxyquinazolin-4(3H)-one

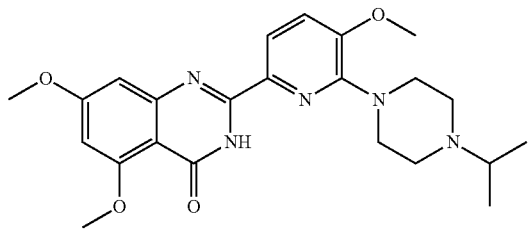 [SMILES: COc1cc(OC)c2c(=O)[nH]c(-c3ccc(OC)c(N4CCN(C(C)C)CC4)n3)nc2c1]

To a solution of 2-bromo-6-(hydroxymethyl)pyridin-3-ol (2.04 g, 10 mmol) and K$_2$CO$_3$ (2.07 g, 15 mmol) in acetone (50 mL) was added iodomethane (1.84 g, 13 mmol) at rt. The reaction mixture was refluxed for 4 h. After that time the reaction was cooled to rt, filtered to remove solids and concentrated under reduced pressure to give (6-bromo-5-methoxypyridin-2-yl)methanol (3.42 g, >99%) as a white solid: $^1$H NMR (400 MHz, CDCl$_3$): δ 7.25 (d, J=8.0 Hz, 1H), 7.16 (d, J=8.4 Hz, 1H), 4.70 (s, 2H), 3.93 (s, 3H), 2.78 (br s, 1H).

To a solution of (6-bromo-5-methoxypyridin-2-yl)methanol (2.30 g, 10 mmol) in dichloromethane (50 mL) was added MnO$_2$ (8.0 g) at rt. The reaction mixture was stirred at rt for 24 h. After that time the reaction was cooled to rt, filtered to remove solids and concentrated under reduced pressure to give 6-bromo-5-methoxypicolinaldehyde (1.35 g, 63%) as an off-white solid: $^1$H NMR (400 MHz, CDCl$_3$): δ 9.94 (s, 1H), 7.96 (d, J=8.4 Hz, 1H), 7.27 (d, J=8.0 Hz, 1H), 4.03 (s, 3H).

To a solution of 2-amino-4,6-dimethoxy-benzamide (1.23 g, 6.25 mmol) in N,N-dimethylacetamide (100 mL) was added 6-bromo-5-methoxypicolinaldehyde (1.35 g, 1.2 mmol) followed by NaHSO$_3$ (0.98 g, 9.38 mmol) and p-toluenesulfonic acid monohydrate (1.19 g, 6.25 mmol). The resulting mixture was heated at 120° C. for 20 h. After that time the reaction was cooled to it, concentrated under reduced pressure and diluted with saturated Na$_2$CO$_3$. The precipitated solids were collected by filtration, washed with water and dried under vacuum. The product was purified by flash column chromatography (silica gel, 99:1 dichloromethane/methanol) followed by trituration with ethyl acetate to give 2-(6-bromo-5-methoxypyridin-2-yl)-5,7-dimethoxyquinazolin-4(3H)-one (1.27 g, 52%) as a white solid: $^1$H NMR (400 MHz, DMSO-d$_6$): δ 11.03 (br s, 1H), 8.32 (d, J=8.4 Hz, 1H), 7.72 (d, J=8.8 Hz, 1H), 6.76 (d, J=2.0 Hz, 1H), 6.56 (d, J=2.4 Hz, 1H), 4.00 (s, 3H), 3.90 (s, 3H), 3.85 (s, 3H).

To a mixture of 2-(6-bromo-5-methoxypyridin-2-yl)-5,7-dimethoxyquinazolin-4(3H)-one (0.196 g, 0.50 mmol), 1-isopropylpiperazine (0.077 g, 0.60 mmol), BINAP (0.062 g, 0.10 mmol), and Cs$_2$CO$_3$ (0.652 g, 2.0 mmol) in nitrogen saturated dioxane (10 mL) was added palladium(II) acetate (0.022 g, 0.10 mmol). The resulting mixture was heated at 100° C. for 3 h. After that time the reaction was cooled to rt, diluted with dichloromethane (100 mL) and washed with water (20 mL). The organic phase was dried over Na$_2$SO$_4$ and concentrated under reduced pressure. The product was purified by flash column chromatography (silica gel, 90:10:0.1 dichloromethane/methanol/ammonium hydroxide) to give 2-(6-(4-isopropylpiperazin-1-yl)-5-methoxypyridin-2-yl)-5,7-dimethoxyquinazolin-4(3H)-one (0.055 g, 25%) as a pale yellow solid: mp 208-210° C.; $^1$H NMR (400 MHz, CDCl$_3$): δ 10.23 (br s, 1H), 8.08 (d, J=8.0 Hz, 1H), 7.17 (d, J=8.0 Hz, 1H), 6.79 (d, J=2.4 Hz, 1H), 6.45 (d, J=2.4 Hz, 1H), 3.98 (s, 3H), 3.95 (s, 3H), 3.93 (s, 3H), 3.56 (br s, 4H), 2.78 (br s, 5H), 1.15 (d, J=5.6 Hz, 6H); ESI MS m/z 440 [M+H]$^+$.

Example 15

5,7-Dimethoxy-2-(6-(4-methylpiperazin-1-yl)pyridin-2-yl)quinazolin-4(3H)-one Hydrochloride

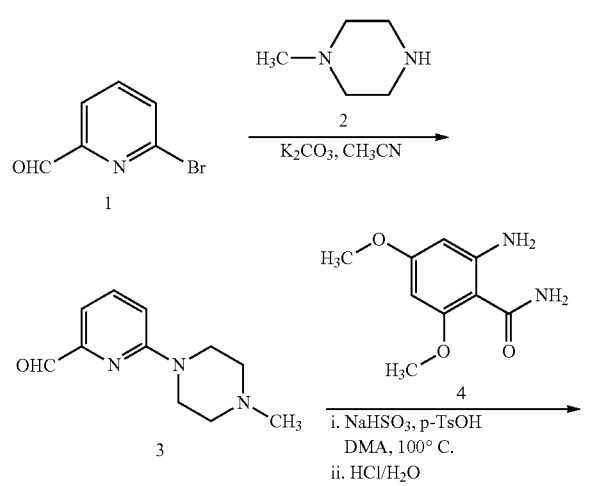

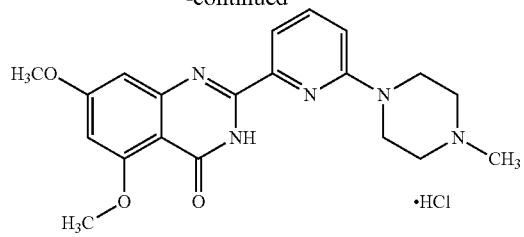

Example 15

Preparation of 6-(4-Methylpiperazin-1-yl)picolinaldehyde (3). A suspension of 6-bromopicolinaldehyde (1.50 g, 8.10 mmol), 1-methylpiperazine (2, 4.04 g, 40.0 mmol), potassium carbonate (4.46 g, 32.0 mmol) and anhydrous CH$_3$CN (10 mL) was placed in a sealed vessel and the mixture was heated at 110° C. for 17 h. The mixture was diluted with water (50 mL) and brought to pH 7 using 2 N aq. HCl (15 mL). The resulting solution was extracted with CH$_2$Cl$_2$ (3×50 mL) and the combined extracts were washed with brine (200 mL). The solution was dried (Na$_2$SO$_4$), filtered, concentrated and purified by silica gel chromatography eluting with 0-5% CH$_3$OH in CH$_2$Cl$_2$ to afford the title compound (0.528 g, 32%) as an orange oil: $^1$H NMR (500 MHz, CDCl$_3$) δ 9.84 (s, 1H), 7.62 (t, J=8.0 Hz, 1H), 7.27 (d, J=7.0 Hz, 1H), 6.85 (d, J=7.0 Hz, 1H), 3.67-3.65 (m, 4H), 2.55-2.52 (m, 4H), 2.36 (s, 3H).

Preparation of 5,7-Dimethoxy-2-(6-(4-methylpiperazin-1-yl)pyridin-2-yl)quinazolin-4(3H)-one Hydrochloride (Example 15). 2-Amino-4,6-dimethoxybenzamide (4, 200 mg, 1.02 mmol), 6-(4-methylpiperazin-1-yl)picolinaldehyde (3, 231 mg, 1.12 mmol), para-toluenesulfonic acid (466 mg, 2.45 mmol), sodium hydrogen sulfite (297 mg, 2.85 mmol) and anhydrous N,N-dimethylacetamide (12 mL) were mixed in a sealed tube and heated at 110° C. for 17 h. The solvent was removed in vacuo, the residue was dissolved in methanol (20 mL) and DCM:CH$_3$OH:aq. NH$_4$OH (80:18:2, 20 mL) and the contents were adsorbed onto silica gel (5 g). The adsorbed material was purified by silica gel chromatography eluting with 0-50% DCM:CH$_3$OH:aq. NH$_4$OH (80:18:2) in CH$_2$Cl$_2$ then using preparative HPLC. After concentration, 5 N aq. HCl (3 mL) was added and the suspension was concentrated in vacuo and placed in a drying oven at 50° C. for 17 h to afford the title compound (0.127 g, 25%) as an off-white solid: $^1$H NMR (500 MHz, CD$_3$OD) δ 7.97-7.95 (m, 1H), 7.82 (d, J=7.5 Hz, 1H), 7.39 (d, J=8.5 Hz, 1H), 7.20 (d, J=2.0 Hz, 1H), 6.79 (d, J=2.0 Hz, 1H), 4.82 (d, J=14.5 Hz, 2H), 4.00 (s, 3H), 3.99 (s, 3H), 3.67 (d, J=12.5 Hz, 2H), 3.48-3.42 (m, 2H), 3.31-3.24 (m, 2H), 3.00 (s, 3H); ESI MS m/z 382 [M+H]$^+$.

Example 16

Preparation of 5,7-Dimethoxy-2-(6-morpholinopyridin-2-yl)quinazolin-4(3H)-one Hydrochloride

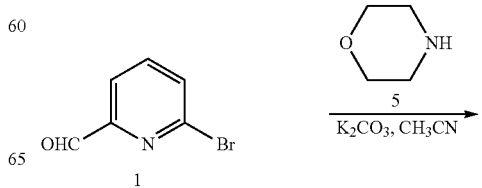

-continued

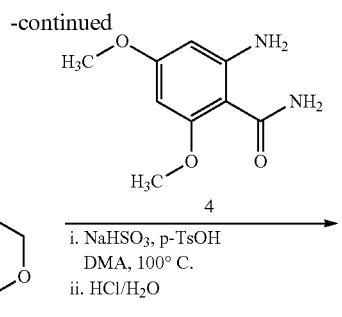

Example 16

Preparation of 6-Morpholinopicolinaldehyde (6): Following the method described for 3 above (see Example 15), compound 6 was made from morpholine (5) in 34% yield: $^1$H NMR (500 MHz, CDCl$_3$) δ 9.89 (s, 1H), 7.67-7.65 (m, 1H), 7.31 (d, J=7.0 Hz, 1H), 6.84 (d, J=8.5 Hz, 1H), 3.86-3.84 (m, 4H), 3.62-3.60 (m, 4H).

Preparation of 5,7-Dimethoxy-2-(6-morpholinopyridin-2-yl)quinazolin-4(3H)-one Hydrochloride (Example 16): Following the method described for Example 15 above, Example 16 was made from 6-morpholinopicolinaldehyde (6) in 21% yield: $^1$H NMR (500 MHz, DMSO-d$_6$) δ 11.0 (br s, 1H), 7.77 (t, J=7.5 Hz, 1H), 7.72 (d, J=7.0 Hz, 1H), 7.06 (d, J=8.5 Hz, 1H), 6.77 (d, J=2.0 Hz, 1H), 6.57 (d, J=2.0 Hz, 1H), 3.90 (s, 3H), 3.86 (s, 3H), 3.75-3.73 (m, 4H), 3.63-3.61 (m, 4H); ESI MS m/z 369 [M+H]$^+$.

Example 17

Preparation of 2-(6-(4-Isopropylpiperazin-1-yl)pyridin-2-yl)-5,7-dimethoxyquinazolin-4(3H)-one Hydrochloride -continued

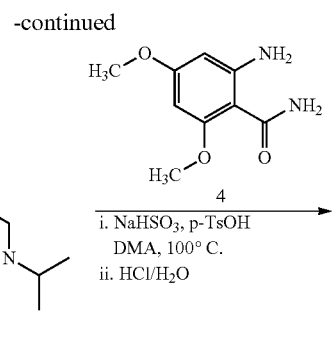

Example 17

Preparation of 6-(4-isopropylpiperazin-1-yl)picolinaldehyde (8): Following the method described for 3 above (see Example 15), compound 8 was made from 1-isopropylpiperazine (7) in 22% yield: $^1$H NMR (500 MHz, CDCl$_3$) δ 9.89 (s, 1H), 7.60 (t, J=7.5 Hz, 1H), 7.27 (d, J=7.0 Hz, 1H), 6.84 (d, J=8.5 Hz, 1H), 3.66-3.64 (m, 4H), 2.74 (sept, 1H), 2.66-2.64 (m, 4H).

Preparation of 2-(6-(4-Isopropylpiperazin-1-yl)pyridin-2-yl)-5,7-dimethoxyquinazolin-4(3H)-one Hydrochloride (Example 17): Following the method described for Example 15 above, compound Example 17 was made from 6-(4-isopropylpiperazin-1-yl)picolinaldehyde (8) in 23% yield: $^1$H NMR (500 MHz, DMSO-d$_6$) δ 10.7 (br s, 1H), 7.83 (t, J=7.5 Hz, 1H), 7.78 (d, J=7.5 Hz, 1H), 7.17 (d, J=8.0 Hz, 1H), 6.79 (d, J=2.0 Hz, 1H), 6.59 (d, J=2.0 Hz, 1H), 4.76-4.72 (m, 2H), 3.90 (s, 3H), 3.87 (s, 3H), 3.53-3.51 (m, 3H), 3.41-3.36 (m, 2H), 3.10-3.06 (m, 2H), 1.33 (d, J=7.0 Hz, 6H); ESI MS m/z 410 [M+H]$^+$.

Example 18

Preparation of 5,7-Dimethoxy-2-(6-(4-(methylsulfonyl)piperazin-1-yl)pyridin-2-yl)quinazolin-4(3H)-one Hydrochloride

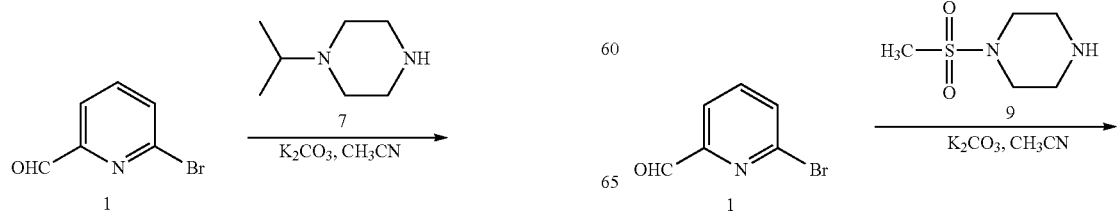

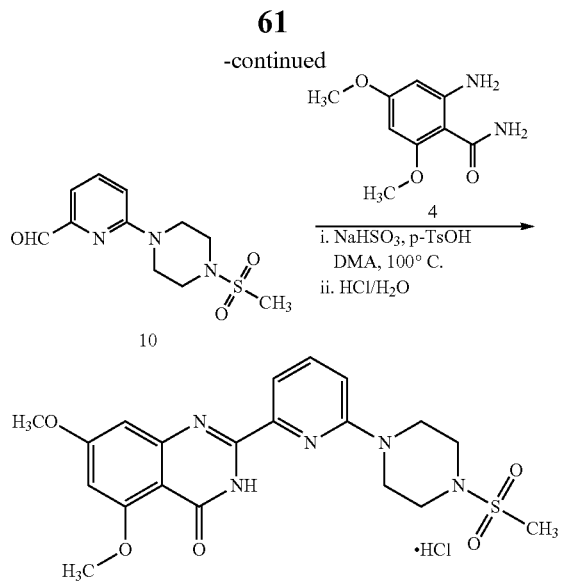

Example 18

Preparation of 6-(4-(Methylsulfonyl)piperazin-1-yl)picolinaldehyde (10): A suspension of 6-bromopicolinaldehyde (1.50 g, 8.10 mmol), 1-(methylsulfonyl)piperazine (9, 5.30 g, 32.2 mmol), potassium carbonate (4.45 g, 32.2 mmol) and anhydrous DMF (10 mL) was placed in a sealed vessel and the mixture was heated at 120° C. for 20 h. The mixture was diluted with water (50 mL) and brought to pH 7 using 2 N aq. HCl (15 mL). The resulting solution was extracted with $CH_2Cl_2$ (3×50 mL) and the combined extracts were washed with brine (200 mL). The solution was dried ($MgSO_4$), filtered, concentrated, and purified by silica gel chromatography eluting with 0-3% $CH_3OH$ in $CH_2Cl_2$ to afford the title compound (0.441 g, 20%) as an orange oil: $^1$H NMR (500 MHz, $CDCl_3$) δ 9.90 (s, 1H), 7.67 (t, J=8.0 Hz, 1H), 7.34 (d, J=7.0 Hz, 1H), 6.89 (d, J=8.5 Hz, 1H), 3.80-3.78 (m, 4H), 3.37-3.33 (m, 4H), 2.81 (s, 3H).

Preparation of 5,7-Dimethoxy-2-(6-(4-(methylsulfonyl)piperazin-1-yl)pyridin-2-yl)quinazolin-4(3H)-one Hydrochloride (Example 18): Following the method described for Example 15 above, Example 18 was made from 6-(4-(methylsulfonyl)piperazin-1-yl)picolinaldehyde (10) in 11% yield: $^1$H NMR (500 MHz, DMSO-$d_6$) δ 7.81-7.78 (m, 1H), 7.75-7.54 (m, 1H), 7.14 (d, J=8.0 Hz, 1H), 6.83 (d, J=2.0 Hz, 1H), 6.59 (d, J=2.0 Hz, 1H), 3.91 (s, 3H), 3.87 (s, 3H), 3.83-3.81 (m, 4H), 3.24-3.22 (m, 4H), 2.92 (s, 3H); ESI MS m/z 446 [M+H]$^+$.

Example 19

Preparation of 5,7-Dimethoxy-2-(6-(4-propionylpiperazin-1-yl)pyridin-2-yl)quinazolin-4(3H)-one dihydrochloride

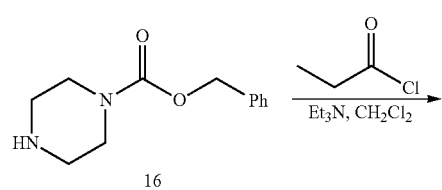

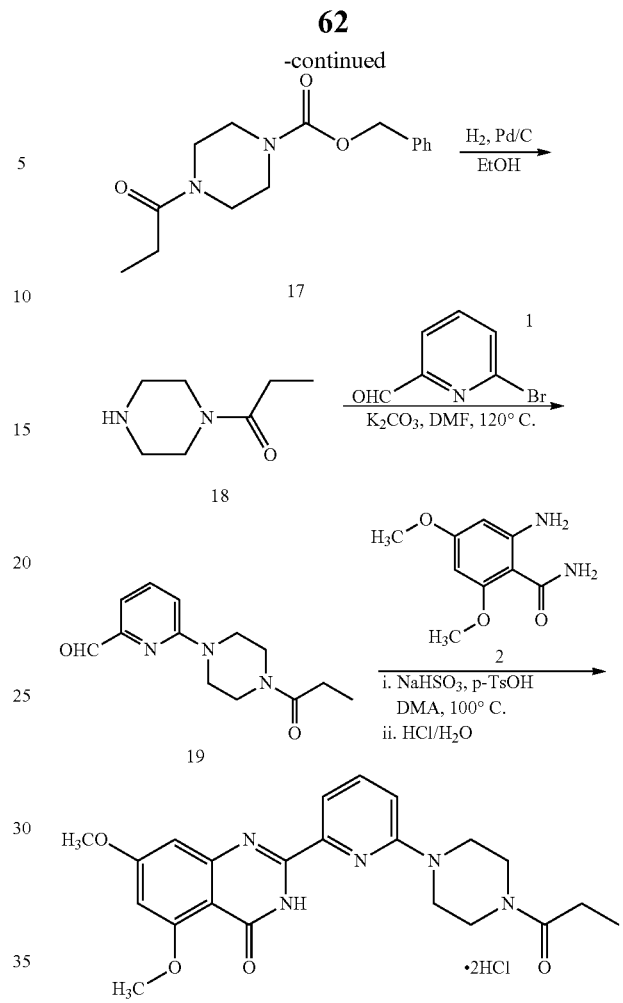

Example 19

Preparation of Benzyl 4-propionylpiperazine-1-carboxylate (17): A solution of benzyl piperazine-1-carboxylate (16, 10.0 g, 45.4 mmol), triethylamine (6.89 g, 68.0 mmol) and dry $CH_2Cl_2$ (150 mL) was cooled to 0° C. and propionyl chloride (4.62 g, 50.0 mmol) was added dropwise over 10 min. The reaction was kept under nitrogen and allowed to warm to room temperature. After stirring at rt for 17 h, water (50 mL) was added and the aqueous layer was extracted with $CH_2Cl_2$ (2×50 mL). The solution was dried over $Na_2SO_4$, filtered and concentrated to a yellow oil. The product was purified by silica gel chromatography eluting with 0-3% $CH_3OH$ in $CH_2Cl_2$ to afford the title compound (9.08 g, 72%) as a clear, colorless oil: $^1$H NMR (500 MHz, $CDCl_3$) δ 7.40-7.30 (m, 5H), 5.15 (s, 2H), 3.70-3.35 (m, 8H), 2.35 (q, J=7.5 Hz, 2H), 1.15 (t, J=7.5 Hz, 3H).

Preparation of 1-(Piperazin-1-yl)propan-1-one (18): A Parr shaker bottle was charged with a suspension of benzyl 4-propionylpiperazine-1-carboxylate (16), 10% palladium on carbon, 50% wet (900 mg) and absolute ethanol (100 mL). The Parr bottle was filled with 20 psi of hydrogen and shook for 3 h at rt. The resulting suspension was filtered through Celite and concentrated to yield the title compound (4.31 g, 93%) as a clear, colorless oil: $^1$H NMR (500 MHz, $CDCl_3$) δ 3.75-3.63 (m, 2H), 3.48-3.42 (m, 2H), 2.87-2.80 (m, 4H), 2.34 (q, J=7.5 Hz, 2H), 1.98 (br s, 1H), 1.15 (t, J=7.5 Hz, 3H).

Preparation of 6-(4-Propionylpiperazin-1-yl)picolinaldehyde (19): To a high-pressure tube was added 6-bromopicolinaldehyde (1, 2.00 g, 10.7 mmol), 1-(piperazin-1-yl)propan-1-one (18, 3.82 g, 26.9 mmol), potassium carbonate (6.69 g, 48.4 mmol) and anhydrous DMF (12 mL). The tube was sealed and the reaction mixture was heated at 120° C. for 17 h. The reaction suspension was poured into water (100 mL) and the mixture was brought to pH 7 using 2 N aq. HCl (20 mL). The solution was extracted with $CH_2Cl_2$ (3×100 mL), washed with brine (300 mL), dried over $Na_2SO_4$, filtered and concentrated to a brown oil. The product was purified by silica gel chromatography eluting with 0-5% $CH_3OH$ in $CH_2Cl_2$ to afford the title compound (0.815 g, 31%) as an orange solid: $^1H$ NMR (500 MHz, $CDCl_3$) δ 9.89 (s, 1H), 7.68 (t, J=8.0 Hz, 1H), 7.33 (d, J=8.0 Hz, 1H), 6.84 (d, J=8.0 Hz, 1H), 3.84-3.73 (m, 2H), 3.68-3.59 (m, 2H), 2.40 (q, J=7.5 Hz, 2H), 1.19 (t, J=7.5 Hz, 3H).

Preparation of 5,7-Dimethoxy-2-(6-(4-propionylpiperazin-1-yl)pyridin-2-yl)quinazolin-4(3H)-one dihydrochloride (Example 19): Following the method described for Example 15 above, Example 19 was made from 6-(4-propionylpiperazin-1-yl)picolinaldehyde (19) in 15% yield: $^1H$ NMR (500 MHz, $CD_3OD$) δ 7.91 (t, J=8.0 Hz, 1H), 7.70 (d, J=7.5 Hz, 1H), 7.31 (d, J=8.5 Hz, 1H), 7.10 (d, J=2.0 Hz, 1H), 6.83 (d, J=2.0 Hz, 1H), 4.02 (s, 3H), 4.01 (s, 3H), 3.90-3.72 (m, 8H), 2.51 (q, J=7.5 Hz, 2H), 1.17 (t, J=7.5 Hz, 3H); ESI MS m/z 424 $[M+H]^+$.

Example 20

Preparation of 2-(3-(4-Isopropylpiperazin-1-yl)-5-(trifluoromethoxy)phenyl)-5,7-dimethoxyquinazolin-4(3H)-one

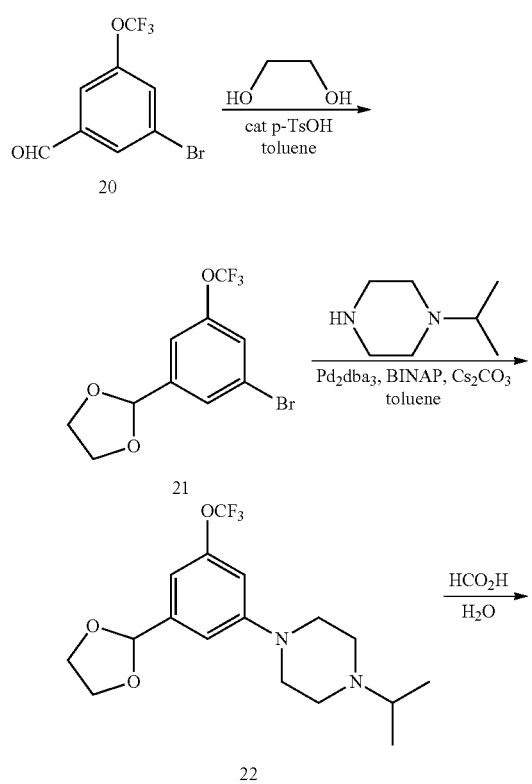

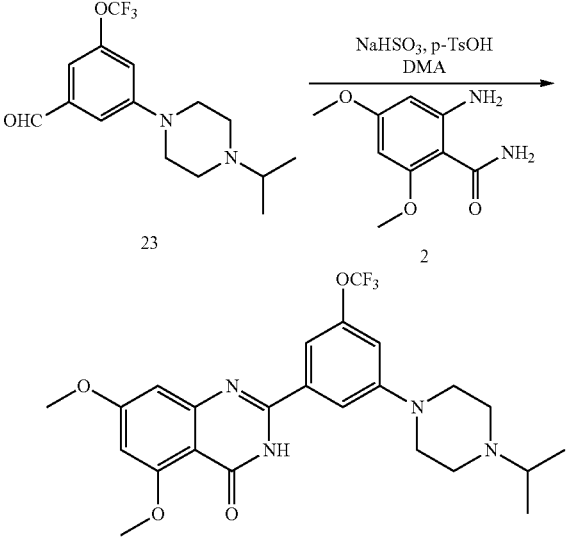

Example 20

Preparation of 2-(3-Bromo-5-(trifluoromethoxy)phenyl)-1,3-dioxolane (21): A solution of 3-bromo-5-trifluoromethoxybenzaldehyde (20, 2.00 g, 7.43 mmol), ethylene glycol (2.31 g, 37.2 mmol), para-toluenesulfonic acid (50 mg, 0.26 mmol) in anhydrous toluene (50 mL) was refluxed using a Dean-Stark apparatus for 3 h. The solution was concentrated and the product purified by silica gel chromatography eluting with 0-10% EtOAc in hexanes to afford the title compound (1.25 g, 54%) as a clear, colorless oil: $^1H$ NMR (500 MHz, $CDCl_3$) δ 7.57 (t, J=1.5 Hz, 1H), 7.37 (s, 1H), 7.28 (s, 1H), 5.79 (s, 1H), 4.12-4.01 (m, 4H).

Preparation of 1-(3-(1,3-Dioxolan-2-yl)-5-(trifluoromethoxy)phenyl)-4-isopropylpiperazine (22): Tris(dibenzylideneacetone)dipalladium(0) (363 mg, 0.396 mmol) was added to a suspension of 2-(3-bromo-5-(trifluoromethoxy)phenyl)-1,3-dioxolane (21, 1.24 g, 3.96 mmol), isopropylpiperazine (610 mg, 4.75 mmol), racemic-2,2'-bis(diphenylphosphino)-1,1'-binaphthyl (rac-BINAP, 345 mg, 0.554 mmol), cesium carbonate (2.58 g, 7.92 mmol) and anhydrous toluene (50 mL). The mixture was placed under nitrogen and heated to 100° C. for 17 h. The solvent was removed in vacuo and methanol (30 mL) and silica gel (30 g) were added. After removing the methanol the adsorbed crude product was purified by silica gel chromatography eluting with 0-60% EtOAc in hexanes to afford the title compound (996 mg, 70%) as an orange oil: $^1H$ NMR (500 MHz, $CDCl_3$) δ 6.93 (s, 1H), 6.78 (s, 1H), 6.68 (s, 1H), 5.77 (s, 1H), 4.17-3.99 (m, 4H), 3.26-3.22 (m, 4H), 2.72 (sept, 1H), 2.68-2.62 (m, 4H), 1.08 (d, J=6.5 Hz, 6H).

Preparation of 3-(4-Isopropylpiperazin-1-yl)-5-(trifluoromethoxy)benzaldehyde (23): Water (1.3 mL) was added to a suspension of 1-(3-(1,3-dioxolan-2-yl)-5-(trifluoromethoxy)phenyl)-4-isopropylpiperazine (22, 996 mg, 2.76 mmol) and formic acid (6.71 g, 145 mmol). The mixture was heated to 60° C. for 20 h. The reaction mixture was concentrated to a brown oil in vacuo. The oil was dissolved in EtOAc (100 mL) and the solution was washed with saturated aq. $NaHCO_3$ solution (100 mL) and brine (100 mL). After drying over $Na_2SO_4$, the suspension was filtered and the filtrate concentrated to an orange oil. The residue was purified by silica gel chromatography eluting with 0-80% EtOAc in hexanes to afford the title compound (608 mg, 70%) as an orange oil: $^1$H NMR (500 MHz, CDCl$_3$) δ 9.92 (s, 1H), 6.93 (s, 1H), 7.31 (s, 1H), 7.13 (s, 1H), 6.92 (s, 1H), 3.30-3.28 (m, 4H), 2.73 (sept, 1H), 2.70-2.64 (m, 4H), 1.10 (d, J=6.5 Hz, 6H).

Preparation of 2-(3-(4-Isopropylpiperazin-1-yl)-5-(trifluoromethoxy)phenyl)-5,7-dimethoxyquinazolin-4(3H)-one (Example 20): Following the method described for Example 15 above, Example 20 was made from 3-(4-isopropylpiperazin-1-yl)-5-(trifluoromethoxy)benzaldehyde (23) in 49% yield: $^1$H NMR (500 MHz, DMSO-d$_6$) δ 12.1 (s, 1H), 7.72 (s, 1H), 7.51 (s, 1H), 7.01 (s, 1H), 6.77 (d, J=2.0 Hz, 1H), 6.55 (d, J=2.0 Hz, 1H), 3.90 (s, 3H), 3.87 (s, 3H), 3.35-3.28 (m, 4H), 2.70 (sept, 1H), 2.61-2.56 (m, 4H), 1.02 (d, J=6.5 Hz, 6H). ESI MS m/z 493 [M+H]$^+$.

Example 21

Preparation of 7-Fluoro-2-(6-(4-isopropylpiperazin-1-yl)pyridin-2-yl)-5-methoxyquinazolin-4(3H)-one Hydrochloride

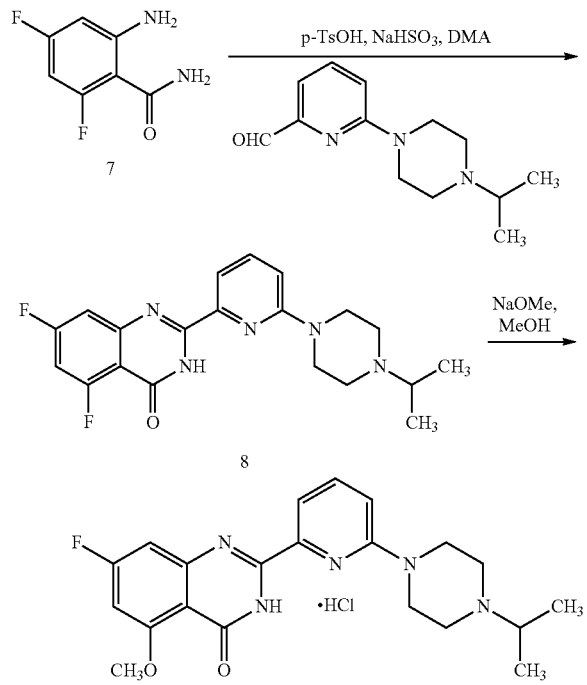

Example 21

Preparation of 5,7-Difluoro-2-(6-(4-isopropylpiperazin-1-yl)pyridin-2-yl)quinazolin-4(3H)-one (8): A mixture of 2-amino-4,6-difluorobenzamide (7, 330 mg, 1.70 mmol), 6-(4-isopropylpiperazin-1-yl)picolinaldehyde (8, Scheme 6, 330 mg, 1.42 mmol), p-toluenesulfonic acid (590 mg, 3.12 mmol), NaHSO$_3$ (370 mg, 3.55 mmol) and DMA (15 mL) was heated for 24 h at 110° C. under nitrogen. The mixture was partitioned between water (25 mL) and CH$_2$Cl$_2$ (25 mL) and shaken vigorously. The layers were separated and the organic phase was dried over sodium sulfate and filtered. The solvent was removed under reduced pressure and the residue was purified by silica gel chromatography eluting with 0-5% MeOH in CH$_2$Cl$_2$ to provide the title compound (112 mg, 20%): $^1$H NMR (500 MHz, CDCl$_3$) δ 10.59 (s, 1H), 7.85 (d, J=7.3 Hz, 1H), 7.67 (dd, J=7.3, 8.5 Hz, 1H), 7.30-7.26 (m, 1H), 6.93-6.89 (m, 1H), 6.86 (d, J=8.5 Hz, 1H), 3.69-3.60 (m, 4H), 2.82-2.73 (m, 1H), 2.71-2.66 (m, 4H), 1.12 (s, 3H), 1.11 (s, 3H).

Preparation of 7-Fluoro-2-(6-(4-isopropylpiperazin-1-yl)pyridin-2-yl)-5-methoxyquinazolin-4(3H)-one Hydrochloride (Example 21): To a solution of 5,7-difluoro-2-(6-(4-isopropylpiperazin-1-yl)pyridin-2-yl)quinazolin-4(3H)-one (8, 44 mg, 0.11 mmol) and MeOH (5 mL) was added NaOMe (25% solution in MeOH) at room temperature. After stirring overnight, the solvent was removed under reduced pressure and the residue partitioned between water and CH$_2$Cl$_2$. The organic phase was dried over sodium sulfate and filtered. The solvent was removed under reduced pressure and the residue was purified by preparative HPLC followed by treatment with aqueous HCl to provide the title compound (7.5 mg, 17%) as an white solid: $^1$H NMR (500 MHz, CD$_3$OD) δ 7.90 (d, J=7.2 Hz, 1H), 7.82 (dd, J=7.4, 8.3 Hz, 1H), 7.14 (d, J=8.4 Hz, 1H), 7.06-6.99 (m, 1H), 6.93-6.85 (m, 1H), 4.79-4.66 (m, 2H), 3.98 (s, 3H), 3.71-3.56 (m, 3H), 3.29-3.19 (m, 3H), 1.44 (s, 3H), 1.43 (s, 3H); ESI MS m/z 398 [M+H]$^+$.

Example 22

Preparation of 7-(Benzyloxy)-2-(6-(4-isopropylpiperazin-1-yl)pyridin-2-yl)-5-methoxyquinazolin-4(3H)-one Hydrochloride

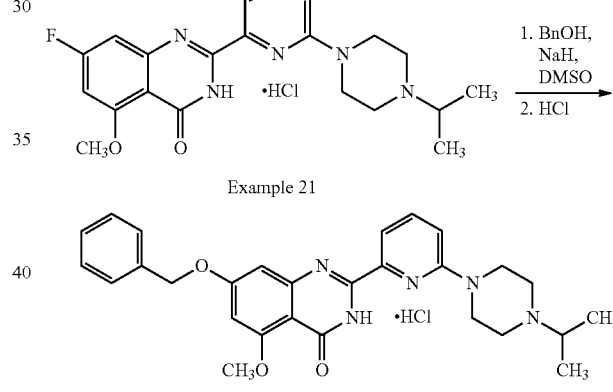

Preparation of 7-(Benzyloxy)-2-(6-(4-isopropylpiperazin-1-yl)pyridin-2-yl)-5-methoxyquinazolin-4(3H)-one Hydrochloride (Example 22): To a mixture of NaH (58 mg, 1.44 mmol) and DMSO (2.0 mL) at room temperature was slowly added a solution of benzyl alcohol (173 mg, 1.6 mmol) in DMSO (3.0 mL). After stirring the mixture for 20 min, a solution of 7-fluoro-2-(6-(4-isopropylpiperazin-1-yl)pyridin-2-yl)-5-methoxyquinazolin-4(3H)-one (9, 65 mg, 0.16 mmol) in DMSO (3 mL) was slowly added. The reaction mixture was then heated at 80° C. for 14 h. The reaction mixture was cooled to room temperature and water (50 mL) was added. The precipitated solid was collected by filtration and purified by silica gel chromatography eluting with 0-5% MeOH in CH$_2$Cl$_2$ followed by treatment with aqueous HCl to provide the title compound (38 mg, 49%) as an off-white solid: $^1$H NMR (500 MHz, CD$_3$OD) δ 7.95-7.88 (m, 1H), 7.83 (d, J=7.4 Hz, 1H), 7.50-7.46 (m, 2H), 7.43-7.38 (m, 2H), 7.38-7.33 (m, 1H), 7.30 (d, J=8.6 Hz, 1H), 7.08 (s, 1H), 6.84 (s, 1H), 5.30 (s, 2H), 4.83-4.77 (m, 2H), 3.98 (s, 3H), 3.68-

3.57 (m, 3H), 3.42-3.33 (m, 2H), 3.29-3.21 (m, 2H), 1.44 (s, 3H), 1.43 (s, 3H); ESI MS m/z 486 [M+H]⁺.

Example 23

Preparation of 7-(4-Isopropylpiperazin-1-yl)-2-(6-(4-isopropylpiperazin-1-yl)pyridin-2-yl)-5-methoxyquinazolin-4(3H)-one Hydrochloride

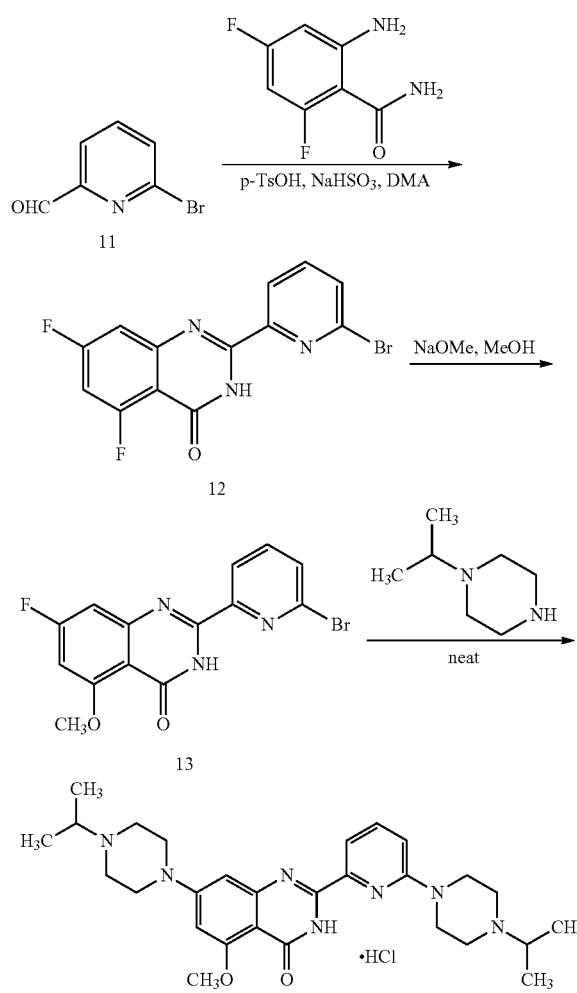

Example 23

Preparation of 2-(6-Bromopyridin-2-yl)-5,7-difluoroquinazolin-4(3H)-one (12): A mixture of 6-bromopicolinaldehyde (2.8 g, 15 mmol), 2-amino-4,6-difluorobenzamide (2.5 g, 10 mmol), p-toluenesulfonic acid (4.2 g, 22 mmol), NaHSO₃ (2.6 g, 25 mmol) and DMA (40 mL) was heated at 110° C. for 48 h in a sealed tube. The reaction mixture was cooled to room temperature and partitioned between water and EtOAc (25 mL). The aqueous phase was extracted with EtOAc (2×25 mL). The organic layers were combined, dried over sodium sulfate, filtered and the solvent was removed under reduced pressure. The product was purified by crystallization (EtOAc) to provide the title compound (500 mg, 15%): ¹H NMR (500 MHz, DMSO-d₆) δ 11.97 (s, 1H), 8.32 (d, J=7.7, 0.7 Hz, 1H), 8.05-7.96 (m, 1H), 7.91 (dd, J=7.7, 0.7 Hz, 1H), 7.46-7.29 (m, 2H).

Preparation of 2-(6-bromopyridin-2-yl)-7-fluoro-5-methoxyquinazolin-4(3H)-one (13): To a mixture of 2-(6-bromopyridin-2-yl)-5,7-difluoroquinazolin-4(3H)-one (12, 1.05 g, 3.11 mmol) and MeOH (15 mL) was added NaOMe (25% solution, 50 mL) at room temperature. After 24 hours, another portion of 25% NaOMe was added (25 mL). After an additional 48 hours at room temperature, the reaction was quenched with water and the pH adjusted to 7 with 2N HCl. The volume was reduced by half under reduced pressure and the remaining mixture was extracted with CH₂Cl₂ (3×250 mL). The combined organic phases were dried over sodium sulfate, filtered and concentrated under reduced pressure to provide the title compound (970 mg, 89%) as an off-white solid. ¹H NMR (500 MHz, CDCl₃) δ 10.56 (s, 1H), 8.57-8.43 (m, 1H), 7.79-7.74 (m, 1H), 7.71-7.62 (m, 1H), 7.09-6.99 (m, 1H), 6.71-6.65 (m, 1H), 4.02 (s, 3H).

Preparation of 7-(4-Isopropylpiperazin-1-yl)-2-(6-(4-isopropylpiperazin-1-yl)pyridin-2-yl)-5-methoxyquinazolin-4(3H)-one Hydrochloride (Example 23): A solution of 2-(6-bromopyridin-2-yl)-7-fluoro-5-methoxyquinazolin-4(3H)-one (13, 100 mg, 0.29 mmol) and 1-isopropylpiperazine (5 mL) was heated at 80° C. for 18 hours. Water (25 mL) was added and the mixture was extracted with CH₂Cl₂ (2×25 mL). The combined extracts were dried over sodium sulfate and filtered. The solvent was removed under reduced pressure and the residue was purified by silica gel chromatography 0-10% MeOH in CH₂Cl₂. The product was further purified by preparative HPLC followed by treatment with aqueous HCl to provide the title compound (62 mg, 54%) as a white solid: ¹H NMR (300 MHz, CD₃OD) δ 7.85-7.79 (m, 1H), 7.78-7.74 (m, 1H), 7.20-7.14 (m, 1H), 6.67-6.59 (m, 1H), 4.78-4.66 (m, 1H), 4.24-4.14 (m, 1H), 3.93-3.85 (s, 3H), 3.57-3.36 (m, 16H), 3.19-3.00 (m, 4H), 1.33 (s, 6H), 1.32 (s, 6H); ESI MS m/z 506 [M+H]⁺.

Example 24

Preparation of intermediate 3-Amino-5-methoxy-[1,1'-biphenyl]-4-carboxamide

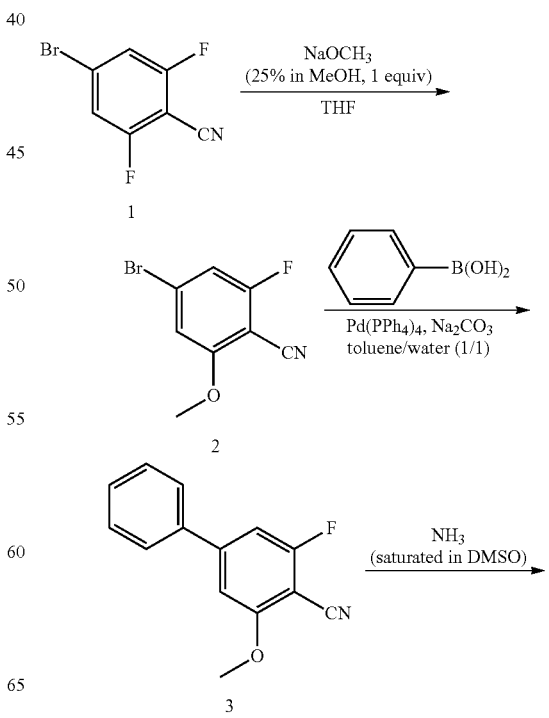

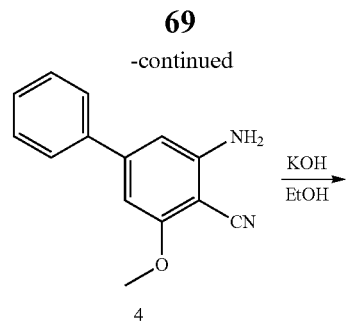

4

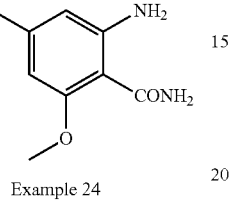

Example 24

Preparation of 4-Bromo-2-fluoro-6-methoxybenzonitrile (2): To a solution of 4-bromo-2,6-difluorobenzonitrile (1, 15.0 g, 69 mmol) in THF (100 mL) at 0° C. was slowly added sodium methoxide (25% wt in methanol, 14.9 g, 69 mmol) and the mixture was stirred at room temperature for 16 h. The mixture was concentrated and partitioned between dichloromethane (500 mL) and water (250 mL). The organic extracts were dried (MgSO$_4$), filtered, and concentrated. The residue was purified by silica gel chromatography eluting with ethyl acetate in hexane (0-100%) to afford the title compound (15.2 g, 99%) as a white solid: $^1$H NMR (500 MHz, CDCl$_3$) δ 7.01-6.99 (m, 1H), 6.94 (s, 1H), 3.96 (s, 1H).

Preparation of 3-Fluoro-5-methoxy-[1,1'-biphenyl]-4-carbonitrile (3): A mixture of 4-bromo-2-fluoro-6-methoxybenzonitrile (2, 5.22 g, 22.7 mmol), phenylboronic acid (4.15 g, 34 mmol) and 2 M Na$_2$CO$_3$ (23 mL) in toluene (100 mL) was purged with N$_2$ for 10 min. Pd(PPh$_4$)$_3$ (2.62 g, 27.7 mmol) and EtOH (5 drops) were added. The mixture was then heated under N$_2$ in a sealed tube at 80° C. for 18 h. The mixture was cooled to room temperature, diluted with EtOAc (300 mL), filtered through celite, concentrated and purified by silica gel chromatography eluting with ethyl acetate in hexane (0-100%) to afford the title compound (5.05 g, 97%) as a white solid: $^1$H NMR (500 MHz, CDCl$_3$) δ 7.57-7.55 (m, 2H), 7.50-7.23 (m, 3H), 7.01-6.99 (m, 1H), 6.93 (s, 1H), 3.95 (s, 3H).

Preparation of 3-Amino-5-methoxy-[1,1'-biphenyl]-4-carbonitrile (4): A solution of 3-fluoro-5-methoxy-[1,1'-biphenyl]-4-carbonitrile (3, 4.0 g, 17.6 mmol) in ammonia saturated DMSO (100 mL) was heated in an autoclave at 150° C. for 18 h. After this time, the mixture was cooled to room temperature, concentrated and purified by silica gel chromatography eluting with ethyl acetate in hexane (0-100%) to afford the title compound (2.06 g, 52%) as a light yellow solid: $^1$H NMR (500 MHz, CDCl$_3$) δ 7.54-7.52 (m, 2H), 7.46-7.43 (m, 2H), 7.41-7.38 (m, 1H), 6.52 (d, J=1.0 Hz, 1H), 6.43 (d, J=1.0 Hz, 1H), 4.43 (br s, 2H), 3.93 (s, 3H).

Preparation of 3-Amino-5-methoxy-[1,1'-biphenyl]-4-carboxamide (Example 24): A mixture of 3-amino-5-methoxy-[1,1'-biphenyl]-4-carbonitrile (4, 0.64 g, 2.86 mmol) and KOH (1.12 g, 20 mmol) in EtOH (24 mL) in a sealed tube was heated at 100° C. for 18 h. Additional KOH (0.56 g, 10 mmol) was added and heating was continued for another 18 h. After this time, the mixture was cooled to room temperature, and the pH was adjusted to ~2 by addition of concentrated HCl. After concentration, the residue was partitioned between ethyl acetate (100 mL) and water (50 mL). The extracts were washed with brine (50 mL), dried (Na$_2$SO$_4$), filtered, and concentrated. The residue was purified by silica gel chromatography eluting with methanol in dichloromethane (0-20%) to afford the title compound (0.28 g, 40%) as a yellow solid: $^1$H NMR (500 MHz, DMSO-d$_6$) δ 7.62-7.60 (m, 2H), 7.58 (s, 1H), 7.47-7.44 (m, 2H), 7.39-7.36 (m, 1H), 7.28 (s, 1H), 6.61 (d, J=1.5 Hz, 1H), 6.56 (s, 2H), 6.43 (d, J=1.5 Hz, 1H), 3.87 (s, 3H); ESI MS m/z 243 [M+H]$^+$.

Example 25

Preparation of 2-(6-(4-Isopropylpiperazin-1-yl)pyridin-2-yl)-5-methoxy-7-phenylquinazolin-4(3H)-one

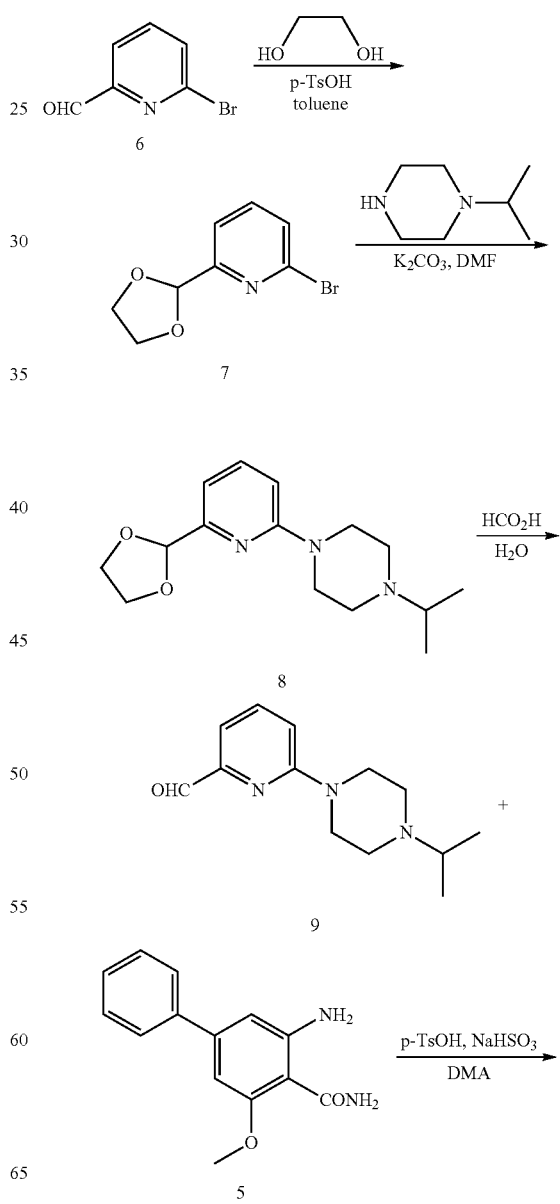

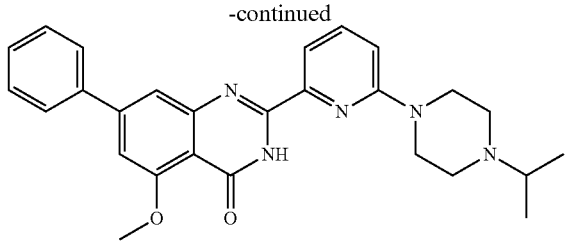

Example 25

Preparation of 2-Bromo-6-(1,3-dioxolan-2-yl)pyridine (7): A solution of 6-bromopicolinaldehyde (6, 10.0 g, 53.8 mmol), ethylene glycol (16.7 g, 26.9 mmol), para-toluenesulfonic acid (100 mg) in dry toluene (250 mL) was refluxed for 3 h while using a Dean-Stark apparatus. The solution was concentrated in vacuo and the remaining dark yellow oil was purified by silica gel chromatography eluting with 0-40% EtOAc in hexanes to afford the title compound (10.4 g, 84%) as a clear, colorless oil: $^1$H NMR (500 MHz, CDCl$_3$) δ 7.59 (t, J=7.5 Hz, 1H), 7.53-7.44 (m, 2H), 7.25 (d, J=8.0 Hz, 1H), 5.81 (s, 1H), 4.25-4.03 (m, 4H).

Preparation of 1-[6-(1,3-Dioxolan-2-yl)pyridin-2-yl]-4-isopropylpiperazine (8): A mixture of 2-bromo-6-(1,3-dioxolan-2-yl)pyridine (7, 0.23 g, 1.0 mmol) and 1-isopropylpiperazine (0.38 g, 3.0 mmol) in a sealed tube was heated at 120° C. for 18 h. The mixture was cooled to room temperature, diluted with ethyl acetate (50 mL), washed with water (10 mL), brine (10 mL), dried (Na$_2$SO$_4$), filtered, and concentrated. The residue was purified by silica gel chromatography eluting with 0-10% methanol in dichloromethane to afford the title compound (0.15 g, 55%) as a yellow oil: $^1$H NMR (500 MHz, CDCl$_3$) δ 7.51-7.48 (m, 1H), 6.83-6.82 (m, 1H), 6.62-6.60 (m, 1H), 5.72 (s, 1H), 4.18-4.14 (m, 2H), 4.08-4.04 (m, 2H), 3.58 (br s, 4H), 2.71 (br s, 1H), 2.62 (br s, 2H), 1.08 (d, J=5.5 Hz, 6H); ESI MS m/z 278 [M+H]$^+$.

Preparation of 6-(4-Isopropylpiperazin-1-yl)picolinaldehyde (9): A mixture of 1-[6-(1,3-dioxolan-2-yl)pyridin-2-yl]-4-isopropylpiperazine (8, 0.31 g, 1.1 mmol), formic acid (2.50 g, 50 mmol) and water (0.5 mL) was heated at 60° C. for 5 h. After this time, the mixture was concentrated and the residue was purified by silica gel chromatography eluting with 0-10% methanol in dichloromethane to afford the title compound (0.21 g, 82%) as a yellow oil; ESI MS m/z 234 [M+H]$^+$.

Preparation of 2-(6-(4-Isopropylpiperazin-1-yl)pyridin-2-yl)-5-methoxy-7-phenylquinazolin-4(3H)-one (Example 25): A solution of 3-amino-5-methoxy-[1,1'-biphenyl]-4-carboxamide (5, 0.048 g, 0.2 mmol) and 6-(4-isopropylpiperazin-1-yl)picolinaldehyde (9, 0.046 g, 0.2 mmol) in DMA (2 mL) was treated with p-TsOH (0.084 g, 0.44 mmol) and NaHSO$_3$ (0.042 g, 0.5 mmol) and then heated at 120° C. for 3 days. After this time, the reaction mixture was cooled to room temperature, diluted with saturated NaHCO$_3$, extracted with CH$_2$Cl$_2$ (2×15 mL), dried (MgSO$_4$), filtered, and concentrated. The residue was purified by silica gel chromatography eluting with 0-20% methanol in dichloromethane to afford the title compound (0.017 g, 19%) as a white solid: $^1$H NMR (500 MHz, CDCl$_3$) δ 11.16 (br s, 1H), 7.88-7.86 (m, 2H), 7.78-7.73 (m, 2H), 7.55-7.53 (m, 3H), 7.49-7.46 (m, 1H), 7.28-7.27 (m, 1H), 7.09-7.07 (m, 1H), 4.08 (s, 3H), 3.64 (br s, 4H), 2.60 (m, 1H), 2.46 (s, 4H), 0.98 (br s, 6H); ESI MS m/z 456 [M+H]$^+$.

Example 26

Preparation of 8-(Benzyloxy)-2-(3-(4-isopropylpiperazin-1-yl)phenyl)-5-methoxyquinazolin-4(3H)-one

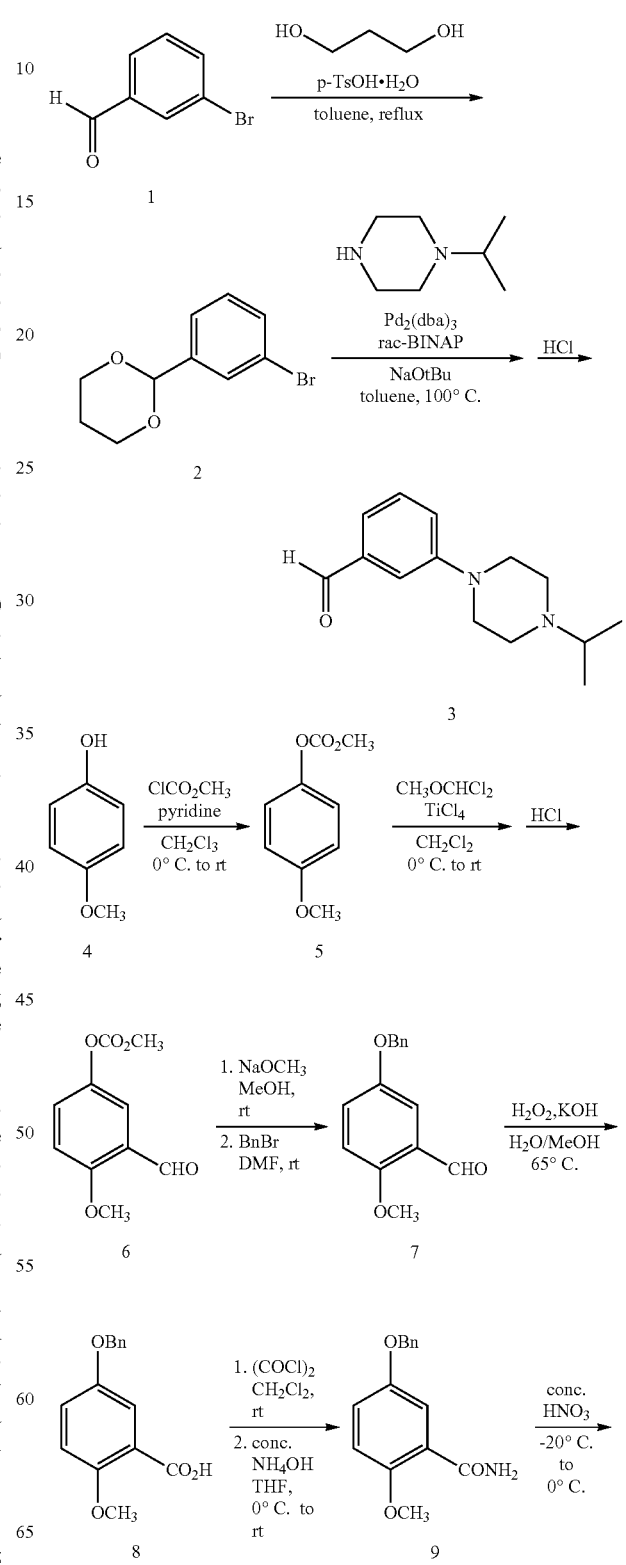

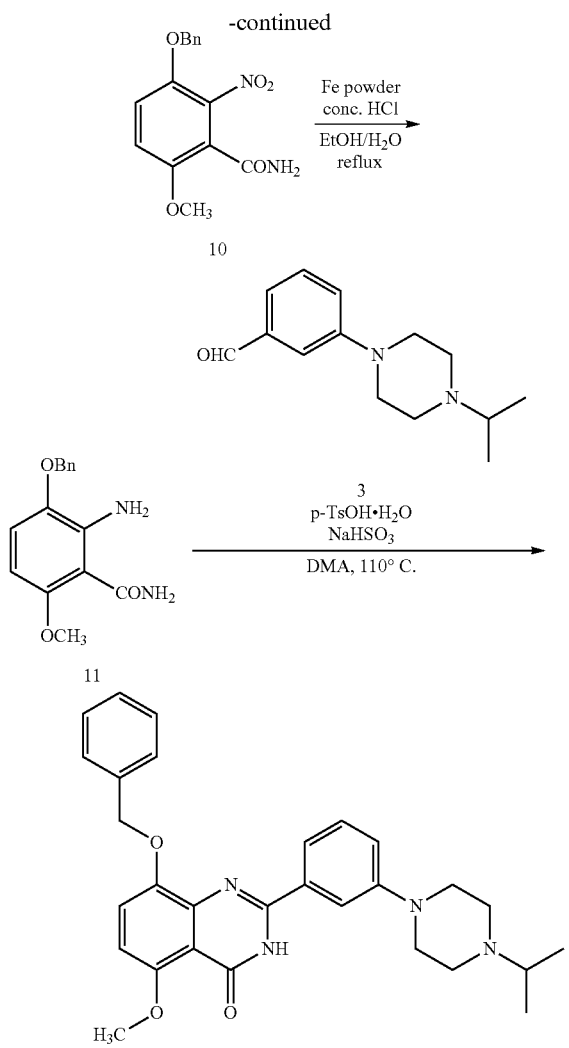

Example 26

Preparation of 2-(3-Bromophenyl)-1,3-dioxane (2): A solution of 3-bromobenzaldehyde (1, 18.5 g, 100 mmol), propane-1,3-diol (9.1 g, 120 mmol) and p-toluenesufonic acid monohydrate (0.1 g, 0.5 mmol) in toluene (200 mL) was refluxed with azeotropical removal of water using a Dean-Stark water separator for 15.5 h. The reaction mixture was cooled to room temperature, washed with 5% potassium carbonate solution (100 mL) and water (2×100 mL), dried over sodium sulfate and filtered. The filtrate was concentrated to afford the title compound (24.8 g, 100%): $^1$H NMR (500 MHz, CDCl$_3$) δ 7.66 (t, J=1.8 Hz, 1H), 7.46 (ddd, J=7.9, 2.0, 1.1 Hz, 1H), 7.40 (br d, J=7.9 Hz, 1H), 7.23 (t, J=7.9 Hz, 1H), 5.46 (s, 1H), 4.28-4.25 (m, 2H), 4.00-3.95 (m, 2H), 2.26-2.17 (m, 1H), 1.47-1.43 (m, 1H); ESI MS m/z 243, 245 [M+H]$^+$.

Preparation of 3-(4-Isopropylpiperazin-1-yl)benzaldehyde (3): A mixture of 2-(3-bromophenyl)-1,3-dioxane (2, 1.58 g, 6.5 mmol), 1-isopropylpiperazine (1.0 g, 7.8 mmol), rac-BINAP (60 mg, 0.096 mmol), and tert-BuONa (1.06 g, 11.1 mmol) in toluene (15 mL) was degassed under vacuum and flushed with nitrogen. Pd$_2$(dba)$_3$ (30 mg, 0.033. mmol) was added. The reaction mixture was degassed again and flushed with nitrogen and was heated at 100° C. under nitrogen for 16 h. The reaction mixture was poured into cold 1N HCl (30 mL) and stirred for 2 h. It was adjusted to pH 8 with 6N NaOH and extracted with EtOAc (3×50 mL). The combined organic layers were dried (MgSO$_4$), filtered, concentrated, and purified by silica gel chromatography eluting with 0-100% EtOAc (containing 5% v/v Et$_3$N) in hexanes to afford the title compound as a viscous yellow oil (1.32 g, 87%): $^1$H NMR (500 MHz, CDCl$_3$) δ 9.96 (s, 1H), 7.44-7.37 (m, 2H), 7.34-7.30 (m, 1H), 7.21-7.16 (m, 1H), 3.28 (t, J=5.0 Hz, 4H), 2.73 (sept, J=6.5 Hz, 1H), 2.69 (t, J=5.0 Hz, 4H), 1.10 (d, J=6.5 Hz, 6H); ESI MS m/z 233 [M+H]$^+$.

Preparation of 4-Methoxyphenyl Methyl Carbonate (5): To a stirred solution of 4-methoxyphenol (4, 12.4 g, 100 mmol) and pyridine (8.5 mL, 105 mmol) in CH$_2$Cl$_2$ (75 mL) at 0° C. was added ClCO$_2$Me (8.1 mL, 105 mmol) dropwise. The reaction mixture was allowed to warm to room temperature and stirred at room temperature for 1 h. The mixture was washed with 1N HCl, saturated NaHCO$_3$ solution and water, dried (Na$_2$SO$_4$), filtered, and concentrated. The residue was subjected to vacuum distillation (bp 84-92° C./ca. 1 mmHg) to afford the title compound (16.5 g, 91%) as a colorless oil: $^1$H NMR (500 MHz, CDCl$_3$) δ 7.09 (J=9.1 Hz, 2H), 6.89 (d, J=9.1 Hz, 2H), 3.89 (s, 3H), 3.80 (s, 3H).

Preparation of 3-Formyl-4-methoxyphenyl Methyl Carbonate (6): To a stirred solution of 4-methoxyphenyl methyl carbonate (5, 16.5 g. 91 mmol) in CH$_2$Cl$_2$ (205 mL) at 0° C. was added dropwise TiCl$_4$(23.5 mL, 210 mmol) in CH$_2$Cl$_2$ (20 mL) over 30 min. Then MeOCHCl$_2$ (9.3 mL, 104 mmol) in CH$_2$Cl$_2$ (20 mL) was added dropwise over 30 min. The reaction mixture was allowed to warm to room temperature and stirred for 30 min. The reaction material was poured into a mixture of ice (210 g) and concentrated HCl (8.5 mL). EtOAc (200 mL) was added and the mixture was stirred vigorously for 30 min. The aqueous layer was extracted with EtOAc (2×100 mL). The combined organic layers were dried (Na$_2$SO$_4$), filtered, and concentrated. The residue was recrystallized from EtOAc/hexanes to afford the title compound (16.6 g, 87%) as a light yellow solid: $^1$H NMR (500 MHz, CDCl$_3$) δ 10.43 (s, 1H), 7.63 (d, J=3.1 Hz, 1H), 7.37 (dd, J=9.0, 3.1 Hz, 1H), 7.01 (d, J=9.0 Hz, 1H), 3.94 (s, 3H), 3.90 (s, 3H); ESI MS m/z 228 [M+H$_2$O]$^+$.

Preparation of 5-(Benzyloxy)-2-methoxybenzaldehyde (7): To a stirred solution of sodium methoxide (257 mg. 4.8 mmol) in MeOH (20 mL) at room temperature was added 3-formyl-4-methoxyphenyl methyl carbonate (6, 1.0 g, 4.8 mmol). The resulting orange solution was stirred for 45 min and concentrated to dryness. The residue was dissolved in DMF (2 mL) and treated with K$_2$CO$_3$ (1.3 g, 9.4 mmol) and BnBr (0.57 mL, 4.8 mL). The reaction mixture was stirred for 15 h and it was poured into water (20 mL). The precipitate was collected, washed with water and dried in vacuo to afford the title compound (1.13 g, 98%) as a light yellow solid: $^1$H NMR (500 MHz, CDCl$_3$) δ 10.44 (s, 1H), 7.49-7.41 (m, 3H), 7.40-7.36 (m, 2H), 7.35-7.30 (m, 1H), 7.21 (dd, J=9.1, 3.2 Hz, 1H), 6.95 (d, J=9.1 Hz, 1H), 5.05 (s, 2H), 3.90 (s, 3H); ESI MS m/z 243 [M+H]$^+$.

Preparation of 5-(Benzyloxy)-2-methoxybenzoic Acid (8): To a stirred suspension of 5-(benzyloxy)-2-methoxybenzaldehyde (7, 1.12 g. 4.6 mmol) in MeOH (8 mL) at room temperature was added a solution of KOH (1.04 g, 18.5 mmol) in water (1.4 mL). The mixture was heated to 65° C. and H$_2$O$_2$ (35 wt %; 4.0 mL, 46 mmol) was added dropwise over 105 min. The reaction mixture was stirred at 65° C. for 1 h. Then it was cooled to room temperature and acidified to pH 2 with 6N H$_2$SO$_4$. The precipitate was collected, washed with water and dried in vacuo to afford the title compound (1.16 g, 97%) as a white solid: $^1$H NMR (500 MHz, CDCl$_3$) δ 10.94 (br s, 1H), 7.80 (d, J=3.3 Hz, 1H), 7.44-7.37 (m, 4H), 7.35-

7.32 (m, 1H), 7.19 (dd, J=9.0, 3.3 Hz, 1H), 7.00 (d, J=9.0 Hz, 1H), 5.08 (s, 2H), 4.04 (s, 3H); ESI MS m/z 257 [M−H]⁻.

Preparation of 5-(Benzyloxy)-2-methoxybenzamide (9): To a stirred solution of 5-(benzyloxy)-2-methoxybenzoic acid (8, 1.16 g. 4.5 mmol) in CH₂Cl₂ (25 mL) at room temperature was added oxalyl chloride (1.5 mL, 17.9 mmol). The reaction mixture was stirred at room temperature for 2 h. It was concentrated to dryness to provide the crude acid chloride as a brown-yellow waxy solid. The crude acid chloride was dissolved in THF (10 mL) and was added dropwise to a stirred mixture of concentrated NH₄OH (20 mL) and THF (10 mL) at 0° C. The reaction mixture was warmed to room temperature and stirred for 1 h and was adjusted to pH 8 with 2 N HCl. The precipitate was collected, washed with water, and dried in vacuo to afford the title compound (0.73 g, 63%) as a white solid: ¹H NMR (500 MHz, CDCl₃) δ 7.88 (d, J=3.3 Hz, 1H), 7.82 (br s, 1H), 7.47-7.43 (m, 2H), 7.40-7.37 (m, 2H), 7.33-7.30 (m, 1H), 7.10 (dd, J=9.0, 3.3 Hz, 1H), 6.94 (d, J=9.0 Hz, 1H), 5.75 (br s, 1H), 5.08 (s, 2H), 3.94 (s, 3H); ESI MS m/z 258 [M+H]⁺.

Preparation of 3-(Benzyloxy)-6-methoxy-2-nitrobenzamide (10): To a stirred mixture of 5-(benzyloxy)-2-methoxybenzamide (9, 0.365 g. 1.4 mmol) and Ac₂O (1.2 mL) at 0° C. was added 70% HNO₃ (0.14 mL, 2.1 mmol). The reaction mixture was warmed to room temperature and stirred for 1 h. Then 4.5 mL of 70% HNO₃ precooled at −30° C. was added. The mixture was stirred at 0° C. for 1 h and was poured onto ice. The precipitate was collected, washed with water and dried in vacuo. Purification by silica gel chromatography eluting with 0-2.5% MeOH in CH₂Cl₂ afforded the title compound along with its regioisomer (0.34 g, 79%) as a yellow solid: ¹H NMR (500 MHz, CDCl₃) δ 7.73 (br s, 1H), 7.41-7.30 (m, 5H), 7.11 (d, J=9.2 Hz, 1H), 7.00 (d, J=9.2 Hz, 1H), 6.84 (br s, 1H), 5.15 (s, 2H), 3.91 (s, 3H); ESI MS m/z 303 [M+H]⁺.

Preparation of 2-Amino-3-(benzyloxy)-6-methoxybenzamide (11): A mixture of 3-(benzyloxy)-6-methoxy-2-nitrobenzamide (10, 0.34 g. 1.1 mmol), iron powder (0.44 g, 7.7 mmol) and concentrated hydrochloric acid (80 mL) in EtOH (4 mL)/water (0.4 mL) was heated at 90° C. for 75 min. The reaction mixture was cooled to room temperature, filtered through Celite and concentrated. The residue was dissolved in EtOAc washed with saturated NaHCO₃ solution, dried over Na₂SO₄, filtered, and concentrated. Purification by silica gel chromatography eluting with 0-10% MeOH in CH₂Cl₂ afforded the title compound along with its regioisomer (0.267 g, 87%) as a tan solid: ¹H NMR (500 MHz, CDCl₃) δ 7.83 (br s, 1H), 7.47-7.32 (m, 5H), 6.77 (d, J=8.8 Hz, 1H), 6.60 (br s, 2H), 6.06 (d, J=8.8 Hz, 1H), 5.51 (br s, 1H), 5.04 (s, 2H), 3.85 (s, 3H).

Preparation of 8-(Benzyloxy)-2-(3-(4-isopropylpiperazin-1-yl)phenyl)-5-methoxyquinazolin-4(3H)-one (Example 26): A solution of 2-amino-3-(benzyloxy)-6-methoxybenzamide (11, 0.267 g, 0.98 mmol) and 5-(benzyloxy)-2-methoxybenzaldehyde (3, 0.152 g, 0.65 mmol) in N,N-dimethylacetamide (10 mL) was treated with p-TsOH (0.30 g, 1.57 mmol) and NaHSO₃ (0.204 g, 1.96 mmol) and then heated at 110° C. for 15 h. The reaction mixture was cooled to room temperature, and concentrated under reduced pressure. The residue was purified by silica gel chromatography eluting with 0-100% 95:4.5:0.5 CH₂Cl₂/MeOH/concentrated NH₄OH in CH₂Cl₂ to afford the title compound (71 mg, 22%) as a light yellow solid: ¹H NMR (500 MHz, DMSO-d₆) δ 12.22 (s, 1H), 7.79 (s, 1H), 7.68 (d, J=7.6 Hz, 1H), 7.56 (d, J=7.3 Hz, 2H), 7.42-7.33 (m, 5H), 7.14 (d, J=7.6 Hz, 1H), 6.92 (d, J=9.0 Hz, 1H), 5.24 (s, 2H), 3.83 (s, 3H), 3.34-3.31 (m, 4H), 2.80-2.60 (m, 5H), 1.05 (br s, 6H); ESI MS m/z 485 [M+H]⁺.

Example 27

Preparation of 4-(6-(5,7-Dimethoxy-4-oxo-3,4-dihydroquinazolin-2-yl)pyridin-2-yl)-N-isopropylpiperazine-1-carboxamide Hydrochloride

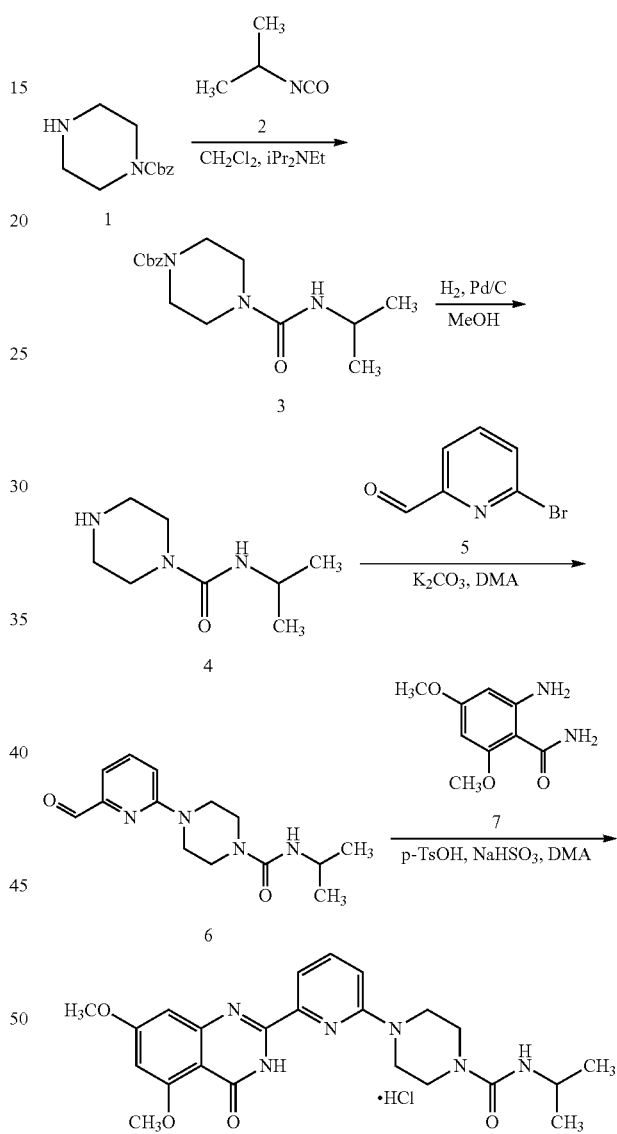

Example 27

Preparation of Benzyl 4-(Isopropylcarbamoyl)piperazine-1-carboxylate (3): To a solution of benzyl piperazine-1-carboxylate (1, 5.0 g, 23 mmol) and diisopropylethylamine (5.86 g, 45.4 mmol) in dichloromethane (50 mL) was added 2-isocyanatopropane (4.83 g, 56.8 mmol) and the mixture was stirred overnight at room temperature. The mixture was diluted with EtOAc (300 mL), washed with water (100 mL), dried (Na₂SO₄), filtered, and concentrated. The residue was purified by silica gel chromatography eluting with to 0-20% CH₂Cl₂/92:7:1 CHCl₃/MeOH/concentrated NH₄OH in CH$_2$Cl$_2$ to afford the title compound (3.94 g, 57%) as a white solid: $^1$H NMR (300 MHz, CDCl$_3$) δ 7.45-7.25 (m, 5H), 5.14 (s, 2H), 4.19 (d, J=6.7 Hz, 1H), 4.05-3.90 (m, 1H), 3.60-3.45 (m, 4H), 3.44-3.25 (m, 4H), 1.20-1.10 (m, 6H); Multimode MS m/z 306 [M+H]$^+$.

Preparation of N-Isopropylpiperazine-1-carboxamide (4): To a solution of benzyl 4-(isopropylcarbamoyl)piperazine-1-carboxylate (3, 3.94 g, 12.9 mmol) in methanol (100 mL) was added 10% Pd/C (50% wet, 0.400 g) and the mixture was stirred under 1 atmosphere of hydrogen for 16 h. After this time, the mixture was filtered through Celite and the filtrate concentrated to afford the title compound (2.88 g, >99%): $^1$H NMR (300 MHz, CD$_3$OD) δ 4.00-3.80 (m, 1H), 3.45-3.35 (m, 4H), 2.88-2.78 (m, 4H), 1.13 (d, J=6.5 Hz, 6H); Multimode MS m/z 172 [M+H]$^+$.

Preparation of 4-(6-Formylpyridin-2-yl)-N-isopropylpiperazine-1-carboxamide (6): A mixture of 6-bromopicolinaldehyde (5, 1.00 g, 5.38 mmol) and N-isopropylpiperazine-1-carboxamide (4, 1.10 g, 6.45 mmol) in N,N-dimethylacetamide (20 mL) was treated with K$_2$CO$_3$ (2.23 g, 16.1 mmol) and heated at 80° C. for 18 h. The mixture was cooled to room temperature and concentrated. The residue was purified by silica gel chromatography eluting with hexanes to 100% EtOAc to 4:1 EtOAc/MeOH to afford the title compound (0.35 g, 24%) as an impure yellow solid: Multimode MS m/z 172 [M+H]$^+$.

Preparation of 4-(6-(5,7-Dimethoxy-4-oxo-3,4-dihydroquinazolin-2-yl)pyridin-2-yl)-N-isopropylpiperazine-1-carboxamide Hydrochloride (Example 27): A solution of 4-(6-formylpyridin-2-yl)-N-isopropylpiperazine-1-carboxamide (6, 0.350 g, 1.27 mmol) and 2-amino-4,6-dimethoxybenzamide (7, 0.165 g, 0.845 mmol) in DMA (5 mL) was treated with p-TsOH (0.273 g, 1.44 mmol) and NaHSO$_3$ (0.158 g, 1.52 mmol) and heated at 100° C. for 16 h. The reaction mixture was cooled to room temperature and concentrated. The residue was purified by silica gel chromatography eluting with 0-50% CH$_2$Cl$_2$/92:7:1 CHCl$_3$/MeOH/concentrated NH$_4$OH in CH$_2$Cl$_2$. A portion of this material was further purified by reverse phase HPLC eluting with 10% to 90% CH$_3$CN in H$_2$O with 0.1% TFA. The product fractions were combined and concentrated. The residue was dissolved in water, acidified with 5 N HCl and concentrated to afford the title compound in hydrochloric acid salt form (0.042 g, 9%) as a brown solid: $^1$H NMR (300 MHz, CD$_3$OD) δ 7.88 (dd, J=7.4, 8.7 Hz, 1H), 7.66 (d, I=7.3 Hz, 1H), 7.27 (d, J=7.3 Hz, 1H), 7.03 (d, J=2.2 Hz, 1H), 6.82 (d, J=2.2 Hz, 1H), 4.01 (s, 3H), 4.01 (s, 3H), 3.85-4.00 (m, 1H), 3.75-3.83 (m, 4H), 3.52-3.62 (m, 4H), 1.17 (d, J=6.6 Hz, 6H); ESI MS m/z 453 [M+H]$^+$.

Example 28

Preparation of 2-(6-(4-Isopropyl-2-oxopiperazin-1-yl)pyridin-2-yl)-5,7-dimethoxyquinazolin-4(3H)-one Hydrochloride

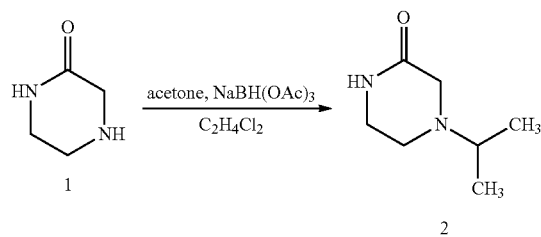

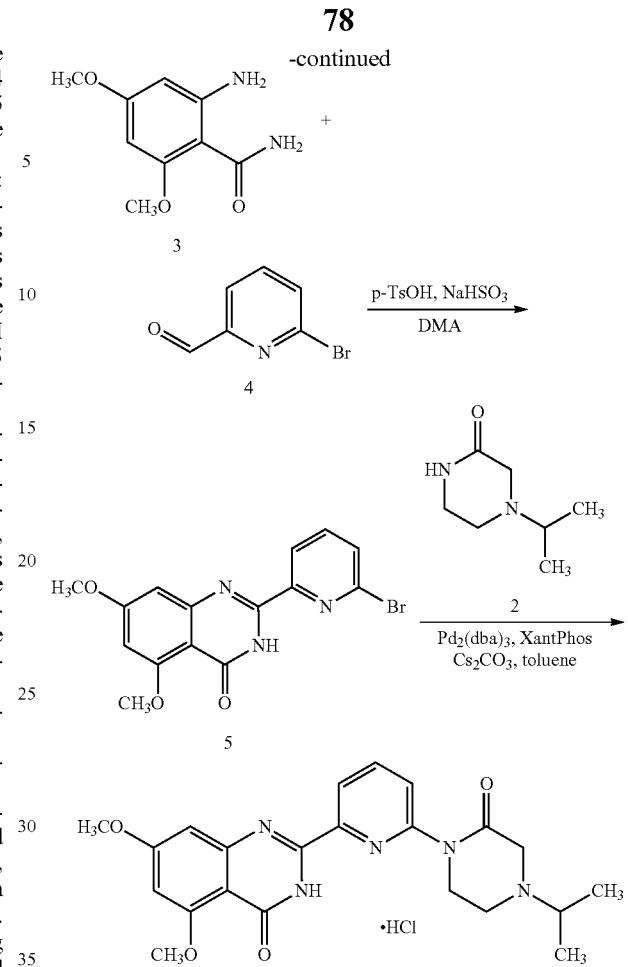

Example 28

Preparation of 4-isopropylpiperazin-2-one (2): To a solution of piperazin-2-one (1, 0.5 g, 5 mmol) and acetone (0.58 g, 10 mmol) in 1,2-dichloroethane (20 mL) was added sodium triacetoxyborohydride (3.18 g, 15.0 mmol) and the mixture was heated at 70° C. for 2 h. The mixture was diluted with EtOAc/saturated Na$_2$CO$_3$ (100/50 mL), washed with brine (20 mL), dried (Na$_2$SO$_4$), filtered and concentrated to afford the crude title compound (0.56 g, 79%).

Preparation of 2-(6-Bromopyridin-2-yl)-5,7-dimethoxyquinazolin-4(3H)-one (5): A solution of 6-bromopicolinaldehyde (4, 2.8 g, 15 mmol) and 2-amino-4,6-dimethoxybenzamide (3, 2.00 g, 10.2 mmol) in DMA (150 mL) was treated with p-TsOH (4.2 g, 22 mmol) and NaHSO$_3$ (2.6 g, 25 mmol) and then heated at 110° C. for 16 h. The reaction mixture was cooled to room temperature and concentrated. The residue was purified by silica gel chromatography eluting with 0-2% MeOH in CH$_2$Cl$_2$ to afford the title compound (1.87 g, 51%) as a yellow solid: $^1$H NMR (500 MHz, CDCl$_3$) δ 10.40 (s, 1H), 8.49 (d, J=7.5 Hz, 1H), 7.75 (t, J=7.5 Hz, 1H), 7.65 (d, J=7.5 Hz, 1H), 6.83 (d, J=2.2 Hz, 1H), 6.52 (d, J=2.2 Hz, 1H), 4.00 (s, 3H), 3.95 (s, 3H); Multimode MS m/z 362 [M+H]$^+$.

Preparation of 2-(6-(4-Isopropyl-2-oxopiperazin-1-yl)pyridin-2-yl)-5,7-dimethoxyquinazolin-4(3H)-one Hydrochloride (Example 28): To a mixture of 2-(6-bromopyridin-2-yl)-5,7-dimethoxyquinazolin-4(3H)-one (5, 0.320 g, 0.886 mmol), 4-isopropylpiperazin-2-one (2, 0.152 g, 1.07 mmol), cesium carbonate (0.572 g, 1.76 mmol) and XantPhos (0.024 g, 0.044 mmol) in toluene (100 mL) under nitrogen was added Pd$_2$(dba)$_3$ (0.040 g, 0.044 mmol) and the mixture heated at 110° C. for 48 h. The mixture was cooled to room temperature. The reaction mixture was loaded directly on a silica gel column and eluted with 0-2% MeOH in CH$_2$Cl$_2$. The material was further purified by reverse phase HPLC eluting with 10% to 90% CH$_3$CN in H$_2$O with 0.1% TFA. The product fractions were combined and concentrated. The residue was dissolved in water, acidified with 5 N HCl, and concentrated to afford the title compound (0.091 g, 22%) as a yellow solid: $^1$H NMR (500 MHz, DMSO-d$_6$) δ 11.38 (s, 1H), 8.25-8.32 (m, 1H), 8.10-8.18 (m, 2H), 6.83 (d, J=2.2 Hz, 1H), 6.62 (d, J=2.2 Hz, 1H), 4.89 (d, J=13.5 Hz, 1H), 4.35-4.22 (m, 1H), 4.22-4.10 (m, 1H), 4.10-4.00 (m, 1H), 3.95-3.80 (m, 1H), 3.60-3.72 (m, 1H), 3.55-3.60 (m, 1H), 3.92 (s, 3H), 3.88 (s, 3H), 1.37 (d, J=6.5 Hz, 6H); ESI MS m/z 424 [M+H]$^+$.

Example 29

Preparation of 2-(6-(4-(Dimethylamino)piperidin-1-yl)pyridin-2-yl)-5,7-dimethoxyquinazolin-4(3H)-one

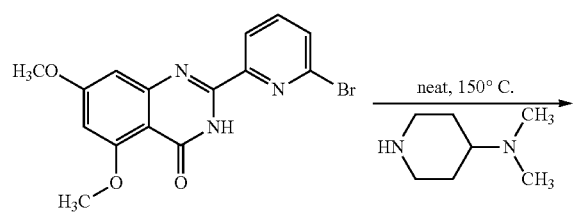

5

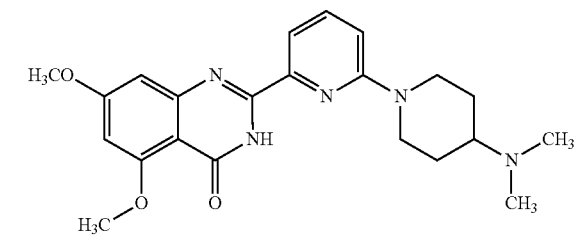

Example 29

Preparation of 2-(6-(4-(Dimethylamino)piperidin-1-yl)pyridin-2-yl)-5,7-dimethoxyquinazolin-4(3H)-one (Example 29): To a high pressure vial was added 2-(6-bromopyridin-2-yl)-5,7-dimethoxyquinazolin-4(3H)-one (5 Scheme 21, 100 mg, 0.27 mmol) and N,N-dimethylpiperidin-4-amine (142 mg, 1.10 mmol). The tube was sealed and the reaction was heated to 110° C. for 4 h. The product was purified by silica gel chromatography eluting with 0-5% CH$_2$Cl$_2$: CH$_3$OH:aq. NH$_4$OH (80/18/2) in CH$_2$Cl$_2$ to afford the title compound (0.815 g, 31%) as a yellow solid: $^1$H NMR (500 MHz, DMSO-d$_6$) δ 10.9 (s, 1H), 7.72 (t, J=8.0 Hz, 1H), 7.64 (d, J=7.0 Hz, 1H), 7.07 (d, J=8.5 Hz, 1H), 6.77 (d, J=2.0 Hz, 1H), 6.57 (d, J=2.0 Hz, 1H), 4.49-4.46 (m, 2H), 3.90 (s, 3H), 3.86 (s, 3H), 2.93-2.83 (m, 2H), 2.42-2.30 (m, 1H), 2.21 (s, 6H), 1.90-1.82 (m, 2H), 1.48-1.30 (m, 2H); ESI MS m/z 410 [M+H]$^+$.

Example 30

Preparation of 5,7-Dimethoxy-2-(6-(4-methyl-3-oxopiperazin-1-yl)pyridin-2-yl)quinazolin-4(3H)-one

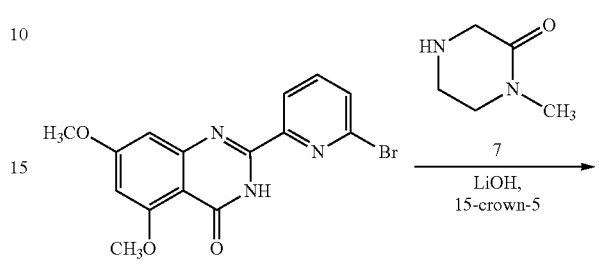

5

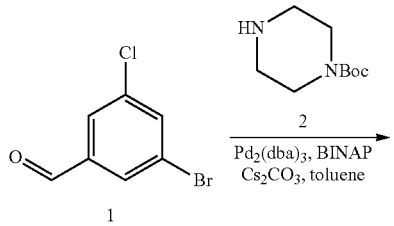

Example 30

Preparation of 5,7-Dimethoxy-2-(6-(4-methyl-3-oxopiperazin-1-yl)pyridin-2-yl)quinazolin-4(3H)-one (Example 30): A mixture of 2-(6-bromopyridin-2-yl)-5,7-dimethoxyquinazolin-4(3H)-one (5 Scheme 21, 0.100 g, 0.278 mmol), 1-methylpiperazin-2-one (7, 0.100 g, 0.667 mmol) and anhydrous lithium hydroxide (0.020 g, 0.83 mmol) in 15-crown-5 (0.9 mL) was heated at 100° C. for 18 h. The mixture was cooled to room temperature and purified by reverse phase HPLC eluting with 10% to 90% CH$_3$CN in H$_2$O to afford the title compound (0.02 g, 18%) as an off-white solid: $^1$H NMR (500 MHz, DMSO-d$_6$) δ 11.33 (s, 1H), 7.78 (t, J=7.5 Hz, 1H), 7.73 (d, J=7.1 Hz, 1H), 7.08 (d, J=8.3 Hz, 1H), 6.78 (d, J=2.2 Hz, 1H), 6.58 (d, J=2.2 Hz, 1H), 4.25 (s, 2H), 3.97 (t, J=5.5 Hz, 2H), 3.91 (s, 3H), 3.87 (s, 3H), 3.47 (t, J=5.3 Hz, 2H), 2.93 (s, 3H); ESI MS m/z 396 [M+H]$^+$.

Example 31

Preparation of 2-(3-Chloro-5-(piperazin-1-yl)phenyl)-5,7-dimethoxyquinazolin-4(3H)-one -continued

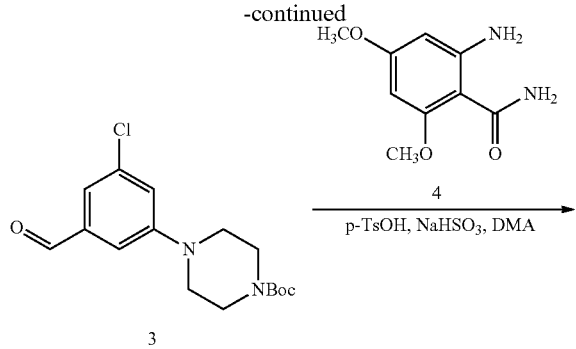

3

Example 32

Preparation of 2-(3-Chloro-5-(4-isopropylpiperazin-1-yl)phenyl)-5,7-dimethoxyquinazolin-4(3H)-one

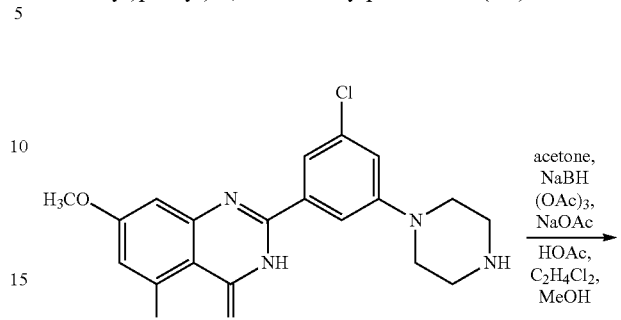

Example 31

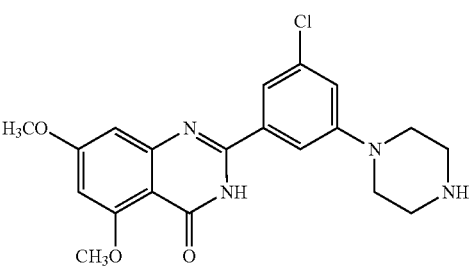

Example 31

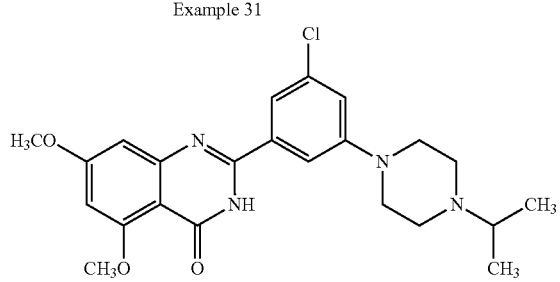

Example 32

Preparation of tert-Butyl 4-(3-Chloro-5-formylphenyl)piperazine-1-carboxylate (3): To a mixture of 3-bromo-5-chlorobenzaldehyde (1, 0.250 g, 1.14 mmol), tert-butyl piperazine-1-carboxylate (2, 0.255 g, 1.37 mmol), cesium carbonate (0.667 g, 2.05 mmol), and BINAP (0.106 g, 0.171 mmol) in toluene (100 mL) was added $Pd_2(dba)_3$ (0.104 g, 0.114 mmol). The reaction was placed under $N_2$ and heated at 110° C. for 16 h. The mixture was cooled to room temperature and was loaded directly on silica gel column and eluted with 0-50% EtOAc in hexanes to afford the crude title compound (0.3 g, 81%).

Preparation of 2-(3-Chloro-5-(piperazin-1-yl)phenyl)-5,7-dimethoxyquinazolin-4(3H)-one (Example 31): A solution of tert-butyl 4-(3-chloro-5-formylphenyl)piperazine-1-carboxylate (3, 0.300 g, 0.918 mmol) and 2-amino-4,6-dimethoxybenzamide (4, 0.120 g, 0.612 mmol) in DMA (4 mL) was treated with p-TsOH (0.424 g, 1.46 mmol) and $NaHSO_3$ (0.290 g, 1.84 mmol) and then heated at 110° C. for 16 h. The reaction mixture was cooled to room temperature, trifluoroacetic acid (5 mL) was added and the mixture was heated at 70° C. for 1 h. The reaction mixture was cooled to room temperature and concentrated. The residue was purified by silica gel chromatography eluting with 0-100% 92:7:1 $CHCl_3$/MeOH/concentrated $NH_4OH$ in $CH_2Cl_2$. This material was further purified by reverse phase HPLC eluting with 10% to 90% $CH_3CN$ in $H_2O$ with 0.1% TFA. The product fractions were concentrated and the residue was dissolved in acetonitrile and water. The mixture was basified with concentrated $NH_4OH$ and the precipitate filtered, washed with water, and dried under vacuum to afford the title compound (0.072 g, 29%) as an off-white solid: $^1H$ NMR (500 MHz, DMSO-$d_6$) δ 7.60-7.70 (m, 2H), 7.08-7.12 (m, 1H), 6.78 (d, J=2.3 Hz, 1H), 6.55 (d, J=2.3 Hz, 1H), 3.89 (s, 3H), 3.85 (s, 3H), 3.24 (t, J=5.2 Hz, 4H), 3.28 (t, J=5.2 Hz, 4H); ESI MS m/z 401 [M+H]$^+$.

To a solution of 2-(3-chloro-5-(piperazin-1-yl)phenyl)-5,7-dimethoxyquinazolin-4(3H)-one (Example 31, 0.054 g, 0.14 mmol), acetone (0.060 g, 1.4 mmol), sodium acetate (0.023 g, 0.27 mmol), and acetic acid (0.16 g, 2.7 mmol) in 1,2-dichloroethane/methanol (5/5 mL) was added sodium triacetoxyborohydride (0.56 g, 2.7 mmol). The mixture was stirred at room temperature for 16 h and then concentrated. The residue was purified by silica gel chromatography eluting with 0-100% 92:7:1 $CHCl_3$/MeOH/concentrated $NH_4OH$ in $CH_2Cl_2$. This material was further purified by reverse phase HPLC eluting with 10% to 90% $CH_3CN$ in $H_2O$ with 0.1% TFA. The product fractions were concentrated and the residue was dissolved in acetonitrile and water. The mixture was basified with concentrated $NH_4OH$ and concentrated. The residue was purified by reverse phase HPLC eluting with 10% to 90% $CH_3CN$ in $H_2O$ without TFA to afford the title compound (0.011 g, 18%) as an off-white solid: $^1H$ NMR (500 MHz, $CD_3OD$) δ 7.52 (s, 1H), 7.49 (d, J=1.5 Hz, 1H), 7.18 (t, J=1.5 Hz, 1H), 6.82 (d, J=2.5 Hz, 1H), 6.59 (d, J=2.5 Hz, 1H), 3.93 (s, 3H), 3.92 (s, 3H), 3.35-3.60 (br s, 4H), 2.85-3.15 (br s, 4H), 1.25-1.40 (br s, 1H), 1.23 (d, J=6.5 Hz, 6H); ESI MS m/z 443 [M+H]$^+$.

Example 33

Inhibition of Tetra-Acetylated Histone H4 Binding Individual BET Bromodomains

Proteins were cloned and overexpressed with a N-terminal 6×His tag, then purified by nickel affinity followed by size exclusion chromatography. Briefly, *E. coli* BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein is pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 and BET bromodomains was confirmed by a Time Resolved Fluorescence Resonance Energy Transfer (TR-FRET) method. N-terminally His-tagged bromodomains (200 nM) and biotinylated tetra-acetylated histone H4 peptide (25-50 nM, Millipore) were incubated in the presence of Europium Cryptate-labeled streptavidin (Cisbio Cat. #610SAKLB) and XL665-labeled monoclonal anti-His antibody (Cisbio Cat. #61HISXLB) in a white 96 well microtiter plate (Greiner). For inhibition assays, serially diluted test compound was added to these reactions in a 0.2% final concentration of DMSO. Final buffer concentrations were 30 mM HEPES pH 7.4, 30 mM NaCl, 0.3 mM CHAPS, 20 mM phosphate pH 7.0, 320 mM KF, 0.08% BSA). After 2 hours incubation at room temperature, the fluorescence by FRET was measured at 665 and 620 nm by a SynergyH4 plate reader (Biotek). Illustrative results with the first bromodomain of Brd4 are shown below. The binding inhibitory activity was shown by a decrease in 665 nm fluorescence relative to 620 nm. $IC_{50}$ values were determined from a dose response curve.

Compounds with an $IC_{50}$ value less than 30 μM were deemed to be active.

TABLE 1

Inhibition of Binding of Tetra-acetylated Histone H4 and Brd4 bromodomain 1 as Measured by FRET

| Name | FRET activity (IC50 < 30 μM) |
| --- | --- |
| 2-(3-(4-Isopropylpiperazin-1-yl)phenyl)-5,7-dimethoxyquinazolin-4(3H)-one [Example 1] | Active |
| 2-(3-(4-Isopropylpiperazin-1-yl)-5-methoxyphenyl)-5,7-dimethoxyquinazolin-4(3H)-one [Example 2] | Active |
| 5,7-Dimethoxy-2-(6-(4-(2-methoxyethyl)piperazin-1-yl)pyridin-2-yl)quinazolin-4(3H)-one [Example 3] | Active |
| 2-(6-(4-(2-Hydroxyethyl)piperazin-1-yl)pyridin-2-yl)-5,7-dimethoxyquinazolin-4(3H)-one [Example 4] | Active |
| 2-(6-(4-Isobutylpiperazin-1-yl)pyridin-2-yl)-5,7-dimethoxyquinazolin-4(3H)-one [Example 5] | Active |
| 5,7-Dimethoxy-2-(6-(4-(2-(methylsulfonyl)ethyl)piperazin-1-yl)pyridin-2-yl)quinazolin-4(3H)-one [Example 6] | Active |
| Methyl 2-(4-(6-(5,7-dimethoxy-4-oxo-3,4-dihydroquinazolin-2-yl)pyridin-2-yl)piperazin-1-yl)acetate [Example 7] | Active |
| 2-(6-(4-(1-Hydroxypropan-2-yl)piperazin-1-yl)pyridin-2-yl)-5,7-dimethoxyquinazolin-4(3H)-one [Example 8] | Active |
| 2-(4-(6-(5,7-Dimethoxy-4-oxo-3,4-dihydroquinazolin-2-yl)pyridin-2-yl)piperazin-1-yl)propanamide [Example 9] | Active |
| 2-(4-(6-(5,7-Dimethoxy-4-oxo-3,4-dihydroquinazolin-2-yl)pyridin-2-yl)piperazin-1-yl)acetic acid [Example 10] | Active |
| 3-(4-(6-(5,7-Dimethoxy-4-oxo-3,4-dihydroquinazolin-2-yl)pyridin-2-yl)piperazin-1-yl)propanoic acid [Example 11] | Active |
| 2-(5-(2-(Isopropylamino)ethoxy)-6-(4-isopropylpiperazin-1-yl)pyridin-2-yl)-5,7-dimethoxyquinazolin-4(3H)-one bis(trifluoroacetate) [Example 12] | Active |
| 2-(5-(2-Hydroxyethoxy)-6-(4-isopropylpiperazin-1-yl)pyridin-2-yl)-5,7-dimethoxyquinazolin-4(3H)-one acetate [Example 13] | Active |
| 2-(6-(4-Isopropylpiperazin-1-yl)-5-methoxypyridin-2-yl)-5,7-dimethoxyquinazolin-4(3H)-one [Example 14] | Active |
| 5,7-Dimethoxy-2-(6-(4-methylpiperazin-1-yl)pyridin-2-yl)quinazolin-4(3H)-one Hydrochloride (Example 15) | Active |
| 5,7-Dimethoxy-2-(6-morpholinopyridin-2-yl)quinazolin-4(3H)-one Hydrochloride (Example 16) | Active |
| 2-(6-(4-Isopropylpiperazin-1-yl)pyridin-2-yl)-5,7-dimethoxyquinazolin-4(3H)-one Hydrochloride (Example 17) | Active |
| 5,7-Dimethoxy-2-(6-(4-(methylsulfonyl)piperazin-1-yl)pyridin-2-yl)quinazolin-4(3H)-one Hydrochloride (Example 18) | Not Active |
| 5,7-Dimethoxy-2-(6-(4-propionylpiperazin-1-yl)pyridin-2-yl)quinazolin-4(3H)-one dihydrochloride (Example 19) | Active |
| 2-(3-(4-Isopropylpiperazin-1-yl)-5-(trifluoromethoxy)phenyl)-5,7-dimethoxyquinazolin-4(3H)-one (Example 20) | Active |
| 7-Fluoro-2-(6-(4-isopropylpiperazin-1-yl)pyridin-2-yl)-5-methoxyquinazolin-4(3H)-one Hydrochloride (Example 21) | Active |
| 7-(Benzyloxy)-2-(6-(4-isopropylpiperazin-1-yl)pyridin-2-yl)-5-methoxyquinazolin-4(3H)-one Hydrochloride (Example 22) | Active |
| 7-(4-Isopropylpiperazin-1-yl)-2-(6-(4-isopropylpiperazin-1-yl)pyridin-2-yl)-5-methoxyquinazolin-4(3H)-one Hydrochloride (Example 23) | Active |
| 2-(6-(4-Isopropylpiperazin-1-yl)pyridin-2-yl)-5-methoxy-7-phenylquinazolin-4(3H)-one (Example 25) | Active |
| 8-(Benzyloxy)-2-(3-(4-isopropylpiperazin-1-yl)phenyl)-5-methoxyquinazolin-4(3H)-one (Example 26) | Active |
| 4-(6-(5,7-Dimethoxy-4-oxo-3,4-dihydroquinazolin-2-yl)pyridin-2-yl)-N-isopropylpiperazine-1-carboxamide Hydrochloride (Example 27) | Active |
| 2-(6-(4-Isopropyl-2-oxopiperazin-1-yl)pyridin-2-yl)-5,7-dimethoxyquinazolin-4(3H)-one Hydrochloride (Example 28) | Not Active |
| 2-(6-(4-(Dimethylamino)piperidin-1-yl)pyridin-2-yl)-5,7-dimethoxyquinazolin-4(3H)-one (Example 29) | Active |

TABLE 1-continued

Inhibition of Binding of Tetra-acetylated Histone
H4 and Brd4 bromodomain 1 as Measured by FRET

| Name | FRET activity (IC50 < 30 μM) |
|---|---|
| 5,7-Dimethoxy-2-(6-(4-methyl-3-oxopiperazin-1-yl)pyridin-2-yl)quinazolin-4(3H)-one (Example 30) | Not Active |
| 2-(3-Chloro-5-(piperazin-1-yl)phenyl)-5,7-dimethoxyquinazolin-4(3H)-one (Example 31) | Active |
| 2-(3-Chloro-5-(4-isopropylpiperazin-1-yl)phenyl)-5,7-dimethoxyquinazolin-4(3H)-one (Example 32) | Active |

Example 34

Inhibition of c-Myc Expression in Cancer Cell Lines

MV4-11 cells ($2.5 \times 10^4$ cells) were plated in 96 well U-bottom plates with test compound or DMSO (0.1%), and incubated for 3 hours at 37° C. Cells were then harvested by centrifugation, lysed, and mRNA was isolated using the mRNA catcher plus kit (Invitrogen). Reverse transcription of the mRNA and duplex amplification of the c-myc and cyclophilin cDNAs was performed using the RNA Ultrasense kit (Invitrogen) and a ViiA7 real-time PCR machine (Applied Biosystems). $IC_{50}$ values were determined from a dose response curve.

Compounds with an $IC_{50}$ value less than 30 μM were deemed to be active.

TABLE 2

Inhibition of c-myc Activity in Human AML MV4-11 cells

| Name | c-myc activity (IC50 < 30 μM) |
|---|---|
| 2-(3-(4-Isopropylpiperazin-1-yl)phenyl)-5,7-dimethoxyquinazolin-4(3H)-one [Example 1] | Active |
| 2-(3-(4-Isopropylpiperazin-1-yl)-5-methoxyphenyl)-5,7-dimethoxyquinazolin-4(3H)-one [Example 2] | Active |
| 5,7-Dimethoxy-2-(6-(4-(2-methoxyethyl)piperazin-1-yl)pyridin-2-yl)quinazolin-4(3H)-one [Example 3] | Active |
| 2-(6-(4-(2-Hydroxyethyl)piperazin-1-yl)pyridin-2-yl)-5,7-dimethoxyquinazolin-4(3H)-one [Example 4] | Active |
| 2-(6-(4-Isobutylpiperazin-1-yl)pyridin-2-yl)-5,7-dimethoxyquinazolin-4(3H)-one [Example 5] | Active |
| 5,7-Dimethoxy-2-(6-(4-(2-(methylsulfonyl)ethyl)piperazin-1-yl)pyridin-2-yl)quinazolin-4(3H)-one [Example 6] | Not Active |
| 2-(6-(4-(1-Hydroxypropan-2-yl)piperazin-1-yl)pyridin-2-yl)-5,7-dimethoxyquinazolin-4(3H)-one [Example 8] | Active |
| 2-(4-(6-(5,7-Dimethoxy-4-oxo-3,4-dihydroquinazolin-2-yl)pyridin-2-yl)piperazin-1-yl)propanamide [Example 9] | Not Active |
| 2-(5-(2-(Isopropylamino)ethoxy)-6-(4-isopropylpiperazin-1-yl)pyridin-2-yl)-5,7-dimethoxyquinazolin-4(3H)-one bis(trifluoroacetate) [Example 12] | Active |
| 2-(5-(2-Hydroxyethoxy)-6-(4-isopropylpiperazin-1-yl)pyridin-2-yl)-5,7-dimethoxyquinazolin-4(3H)-one acetate [Example 13] | Active |
| 2-(6-(4-Isopropylpiperazin-1-yl)-5-methoxypyridin-2-yl)-5,7-dimethoxyquinazolin-4(3H)-one [Example 14] | Active |
| 5,7-Dimethoxy-2-(6-(4-methylpiperazin-1-yl)pyridin-2-yl)quinazolin-4(3H)-one Hydrochloride (Example 15) | Active |
| 5,7-Dimethoxy-2-(6-morpholinopyridin-2-yl)quinazolin-4(3H)-one Hydrochloride (Example 16) | Not Active |
| 2-(6-(4-Isopropylpiperazin-1-yl)pyridin-2-yl)-5,7-dimethoxyquinazolin-4(3H)-one Hydrochloride (Example 17) | Active |
| 5,7-Dimethoxy-2-(6-(4-propionylpiperazin-1-yl)pyridin-2-yl)quinazolin-4(3H)-one dihydrochloride (Example 19) | Not Active |
| 2-(3-(4-Isopropylpiperazin-1-yl)-5-(trifluoromethoxy)phenyl)-5,7-dimethoxyquinazolin-4(3H)-one (Example 20) | Not Active |
| 7-Fluoro-2-(6-(4-isopropylpiperazin-1-yl)pyridin-2-yl)-5-methoxyquinazolin-4(3H)-one Hydrochloride (Example 21) | Active |
| 7-(Benzyloxy)-2-(6-(4-isopropylpiperazin-1-yl)pyridin-2-yl)-5-methoxyquinazolin-4(3H)-one Hydrochloride (Example 22) | Active |
| 7-(4-Isopropylpiperazin-1-yl)-2-(6-(4-isopropylpiperazin-1-yl)pyridin-2-yl)-5-methoxyquinazolin-4(3H)-one Hydrochloride (Example 23) | Active |
| 8-(Benzyloxy)-2-(3-(4-isopropylpiperazin-1-yl)phenyl)-5-methoxyquinazolin-4(3H)-one (Example 26) | Not Active |
| 4-(6-(5,7-Dimethoxy-4-oxo-3,4-dihydroquinazolin-2-yl)pyridin-2-yl)-N-isopropylpiperazine-1-carboxamide Hydrochloride (Example 27) | Active |
| 2-(6-(4-(Dimethylamino)piperidin-1-yl)pyridin-2-yl)-5,7-dimethoxyquinazolin-4(3H)-one (Example 29) | Active |
| 5,7-Dimethoxy-2-(6-(4-methyl-3-oxopiperazin-1-yl)pyridin-2-yl)quinazolin-4(3H)-one (Example 30) | Not Active |

TABLE 2-continued

Inhibition of c-myc Activity in Human AML MV4-11 cells

| Name | c-myc activity (IC50 < 30 μM) |
|---|---|
| 2-(3-Chloro-5-(piperazin-1-yl)phenyl)-5,7-dimethoxyquinazolin-4(3H)-one (Example 31) | Active |
| 2-(3-Chloro-5-(4-isopropylpiperazin-1-yl)phenyl)-5,7-dimethoxyquinazolin-4(3H)-one (Example 32) | Active |

Example 35

Inhibition of Cell Proliferation in Cancer Cell Lines

MV4-11 cells: 96-well plates were seeded with $5\times10^4$ cells per well of exponentially growing human AML MV-4-11 (CRL-9591) cells and immediately treated with two-fold dilutions of test compounds, ranging from 30 μM to 0.2 μM. Triplicate wells were used for each concentration, as well as a media only and three DMSO control wells. The cells and compounds were incubated at 37° C., 5% $CO_2$ for 72 hours before adding 20 μL of the CellTiter Aqueous One Solution (Promega) to each well and incubating at 37° C., 5% $CO_2$ for an additional 3-4 hours. The absorbance was taken at 490 nm in a spectrophotometer and the percentage of proliferation relative to DMSO-treated cells was calculated after correction from the blank well. $IC_{50}$ were calculated using the GraphPad Prism software.

Compounds with an $IC_{50}$ value less than 30 μM are deemed to be active.

TABLE 3

Inhibition of Cell Proliferation in Human AML MV-4-11 cells

| Name | cell proliferation activity (IC50 < 30 μM) |
|---|---|
| 2-(3-(4-Isopropylpiperazin-1-yl)phenyl)-5,7-dimethoxyquinazolin-4(3H)-one [Example 1] | Not Active |
| 2-(3-(4-Isopropylpiperazin-1-yl)-5-methoxyphenyl)-5,7-dimethoxyquinazolin-4(3H)-one [Example 2] | Active |
| 5,7-Dimethoxy-2-(6-(4-(2-methoxyethyl)piperazin-1-yl)pyridin-2-yl)quinazolin-4(3H)-one [Example 3] | Active |
| 2-(6-(4-(2-Hydroxyethyl)piperazin-1-yl)pyridin-2-yl)-5,7-dimethoxyquinazolin-4(3H)-one [Example 4] | Active |
| 2-(6-(4-Isobutylpiperazin-1-yl)pyridin-2-yl)-5,7-dimethoxyquinazolin-4(3H)-one [Example 5] | Active |
| 5,7-Dimethoxy-2-(6-(4-(2-(methylsulfonyl)ethyl)piperazin-1-yl)pyridin-2-yl)quinazolin-4(3H)-one [Example 6] | Not Active |
| 2-(6-(4-(1-Hydroxypropan-2-yl)piperazin-1-yl)pyridin-2-yl)-5,7-dimethoxyquinazolin-4(3H)-one [Example 8] | Active |
| 2-(4-(6-(5,7-Dimethoxy-4-oxo-3,4-dihydroquinazolin-2-yl)pyridin-2-yl)piperazin-1-yl)propanamide [Example 9] | Active |
| 2-(5-(2-(Isopropylamino)ethoxy)-6-(4-isopropylpiperazin-1-yl)pyridin-2-yl)-5,7-dimethoxyquinazolin-4(3H)-one bis(trifluoroacetate) [Example 12] | Active |
| 2-(5-(2-Hydroxyethoxy)-6-(4-isopropylpiperazin-1-yl)pyridin-2-yl)-5,7-dimethoxyquinazolin-4(3H)-one acetate [Example 13] | Not Active |
| 2-(6-(4-Isopropylpiperazin-1-yl)-5-methoxypyridin-2-yl)-5,7-dimethoxyquinazolin-4(3H)-one [Example 14] | Active |
| 5,7-Dimethoxy-2-(6-(4-methylpiperazin-1-yl)pyridin-2-yl)quinazolin-4(3H)-one Hydrochloride (Example 15) | Active |
| 5,7-Dimethoxy-2-(6-morpholinopyridin-2-yl)quinazolin-4(3H)-one Hydrochloride (Example 16) | Not Active |
| 2-(6-(4-Isopropylpiperazin-1-yl)pyridin-2-yl)-5,7-dimethoxyquinazolin-4(3H)-one Hydrochloride (Example 17) | Active |
| 5,7-Dimethoxy-2-(6-(4-propionylpiperazin-1-yl)pyridin-2-yl)quinazolin-4(3H)-one dihydrochloride (Example 19) | Not Active |
| 2-(3-(4-Isopropylpiperazin-1-yl)-5-(trifluoromethoxy)phenyl)-5,7-dimethoxyquinazolin-4(3H)-one (Example 20) | Not Active |
| 7-Fluoro-2-(6-(4-isopropylpiperazin-1-yl)pyridin-2-yl)-5-methoxyquinazolin-4(3H)-one Hydrochloride (Example 21) | Active |
| 7-(Benzyloxy)-2-(6-(4-isopropylpiperazin-1-yl)pyridin-2-yl)-5-methoxyquinazolin-4(3H)-one Hydrochloride (Example 22) | Active |
| 7-(4-isopropylpiperazin-1-yl)-2-(6-(4-isopropylpiperazin-1-yl)pyridin-2-yl)-5-methoxyquinazolin-4(3H)-one Hydrochloride (Example 23) | Active |
| 8-(Benzyloxy)-2-(3-(4-isopropylpiperazin-1-yl)phenyl)-5-methoxyquinazolin-4(3H)-one (Example 26) | Not Active |
| 4-(6-(5,7-Dimethoxy-4-oxo-3,4-dihydroquinazolin-2-yl)pyridin-2-yl)-N-isopropylpiperazine-1-carboxamide Hydrochloride (Example 27) | Active |
| 2-(6-(4-(Dimethylamino)piperidin-1-yl)pyridin-2-yl)-5,7-dimethoxyquinazolin-4(3H)-one (Example 29) | Active |
| 5,7-Dimethoxy-2-(6-(4-methyl-3-oxopiperazin-1-yl)pyridin-2-yl)quinazolin-4(3H)-one (Example 30) | Not Active |

TABLE 3-continued

Inhibition of Cell Proliferation in Human AML MV-4-11 cells

| Name | cell proliferation activity (IC50 < 30 µM) |
|---|---|
| 2-(3-Chloro-5-(piperazin-1-yl)phenyl)-5,7-dimethoxyquinazolin-4(3H)-one (Example 31) | Active |
| 2-(3-Chloro-5-(4-isopropylpiperazin-1-yl)phenyl)-5,7-dimethoxyquinazolin-4(3H)-one (Example 32) | Active |

Example 36

Inhibition of hIL-6 mRNA Transcription

In this example, hIL-6 mRNA in tissue culture cells was quantitated to measure the transcriptional inhibition of hIL-6 when treated with a compound of the present disclosure.

A human leukemic monocyte lymphoma cell line (U937) was plated ($3.2 \times 10^4$ cells per well) in a 96-well plate in 100 IL RPMI-1640 containing 10% FBS and penicillin/streptomycin, and differentiated into macrophages for 3 days in 60 ng/mL PMA (phorbol-13-myristate-12-acetate) at 37° C. in 5% $CO_2$ prior to the addition of the compound of interest. The cells were pretreated for 1 h with the test compound prior to stimulation with 1 ug/mL lipopolysaccharide from *Escherichia coli*. The cells were incubated at 37-C for 3 h before the cells were harvested. At time of harvest, the spent media was removed from the cells and the cells were rinsed in 200 µL PBS. Cell lysis solution (70 µL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 µL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hIL-6 to an internal control, prior to determining the fold induction of each unknown sample, relative to the control.

Compounds with an $IC_{50}$ value less than 30 µM are deemed to be active.

TABLE 4

Inhibition of hIL-6 mRNA Transcription

| Name | IL-6 activity (IC50 < 30 µM) |
|---|---|
| 2-(3-(4-Isopropylpiperazin-1-yl)phenyl)-5,7-dimethoxyquinazolin-4(3H)-one [Example 1] | Active |
| 2-(3-(4-Isopropylpiperazin-1-yl)-5-methoxyphenyl)-5,7-dimethoxyquinazolin-4(3H)-one [Example 2] | Active |
| 5,7-Dimethoxy-2-(6-(4-(2-methoxyethyl)piperazin-1-yl)pyridin-2-yl)quinazolin-4(3H)-one [Example 3] | Active |
| 2-(6-(4-(2-Hydroxyethyl)piperazin-1-yl)pyridin-2-yl)-5,7-dimethoxyquinazolin-4(3H)-one [Example 4] | Active |
| 2-(6-(4-Isobutylpiperazin-1-yl)pyridin-2-yl)-5,7-dimethoxyquinazolin-4(3H)-one [Example 5] | Active |
| 5,7-Dimethoxy-2-(6-(4-(2-(methylsulfonyl)ethyl)piperazin-1-yl)pyridin-2-yl)quinazolin-4(3H)-one [Example 6] | Active |
| Methyl 2-(4-(6-(5,7-dimethoxy-4-oxo-3,4-dihydroquinazolin-2-yl)pyridin-2-yl)piperazin-1-yl)acetate [Example 7] | Active |
| 2-(6-(4-(1-Hydroxypropan-2-yl)piperazin-1-yl)pyridin-2-yl)-5,7-dimethoxyquinazolin-4(3H)-one [Example 8] | Active |
| 2-(4-(6-(5,7-Dimethoxy-4-oxo-3,4-dihydroquinazolin-2-yl)pyridin-2-yl)piperazin-1-yl)propanamide [Example 9] | Not Active |
| 2-(4-(6-(5,7-Dimethoxy-4-oxo-3,4-dihydroquinazolin-2-yl)pyridin-2-yl)piperazin-1-yl)acetic acid [Example 10] | Not Active |
| 3-(4-(6-(5,7-Dimethoxy-4-oxo-3,4-dihydroquinazolin-2-yl)pyridin-2-yl)piperazin-1-yl)propanoic acid [Example 11] | Not Active |
| 2-(5-(2-(Isopropylamino)ethoxy)-6-(4-isopropylpiperazin-1-yl)pyridin-2-yl)-5,7-dimethoxyquinazolin-4(3H)-one bis(trifluoroacetate) [Example 12] | Not Active |
| 2-(5-(2-Hydroxyethoxy)-6-(4-isopropylpiperazin-1-yl)pyridin-2-yl)-5,7-dimethoxyquinazolin-4(3H)-one acetate [Example 13] | Active |
| 2-(6-(4-Isopropylpiperazin-1-yl)-5-methoxypyridin-2-yl)-5,7-dimethoxyquinazolin-4(3H)-one [Example 14] | Not Active |
| 5,7-Dimethoxy-2-(6-(4-methylpiperazin-1-yl)pyridin-2-yl)quinazolin-4(3H)-one Hydrochloride (Example 15) | Active |
| 5,7-Dimethoxy-2-(6-morpholinopyridin-2-yl)quinazolin-4(3H)-one Hydrochloride (Example 16) | Active |
| 2-(6-(4-Isopropylpiperazin-1-yl)pyridin-2-yl)-5,7-dimethoxyquinazolin-4(3H)-one Hydrochloride (Example 17) | Active |

TABLE 4-continued

Inhibition of hIL-6 mRNA Transcription

| Name | IL-6 activity (IC50 < 30 µM) |
| --- | --- |
| 5,7-Dimethoxy-2-(6-(4-(methylsulfonyl)piperazin-1-yl)pyridin-2-yl)quinazolin-4(3H)-one Hydrochloride (Example 18) | Not Active |
| 5,7-Dimethoxy-2-(6-(4-propionylpiperazin-1-yl)pyridin-2-yl)quinazolin-4(3H)-one dihydrochloride (Example 19) | Not Active |
| 2-(3-(4-Isopropylpiperazin-1-yl)-5-(trifluoromethoxy)phenyl)-5,7-dimethoxyquinazolin-4(3H)-one (Example 20) | Active |
| 7-Fluoro-2-(6-(4-isopropylpiperazin-1-yl)pyridin-2-yl)-5-methoxyquinazolin-4(3H)-one Hydrochloride (Example 21) | Active |
| 7-(Benzyloxy)-2-(6-(4-isopropylpiperazin-1-yl)pyridin-2-yl)-5-methoxyquinazolin-4(3H)-one Hydrochloride (Example 22) | Active |
| 7-(4-Isopropylpiperazin-1-yl)-2-(6-(4-isopropylpiperazin-1-yl)pyridin-2-yl)-5-methoxyquinazolin-4(3H)-one Hydrochloride (Example 23) | Not Active |
| 2-(6-(4-Isopropylpiperazin-1-yl)pyridin-2-yl)-5-methoxy-7-phenylquinazolin-4(3H)-one (Example 25) | Not Active |
| 8-(Benzyloxy)-2-(3-(4-isopropylpiperazin-1-yl)phenyl)-5-methoxyquinazolin-4(3H)-one (Example 26) | Not Active |
| 4-(6-(5,7-Dimethoxy-4-oxo-3,4-dihydroquinazolin-2-yl)pyridin-2-yl)-N-isopropylpiperazine-1-carboxamide Hydrochloride (Example 27) | Active |
| 2-(6-(4-(Dimethylamino)piperidin-1-yl)pyridin-2-yl)-5,7-dimethoxyquinazolin-4(3H)-one (Example 29) | Active |
| 5,7-Dimethoxy-2-(6-(4-methyl-3-oxopiperazin-1-yl)pyridin-2-yl)quinazolin-4(3H)-one (Example 30) | Active |
| 2-(3-Chloro-5-(piperazin-1-yl)phenyl)-5,7-dimethoxyquinazolin-4(3H)-one (Example 31) | Active |
| 2-(3-Chloro-5-(4-isopropylpiperazin-1-yl)phenyl)-5,7-dimethoxyquinazolin-4(3H)-one (Example 32) | Active |

Example 37

Inhibition of hVCAM mRNA Transcription

In this example, hVCAM mRNA in tissue culture cells is quantitated to measure the transcriptional inhibition of hVCAM when treated with a compound of the present disclosure.

Human umbilical vein endothelial cells (HUVECs) are plated in a 96-well plate ($4.0 \times 10^3$ cells/well) in 100 µL EGM media and incubated for 24 h prior to the addition of the compound of interest. The cells are pretreated for 1 h with the test compound prior to stimulation with tumor necrosis factor-α. The cells are incubated for an additional 24 h before the cells are harvested. At time of harvest, the spent media is removed from the HUVECs and rinsed in 200 µL PBS. Cell lysis solution (70 µL) is then added the cells in each well and incubated for [18] 5-10 min at room temperature, to allow for complete cell lysis and detachment, mRNA is then prepared using the "mRNA Catcher PLUS plate" (Invitrogen), according to the protocol supplied. After the last wash, as much wash buffer as possible is aspirated without allowing the wells to dry. Elution buffer (E3, 70 µL) is then added to each well. mRNA is then eluted by incubating the mRNA Catcher PLUS plate with elution buffer for 5 min at 68° C. and then immediately placing the plate on ice.

The eluted mRNA so isolated is then used in a one-step quantitative real-time PCR reaction, using components of the Ultra Sense Kit together with Applied Biosystems primer-probe mixes. Real-time PCR data was analyzed, normalizing the Ct values for hVCAM to an internal control, prior to determining the fold induction of each unknown sample, relative to the control.

Compounds with an $IC_{50}$ value less than 30 µM are deemed to be active.

Example 38

Inhibition of hMCP-1 mRNA Transcription

In this example, hMCP-1 mRNA in human peripheral blood mononuclear cells was quantitated to measure the transcriptional inhibition of hMCP-1 when treated with a compound of the present disclosure.

Human Peripheral Blood Mononuclear Cells were plated ($1.0 \times 10^5$ cells per well) in a 96-well plate in 45 µL RPMI-1640 containing 10% FBS and penicillin/streptomycin. The cells were treated with the test compound (45 µL at 2× concentration), and then the cells were incubated at 37° C. for 3 h before the cells were harvested. At time of harvest, cells were transferred to V-bottom plates and centrifuged at 800 rpm for 5 minutes. Spent media was removed and cell lysis solution (70 µL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 µL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hMCP-1 to an internal control, prior to determining the fold induction of each unknown sample, relative to the control.

Compounds with an $IC_{50}$ value less than 30 µM are deemed to be active.

TABLE 5

Inhibition of hMCP-1 mRNA Transcription

| Name | MCP-1 activity (IC50 < 30 µM) |
|---|---|
| 2-(6-(4-Isopropylpiperazin-1-yl)pyridin-2-yl)-5,7-dimethoxyquinazolin-4(3H)-one Hydrochloride (Example 17) | Active |

Example 39

Up-Regulation of hApoA-1 mRNA Transcription

In this example, ApoA-I mRNA in tissue culture cells was quantitated to measure the transcriptional up-regulation of ApoA-I when treated with a compound of the present disclosure.

Huh7 cells ($2.5 \times 10^5$ per well) were plated in a 96-well plate using 100 µL DMEM per well, (Gibco DMEM supplemented with penicillin/streptomycin and 10% FBS), 24 h before the addition of the compound of interest. After 48 hrs treatment, the spent media was removed from the Huh-7 cells and placed on ice (for immediate use) or at −80° C. (for future use) with the "LDH cytotoxicity assay Kit II" from Abcam. The cells remaining in the plate were rinsed with 100 µL PBS.

Then 85 µL of cell lysis solution was added to each well and incubated for 5-10 minutes at room temperature, to allow for complete cell lysis and detachment. mRNA was then prepared using the "mRNA Catcher PLUS plate" from Life Technologies, according to the protocol supplied. After the last wash, as much wash buffer as possible was aspirated without allowing the wells to dry. Elution Buffer (E3, 80 µL) was then added to each well. mRNA was then eluted by incubating the mRNA Catcher PLUS plate with Elution Buffer for 5 minutes at 68° C., and then 1 minute at 4° C. Catcher plates with mRNA eluted were kept on ice for use or stored at −80° C.

The eluted mRNA isolated was then used in a one-step real-time PCR reaction, using components of the Ultra Sense Kit together with Life Technologies primer-probe mixes. Real-time PCR data was analyzed, using the Ct values, to determine the fold induction of each unknown sample, relative to the control (that is, relative to the control for each independent DMSO concentration).

Compounds with an $EC_{170}$ value less than 30 µM are deemed to be active.

TABLE 6

Up-regulation of hApoA-1 mRNA Transcription.

| Name | ApoA-1 activity ($EC_{170}$ < 30 µM) |
|---|---|
| 2-(3-(4-Isopropylpiperazin-1-yl)phenyl)-5,7-dimethoxyquinazolin-4(3H)-one [Example 1] | Active |
| 2-(3-(4-Isopropylpiperazin-1-yl)-5-methoxyphenyl)-5,7-dimethoxyquinazolin-4(3H)-one [Example 2] | Active |
| 5,7-Dimethoxy-2-(6-(4-(2-methoxyethyl)piperazin-1-yl)pyridin-2-yl)quinazolin-4(3H)-one [Example 3] | Active |
| 2-(6-(4-(2-Hydroxyethyl)piperazin-1-yl)pyridin-2-yl)-5,7-dimethoxyquinazolin-4(3H)-one [Example 4] | Active |
| 2-(6-(4-Isobutylpiperazin-1-yl)pyridin-2-yl)-5,7-dimethoxyquinazolin-4(3H)-one [Example 5] | Active |
| 5,7-Dimethoxy-2-(6-(4-(2-(methylsulfonyl)ethyl)piperazin-1-yl)pyridin-2-yl)quinazolin-4(3H)-one [Example 6] | Active |
| 2-(6-(4-(1-Hydroxypropan-2-yl)piperazin-1-yl)pyridin-2-yl)-5,7-dimethoxyquinazolin-4(3H)-one [Example 8] | Active |
| 2-(4-(6-(5,7-Dimethoxy-4-oxo-3,4-dihydroquinazolin-2-yl)pyridin-2-yl)piperazin-1-yl)propanamide [Example 9] | Active |
| 3-(4-(6-(5,7-Dimethoxy-4-oxo-3,4-dihydroquinazolin-2-yl)pyridin-2-yl)piperazin-1-yl)propanoic acid [Example 11] | Not Active |
| 2-(5-(2-(Isopropylamino)ethoxy)-6-(4-isopropylpiperazin-1-yl)pyridin-2-yl)-5,7-dimethoxyquinazolin-4(3H)-one bis(trifluoroacetate) [Example 12] | Active |
| 2-(5-(2-Hydroxyethoxy)-6-(4-isopropylpiperazin-1-yl)pyridin-2-yl)-5,7-dimethoxyquinazolin-4(3H)-one acetate [Example 13] | Active |
| 2-(6-(4-Isopropylpiperazin-1-yl)-5-methoxypyridin-2-yl)-5,7-dimethoxyquinazolin-4(3H)-one [Example 14] | Active |
| 5,7-Dimethoxy-2-(6-(4-methylpiperazin-1-yl)pyridin-2-yl)quinazolin-4(3H)-one Hydrochloride (Example 15) | Active |
| 2-(6-(4-Isopropylpiperazin-1-yl)pyridin-2-yl)-5,7-dimethoxyquinazolin-4(3H)-one Hydrochloride (Example 17) | Active |
| 5,7-Dimethoxy-2-(6-(4-propionylpiperazin-1-yl)pyridin-2-yl)quinazolin-4(3H)-one dihydrochloride (Example 19) | Active |
| 2-(6-(4-Isopropyl-2-oxopiperazin-1-yl)pyridin-2-yl)-5,7-dimethoxyquinazolin-4(3H)-one Hydrochloride (Example 28) | Not Active |
| 2-(6-(4-(Dimethylamino)piperidin-1-yl)pyridin-2-yl)-5,7-dimethoxyquinazolin-4(3H)-one (Example 29) | Active |
| 2-(3-Chloro-5-(piperazin-1-yl)phenyl)-5,7-dimethoxyquinazolin-4(3H)-one (Example 31) | Active |
| 2-(3-Chloro-5-(4-isopropylpiperazin-1-yl)phenyl)-5,7-dimethoxyquinazolin-4(3H)-one (Example 32) | Active |

Examples 40

In Vivo Efficacy in Athymic Nude Mouse Strain of an Acute Myeloid Leukemia Xenograft Model Using MV4-11 Cells MV4-11 cells (ATCC) were grown under standard cell culture conditions and (NCr) nu/nu fisol strain of female mice age 6-7 weeks were injected $5e^6$ cells/animal in 100 µl PBS+ 100 µl Matrigel in lower left abdominal flank. Approximately by day 18 after MV4-11 cells injection, mice were randomized based on tumor volume (L×W×H)/2) of average ~120 mm$^3$. Mice were dosed orally with compound at 75 mg/kg b.i.d and 120 mg/kg b.i.d in EA006 formulation at 10 mL/kg body weight dose volume. Tumor measurements were taken with electronic micro caliper and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using student's t-test in Excel.

TABLE 7

In vivo efficacy in athymic nude mouse strain of an acute myeloid leukemia xenograft model using MV4-11 cells:

| Name | In vivo activity |
|---|---|
| 2-(6-(4-Isopropylpiperazin-1-yl)pyridin-2-yl)-5,7-dimethoxyquinazolin-4(3H)-one Hydrochloride (Example 17) | Active |

Example 41

In Vivo Efficacy in Mouse Endotoxemia Model Assay

Sub lethal doses of Endotoxin (*E. Coli* bacterial lipopolysaccharide) were administered to animals to produce a generalized inflammatory response which was monitored by increases in secreted cytokines. Compounds were administered to C57/Bl6 mice orally at 75 mg/kg dose to evaluate inhibition in IL-6 and IL-17 cytokines post 4 hour challenge with Lipopolysaccharide (LPS) at 0.5 mg/kg dose intraperitoneally.

TABLE 8

In Vivo Efficacy in Mouse Endotoxemia Model Assay.

| Name | In vivo activity |
|---|---|
| 2-(6-(4-Isopropylpiperazin-1-yl)pyridin-2-yl)-5,7-dimethoxyquinazolin-4(3H)-one Hydrochloride (Example 17) | Active |

Example 42

In Vivo Efficacy in Rat Collagen Induced Arthritis

Rat collagen-induced arthritis is an experimental model of polyarthritis that has been widely used for preclinical testing of numerous anti-arthritic agents. Following administration of collagen, this model establishes a measurable polyarticular inflammation, marked cartilage destruction in association with pannus formation and mild to moderate bone resorption and periosteal bone proliferation. In this model, collagen was administered to female Lewis strain of rats on Day 1 and 7 of study and dosed with compounds from Day 11 to Day 17. Test compounds were evaluated to assess the potential to inhibit the inflammation (including paw swelling), cartilage destruction and bone resorption in arthritic rats, using a model in which the treatment is administered after the disease has been established.

TABLE 9

In Vivo Efficacy in Rat Collagen Induced Arthritis.

| Name | In vivo activity |
|---|---|
| 2-(6-(4-Isopropylpiperazin-1-yl)pyridin-2-yl)-5,7-dimethoxyquinazolin-4(3H)-one Hydrochloride (Example 17) | Active |

Example 43

In Vivo Efficacy in Experimental Autoimmune Encephalomyelitis (EAE) Model of MS Experimental autoimmune encephalomyelitis (EAE) is a T-cell-mediated autoimmune disease of the CNS which shares many clinical and histopathological features with human multiple sclerosis (MS). EAE is the most commonly used animal model of MS. T cells of both Th1 and Th17 lineage have been shown to induce EAE. Cytokines IL-23, IL-6 and IL-17, which are either critical for Th1 and Th17 differentiation or produced by these T cells, play a critical and non-redundant role in EAE development. Therefore, drugs targeting production of these cytokines are likely to have therapeutic potential in treatment of MS.

This study was conducted to assess the potential anti-inflammatory effect of test compounds to inhibit the inflammation and clinical EAE scores of a 28 day preventative mouse model. In this model, EAE was induced by $MOG_{35-55}$/CFA immunization and pertussis toxin injection in female C57Bl/6 mice.

TABLE 10

In Vivo Efficacy in Experimental autoimmune encephalomyelitis (EAE) Model of MS

| Name | In vivo activity |
|---|---|
| 2-(6-(4-Isopropylpiperazin-1-yl)pyridin-2-yl)-5,7-dimethoxyquinazolin-4(3H)-one Hydrochloride (Example 17) | Active |

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A method of inhibiting BET proteins in a mammal by administering a therapeutically effective amount of a compound of Formula I:

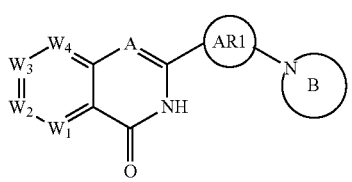

Formula I or a stereoisomer, tautomer, pharmaceutical acceptable salt, or hydrate thereof, wherein:
- $W_1$ is selected from N and $CR_1$;
- $W_2$ is selected from N and $CR_2$;
- $W_3$ is selected from N and $CR_3$;
- $W_4$ is selected from N and $CR_4$;
- each W may be the same or different from each other;
- A is selected from N and CH;
- $R_1$ and $R_4$ are each independently selected from hydrogen, alkyl, alkenyl, alkynyl, alkoxy, thioalkyl, aryloxy, aryl, amino, hydroxyl, and halogen;
- $R_2$ and $R_3$ are each independently selected from hydrogen, alkyl, alkenyl, alkynyl, alkoxy, thioalkyl, aryloxy, aryl, hydroxyl, and halogen;
- two adjacent substituents selected from $R_1$, $R_2$, $R_3$, and $R_4$ may be connected in a 5- or 6-membered ring to form a bicyclic carbocycle or bicyclic heterocycle;
- AR1 is a group selected from the following:

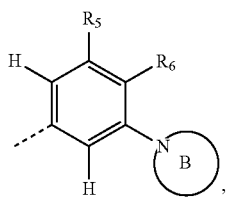
(i)

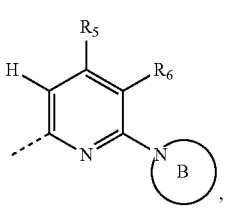
(ii)

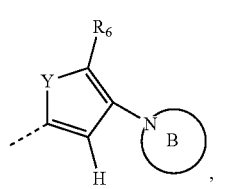
(iii)

and

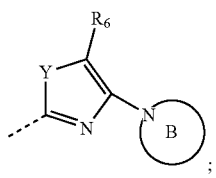
(iv)

B is a group selected from the following:

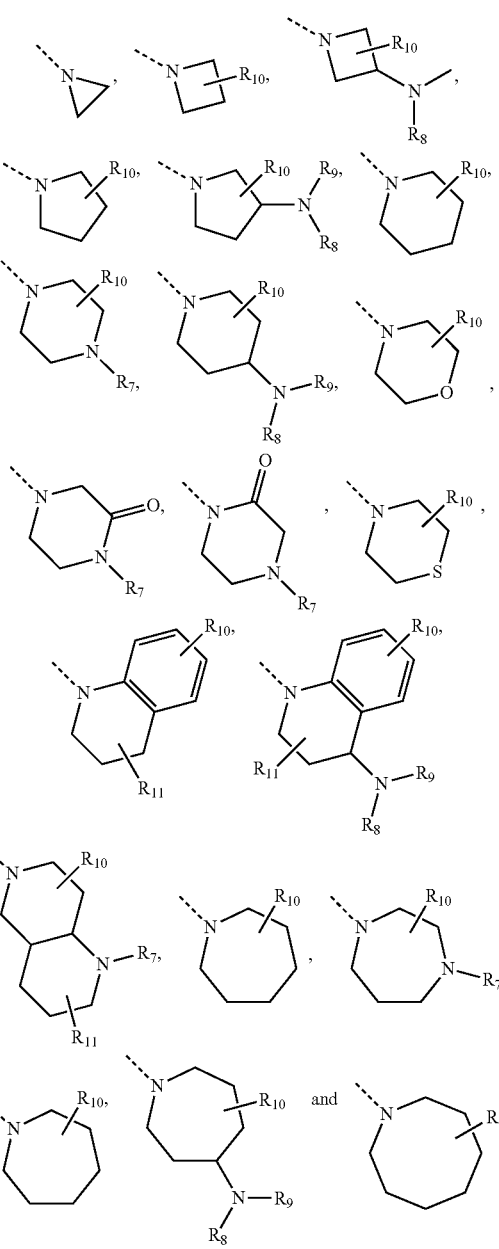

each ring system may be substituted with one or more substituents independently selected from $R_{10}$ and $R_{11}$:

$R_5$ is selected from hydrogen, alkoxy, alkyl, thioalkyl, aryloxy, aryl, hydroxyl, and halogen;

$R_6$ is selected from hydrogen, alkoxy, alkyl, thioalkyl, aryloxy, aryl, and halogen;

$R_7$ is selected from hydrogen, alkyl, —$SO_2R_{12}$, —$C(O)NR_{12}R_{13}$, and —$C(O)R_{12}$;

$R_8$ and $R_9$ are independently selected from hydrogen, aryl, alkenyl, alkyl, —$SO_2R_{12}$, —$C(O)NR_{12}R_{13}$, and —$C(O)R_{12}$;

$R_{10}$ and $R_{11}$ are independently selected from hydrogen, halogen, alkyl, alkoxy, aryl, and hydroxyl;

$R_{12}$ and $R_{13}$ are independently selected from hydrogen, aryl, and alkyl;

Y is selected from NH, O, and S; and two adjacent substituents selected from $R_5$, $R_6$, $R_8$, $R_9$, $R_{10}$, and $R_{11}$ may be connected in a 5- or 6-membered ring to form a carbocycle or heterocycle.

2. The method according to claim 1, wherein $R_1$ and $R_4$ are independently selected from hydrogen, alkyl, alkoxy, halogen, and amino;

wherein $R_2$ and $R_3$ are independently selected from hydrogen, alkyl, alkoxy, and halogen;

wherein at least one of $R_1$, $R_2$, $R_3$, and $R_4$ is not hydrogen;

wherein $R_5$ is selected from hydrogen, alkyl, alkoxy, and halogen;

wherein $R_6$ is selected from hydrogen and alkoxy optionally substituted with a hydroxyl or amino; and wherein Y is N.

3. The compound according to claim 2, wherein AR1 is selected from

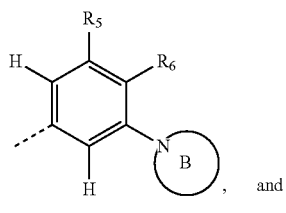, and

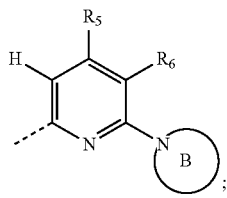;

wherein B is selected from

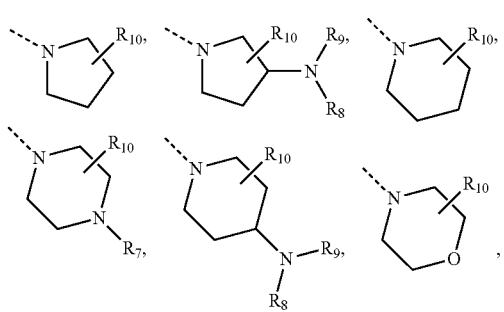

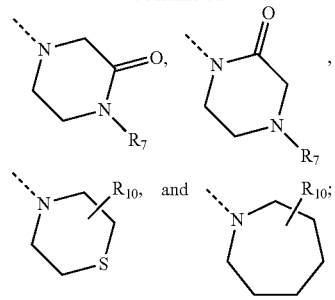

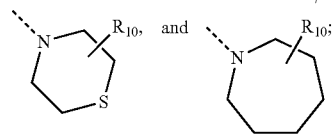

wherein $R_7$ is selected from hydrogen and alkyl;

wherein $R_8$ and $R_9$ are independently selected from hydrogen and alkyl;

wherein $R_{10}$ and $R_{11}$ are independently selected from hydrogen and halogen; and wherein $R_{12}$ and $R_{13}$ are independently selected from hydrogen and alkyl.

4. The method according to claim 1, wherein the compound is selected from:

2-(3-(4-Isopropylpiperazin-1-yl)phenyl)-5,7-dimethoxyquinazolin-4(3H)-one;

2-(3-(4-Isopropylpiperazin-1-yl)-5-methoxyphenyl)-5,7-dimethoxyquinazolin-4(3H)-one;

5,7-Dimethoxy-2-(6-(4-(2-methoxyethyl)piperazin-1-yl)pyridin-2-yl)quinazolin-4(3H)-one;

2-(6-(4-(2-Hydroxyethyl)piperazin-1-yl)pyridin-2-yl)-5,7-dimethoxyquinazolin-4(3H)-one;

2-(6-(4-Isobutylpiperazin-1-yl)pyridin-2-yl)-5,7-dimethoxyquinazolin-4(3H)-one;

5,7-Dimethoxy-2-(6-(4-(2-(methylsulfonyl)ethyl)piperazin-1-yl)pyridin-2-yl)quinazolin-4(3H)-one;

Methyl 2-(4-(6-(5,7-dimethoxy-4-oxo-3,4-dihydroquinazolin-2-yl)pyridin-2-yl)piperazin-1-yl)acetate;

2-(6-(4-(1-Hydroxypropan-2-yl)piperazin-1-yl)pyridin-2-yl)-5,7-dimethoxyquinazolin-4(3H)-one;

2-(4-(6-(5,7-Dimethoxy-4-oxo-3,4-dihydroquinazolin-2-yl)pyridin-2-yl)piperazin-1-yl)propanamide;

2-(4-(6-(5,7-Dimethoxy-4-oxo-3,4-dihydroquinazolin-2-yl)pyridin-2-yl)piperazin-1-yl)acetic acid;

3-(4-(6-(5,7-Dimethoxy-4-oxo-3,4-dihydroquinazolin-2-yl)pyridin-2-yl)piperazin-1-yl)propanoic acid;

2-(5-(2-(Isopropylamino)ethoxy)-6-(4-isopropylpiperazin-1-yl)pyridin-2-yl)-5,7-dimethoxyquinazolin-4(3H)-one bis(trifluoroacetate);

2-(5-(2-Hydroxyethoxy)-6-(4-isopropylpiperazin-1-yl)pyridin-2-yl)-5,7-dimethoxyquinazolin-4(3H)-one acetate;

2-(6-(4-Isopropylpiperazin-1-yl)-5-methoxypyridin-2-yl)-5,7-dimethoxyquinazolin-4(3H)-one;

5,7-Dimethoxy-2-(6-(4-methylpiperazin-1-yl)pyridin-2-yl)quinazolin-4(3H)-one Hydrochloride;

5,7-Dimethoxy-2-(6-morpholinopyridin-2-yl)quinazolin-4(3H)-one Hydrochloride;

2-(6-(4-Isopropylpiperazin-1-yl)pyridin-2-yl)-5,7-dimethoxyquinazolin-4(3H)-one Hydrochloride;

5,7-Dimethoxy-2-(6-(4-(methylsulfonyl)piperazin-1-yl)pyridin-2-yl)quinazolin-4(3H)-one Hydrochloride;

5,7-Dimethoxy-2-(6-(4-propionylpiperazin-1-yl)pyridin-2-yl)quinazolin-4(3H)-one dihydrochloride;

2-(3-(4-Isopropylpiperazin-1-yl)-5-(trifluoromethoxy)phenyl)-5,7-dimethoxyquinazolin-4(3H)-one;

7-Fluoro-2-(6-(4-isopropylpiperazin-1-yl)pyridin-2-yl)-5-methoxyquinazolin-4(3H)-one Hydrochloride;

7-(Benzyloxy)-2-(6-(4-isopropylpiperazin-1-yl)pyridin-2-yl)-5-methoxyquinazolin-4(3H)-one Hydrochloride;

2-(6-(4-Isopropylpiperazin-1-yl)pyridin-2-yl)-5-methoxy-7-phenylquinazolin-4(3H)-one;

8-(Benzyloxy)-2-(3-(4-isopropylpiperazin-1-yl)phenyl)-5-methoxyquinazolin-4(3H)-one;

4-(6-(5,7-Dimethoxy-4-oxo-3,4-dihydroquinazolin-2-yl)pyridin-2-yl)-N-isopropylpiperazine-1-carboxamide Hydrochloride;

2-(6-(4-Isopropyl-2-oxopiperazin-1-yl)pyridin-2-yl)-5,7-dimethoxyquinazolin-4(3H)-one Hydrochloride;

2-(6-(4-(Dimethylamino)piperidin-1-yl)pyridin-2-yl)-5,7-dimethoxyquinazolin-4(3H)-one;

5,7-Dimethoxy-2-(6-(4-methyl-3-oxopiperazin-1-yl)pyridin-2-yl)quinazolin-4(3H)-one;

2-(3-Chloro-5-(piperazin-1-yl)phenyl)-5,7-dimethoxyquinazolin-4(3H)-one;

2-(3-Chloro-5-(4-isopropylpiperazin-1-yl)phenyl)-5,7-dimethoxyquinazolin-4(3H)-one; and stereoisomers, tautomers, pharmaceutically acceptable salts, or hydrates thereof.

5. The method according to claim 1, wherein $R_6$ is selected from the group represented by Formula II:

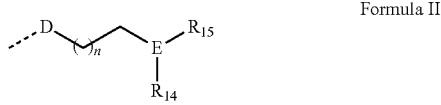

Formula II wherein:
D is selected from O and S;
E is selected from O, N, and S;
$R_{14}$ and $R_{15}$ are independently selected from hydrogen, alkyl, and cycloalkyl, wherein if E is O or S, only one of $R_{14}$ and $R_{15}$ is present; and
n is selected from 1, 2, and 3.

6. The method according to claim 5
wherein D is O;
wherein n=1;
wherein $R_{14}$ and $R_{15}$ are independently selected from hydrogen, and alkyl; and
wherein $R_6$ is selected from hydrogen, methoxy,

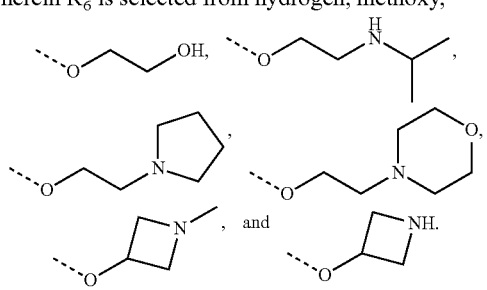

7. The method of claim 1, further comprising treating a disease, disorder, or condition characterized by dysregulation of cell cycle control, inflammatory cytokine expression, viral transcription, hematopoietic differentiation, insulin transcription, or adipogenesis.

8. The method of claim 7, wherein the disease, disorder, or condition is an autoimmune disease.

9. The method of claim 8, wherein the autoimmune disease is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Lupus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

10. The method of claim 7, wherein the disease, disorder, or condition is an inflammatory disease.

11. The method of claim 10, wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

12. The method of claim 7, wherein the disease, disorder, or condition is a cardiovascular disease.

13. The method of claim 7, wherein the disease, disorder, or condition is insulin resistance diabetes.

14. The method of claim 7, wherein the disease, disorder, or condition is a neurological disorder.

15. The method of claim 7, wherein the disease, disorder, or condition is HIV.

16. The method of claim 7, wherein the disease, disorder, or condition is cancer.

17. The method according to claim 16,
wherein $R_1$ and $R_4$ are independently selected from hydrogen, alkyl, alkoxy, halogen, and amino;
wherein $R_2$ and $R_3$ are independently selected from hydrogen, alkyl, alkoxy, and halogen;
wherein at least one of $R_1$, $R_2$, $R_3$, and $R_4$ is not hydrogen;
wherein $R_5$ is selected from hydrogen, alkyl, alkoxy, and halogen;
wherein $R_6$ is selected from hydrogen and alkoxy optionally substituted with a hydroxyl or amino; and
wherein Y is N.

18. The compound according to claim 17,
wherein AR1 is selected from

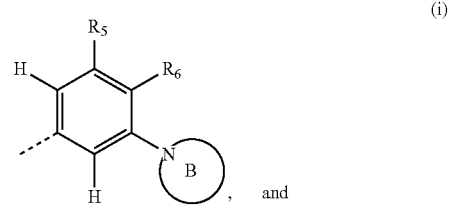

(i)

and

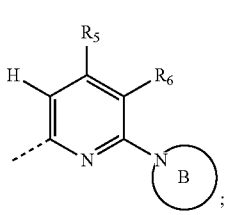

wherein B is selected from

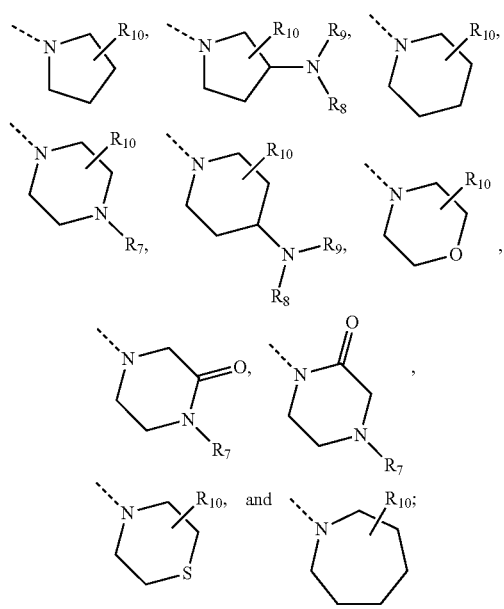

wherein $R_7$ is selected from hydrogen and alkyl;
wherein $R_8$ and $R_9$ are independently selected from hydrogen and alkyl;
wherein $R_{10}$ and $R_{11}$ are independently selected from hydrogen and halogen; and
wherein $R_{12}$ and $R_{13}$ are independently selected from hydrogen and alkyl.

19. The method according to claim 16, wherein the compound is selected from:
2-(3-(4-Isopropylpiperazin-1-yl)phenyl)-5,7-dimethoxyquinazolin-4(3H)-one;
2-(3-(4-Isopropylpiperazin-1-yl)-5-methoxyphenyl)-5,7-dimethoxyquinazolin-4(3H)-one;
5,7-Dimethoxy-2-(6-(4-(2-methoxyethyl)piperazin-1-yl)pyridin-2-yl)quinazolin-4(3H)-one;
2-(6-(4-(2-Hydroxyethyl)piperazin-1-yl)pyridin-2-yl)-5,7-dimethoxyquinazolin-4(3H)-one;
2-(6-(4-Isobutylpiperazin-1-yl)pyridin-2-yl)-5,7-dimethoxyquinazolin-4(3H)-one;
5,7-Dimethoxy-2-(6-(4-(2-(methylsulfonyl)ethyl)piperazin-1-yl)pyridin-2-yl)quinazolin-4(3H)-one;
Methyl 2-(4-(6-(5,7-dimethoxy-4-oxo-3,4-dihydroquinazolin-2-yl)pyridin-2-yl)piperazin-1-yl)acetate;
2-(6-(4-(1-Hydroxypropan-2-yl)piperazin-1-yl)pyridin-2-yl)-5,7-dimethoxyquinazolin-4(3H)-one;
2-(4-(6-(5,7-Dimethoxy-4-oxo-3,4-dihydroquinazolin-2yl)-pyridin-2-yl)piperazin-1-yl)propanamide;
2-(4-(6-(5,7-Dimethoxy-4-oxo-3,4-dihydroquinazolin-2-yl)pyridin-2-yl)piperazin-1-yl)acetic acid;
3-(4-(6-(5,7-Dimethoxy-4-oxo-3,4-dihydroquinazolin-2-yl)pyridin-2-yl)piperazin-1-yl)propanoic acid;
2-(5(2-(Isopropylamino)ethoxy)-6-(4-isopropylpiperazin-1-yl)pyridin-2-yl)-5,7-dimethoxyquinazolin-4(3H)-one bis(trifluoroacetate);
2-(5-(2-Hydroxyethoxy)-6-(4-isopropylpiperazin-1-yl)pyridin-2-yl)-5,7-dimethoxyquinazolin-4(3H)-one acetate;
2-(6-(4-Isopropylpiperazin-1-yl)-5-methoxypyridin-2-yl)-5,7-dimethoxyquinazolin-4(3H)-one;
5,7-Dimethoxy-2-(6-(4-methylpiperazin-1-yl)pyridin-2-yl)quinazolin-4(3H)-one Hydrochloride;
5,7-Dimethoxy-2-(6-morpholinopyridin-2-yl)quinazolin-4(3H)-one Hydrochloride;
2-(6-(4-Isopropylpiperazin-1-yl)pyridin-2-yl)5,7-dimethoxyquinazolin-4(3H)-one Hydrochloride;
5,7-Dimethoxy-2-(6-(4-methylsulfonyl)piperazin-1-yl)pyridin-2-yl)quinazolin-4(3H)-one Hydrochloride;
5,7-Dimethoxy-2-(6-(4-propionylpiperazin-1-yl)pyridin-2-yl)quinazolin-4(3H)-one dihydrochloride, 2-(3(4-Isopropylpiperazin-1-yl)-5-(trifluoromethoxy)phenyl)-5,7-dimethoxyquinazolin-4(3H)-one;
7-Fluoro-2-(6-(4-isopropylpiperazin-1-yl)pyridin-2-yl)-5-methoxyquinazolin-4(3H)-one Hydrochloride;
7-(Benzyloxy)-2-(6-(4-isopropylpiperazin-1-yl)pyridin-2-yl)-5-methoxyquinzolin-4(3H)-one Hydrochloride;
2-(6-(4-Isopropylpiperazin-1-yl)pyrdin-2-yl)-5-methoxy-7-phenyiquinazolin-4(3H)-one;
8-(Benzyloxy)-2-(3-(4-isopropylpiperazin-1-yl)phenyl)-5-methoxyquinazolin-4(3)-one;
4-(6-(5,7-Dimethoxy-4-oxo-3,4-dihydroquinazolin-2-yl)pyridin-2-yl)-N-isopropylpiperazine-1-carboxamide Hydrochloride;
2-(6-(4-Isopropyl-2-oxopiperazin-1-yl)pyridin-2-yl)-5,7-dimethoxyquinazolin-4(3H)-one Hydrochloride;
2-(6-(4-(Dimethylamino)piperidin-1-yl)pyridin-2-yl)-5,7-dimethoxyquinazolin-4(3H)-one;
5,7-Dimethoxy-2-(6-(4-methyl-3-oxopiperazin-1-yl)pyridin-2yl)quinazolin-4(3H)-one;
2-(3-Chloro-5-(piperazin-1yl)-phenyl)-5,7-dimethoxyquinazolin-4(3H)-one;
2-(3-Chloro-5-(4-isopropylpiperazin-1-yl)phenyl)-5,7-dimethoxyquinazolin-4(3H)-one; and
stereoisomers, tautomers, pharmaceutically acceptable salts, or hydrates thereof.

20. The method according to claim 16, wherein $R_6$ is selected from the group represented by Formula II:

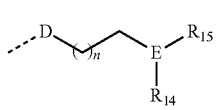

Formula II wherein:
D is selected from O and S;
E is selected from O, N, and S;
$R_{14}$ and $R_{15}$ are independently selected from hydrogen, alkyl, and cycloalkyl, wherein if E is O or S, only one of $R_{14}$ and $R_{15}$ is present; and
n is selected from 1, 2, and 3.

21. The method according to claim 20,
wherein D is O;
wherein n =1;
wherein $R_{14}$ and $R_{15}$ are independently selected from hydrogen, and alkyl; and wherein $R_6$ is selected from hydrogen, methoxy,

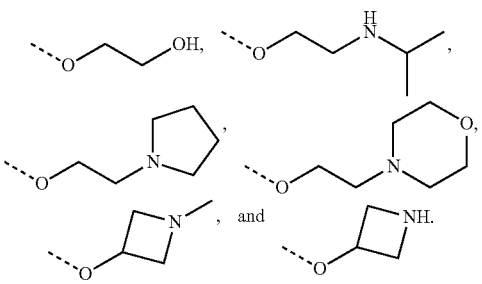

22. The method of claim 16, wherein the cancer is a midline carcinoma.

23. The method of claim 16, wherein the cancer exhibits overexpression, translocation, amplification, or rearrangement of a myc family oncoproteins.

24. The method of claim 23, wherein the cancer is characterized by overexpression of c-myc.

25. The method of claim 23, wherein the cancer is characterized by is characterized by overexpression n-myc.

26. The method of claim 16, wherein the cancer is characterized by recruitment of pTEFb to regulate oncogenes.

27. The method of claim 16, wherein the cancer is characterized by upregulation of at least one of CDK6, Bcl2, TYRO3, MYB and hTERT.

28. The method of claim 16, wherein the cancer is associated with a viral infection.

29. The method of claim 16, wherein the cancer is selected from B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, nodular melanoma, neuroblastoma, oesophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, B-cell lymphoma, non-small cell lung cancer, esophageal cancer and head and neck squamous cell carcinoma, chronic lymphocytic leukemia, follicular lymphoma, diffuse large B cell lymphoma with germinal center phenotype, Burkitt's lymphoma, Hodgkin's lymphoma, follicular lymphomas, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, hepatoma, pro-myelocytic leukemia, chronic lymphocytic leukemia, and mantle cell lymphoma.

30. The method of claim 16, wherein the compound of Formula I is administered in combination with another anticancer agent.

31. The method of claim 30, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

* * * * *